(12) United States Patent
Burke et al.

(10) Patent No.: US 10,087,206 B2
(45) Date of Patent: Oct. 2, 2018

(54) SCALABLE SYNTHESIS OF REDUCED TOXICITY DERIVATIVE OF AMPHOTERICIN B

(71) Applicant: THE BOARD OF TRUSTEES OF THE UNIVERSITY OF ILLINOIS, Urbana, IL (US)

(72) Inventors: Martin D. Burke, Champaign, IL (US); Brice E. Uno, Champaign, IL (US); Souvik Rakshit, Uluberia (IN)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/519,471

(22) PCT Filed: Oct. 16, 2015

(86) PCT No.: PCT/US2015/055899
§ 371 (c)(1),
(2) Date: Apr. 14, 2017

(87) PCT Pub. No.: WO2016/061437
PCT Pub. Date: Apr. 21, 2016

(65) Prior Publication Data
US 2017/0233427 A1    Aug. 17, 2017

Related U.S. Application Data

(60) Provisional application No. 62/065,330, filed on Oct. 17, 2014.

(51) Int. Cl.
*C07H 17/08*    (2006.01)
*C07H 1/00*    (2006.01)

(52) U.S. Cl.
CPC .............. *C07H 17/08* (2013.01); *C07H 1/00* (2013.01)

(58) Field of Classification Search
None
See application file for complete search history.

(56) References Cited

U.S. PATENT DOCUMENTS

| 6,284,736 B1 | 9/2001 | Maclachlan |
| 7,511,158 B2 | 3/2009 | Gallop et al. |
| 9,738,677 B2 * | 8/2017 | Burke ................ A61K 31/7048 |
| 2017/0190729 A1 * | 7/2017 | Miyazaki ............... C07H 17/08 |

OTHER PUBLICATIONS

Fowler et al., "Catalytic site-selective thiocarbonylations and deoxygenations of vancomycin reveal hydroxyl-dependent conformational effects," J Am Chem Soc, 134(23): 9755-9761 (2012).
Palacios et al., "A post-PKS oxidation of the amphotericin B skeleton predicted to be critical for channel formation is not required for potent antifungal activity," J Am Chem Soc, 129(45): 13804-13805 (2007).
Wilcock et al., "Electronic tuning of site-selectivity," Nat Chem, 4(12): 996-1003 (2012).
International Search Report for International Application No. PCT/US2015/55899, dated Jan. 5, 2016.

* cited by examiner

*Primary Examiner* — Traviss C McIntosh, III
(74) *Attorney, Agent, or Firm* — Dana M. Gordon; Foley Hoag LLP

(57) ABSTRACT

Disclosed is a simplified, readily scalable series of individual methods that collectively constitute a method for the synthesis of C2'epiAmB, an efficacious and reduced-toxicity derivative of amphotericin B (AmB), beginning from AmB. Also provided are various compounds corresponding to intermediates in accordance with the series of methods.

13 Claims, 3 Drawing Sheets

SCALABLE SYNTHESIS OF REDUCED TOXICITY DERIVATIVE OF AMPHOTERICIN B

RELATED APPLICATIONS

This application is the U.S. national phase of International Patent Application No. PCT/US2015/055899, filed Oct. 16, 2015, which claims benefit of U.S. Provisional Patent Application No. 62/065,330, filed Oct. 17, 2014, both of which are incorporated by reference.

GOVERNMENT SUPPORT

This invention was made with government support under Grant No. GM080436, awarded by the National Institutes of Health. The government has certain rights in the invention.

BACKGROUND OF THE INVENTION

The polyene macrolide natural product amphotericin B (AmB) is the archetype for both small molecules that form ion channels in living cells and antibiotics that are inherently refractory to microbial resistance. AmB is also, unfortunately, highly toxic, which often limits its effective utilization as the last line of defense against life-threatening systemic fungal infections. Because both the incidence of such fungal infections and resistance to all other classes of antifungals are on the rise, finding a way to improve the therapeutic index of AmB has become an increasingly important problem. Some progress has been made with liposomal formulations, but they are often prohibitively expensive, and substantial toxicity still remains. Despite 50 years of extensive efforts worldwide, a clinically viable derivative of AmB with an improved therapeutic index has yet to emerge.

The inventors recently found that epimerization of the C2' hydroxyl group of AmB results in an efficacious non-toxic AmB derivative, C2'epiAmB, that has shown remarkable potential as a clinically viable therapeutic replacement for AmB.

SUMMARY OF THE INVENTION

Provided is a simplified, readily scalable series of individual methods that collectively constitute a method for the synthesis of C2'epiAmB, beginning from AmB. Also provided are intermediates in accordance with the series of methods of the invention.

The overall method can be summarized as follows:

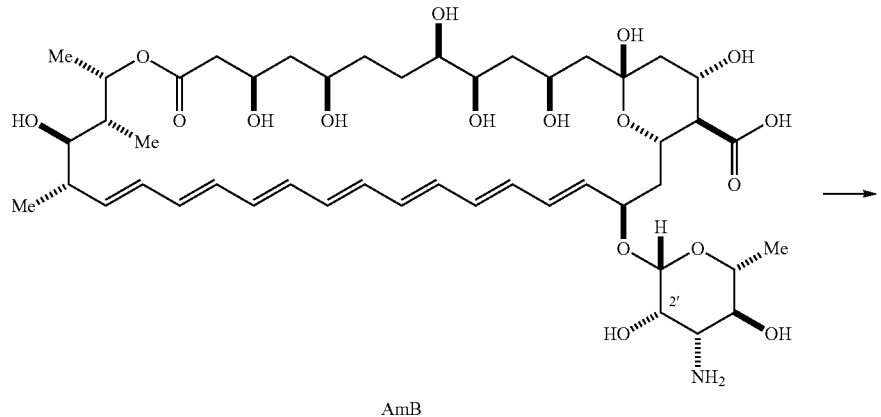

AmB

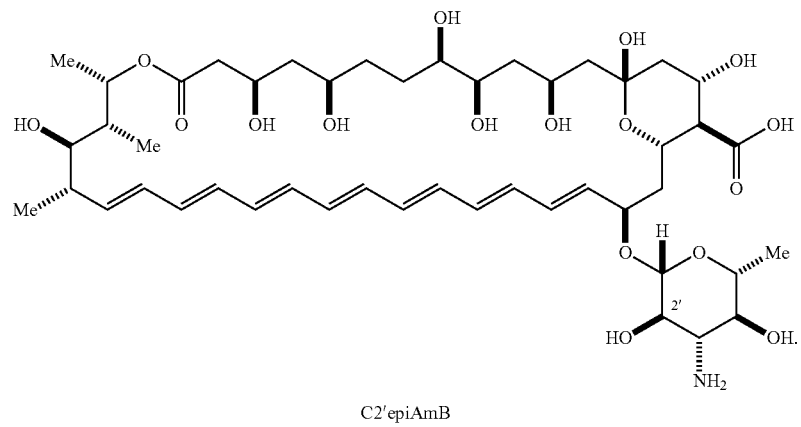

C2'epiAmB

An aspect of the invention is a method of making C2'epiAmB
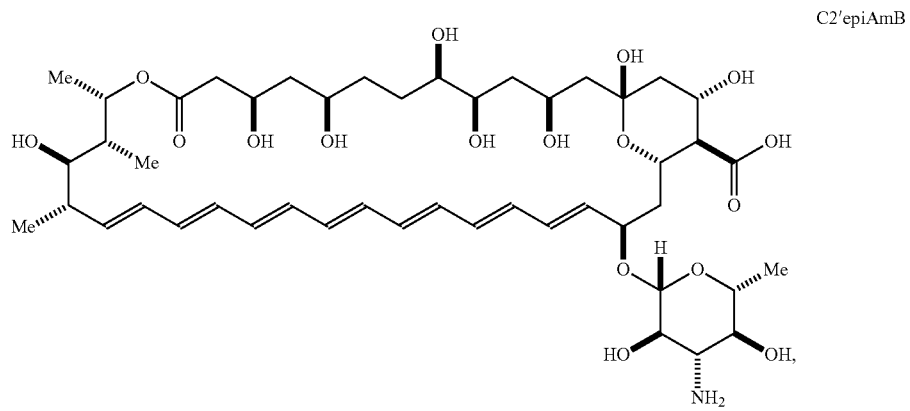
comprising the step of:
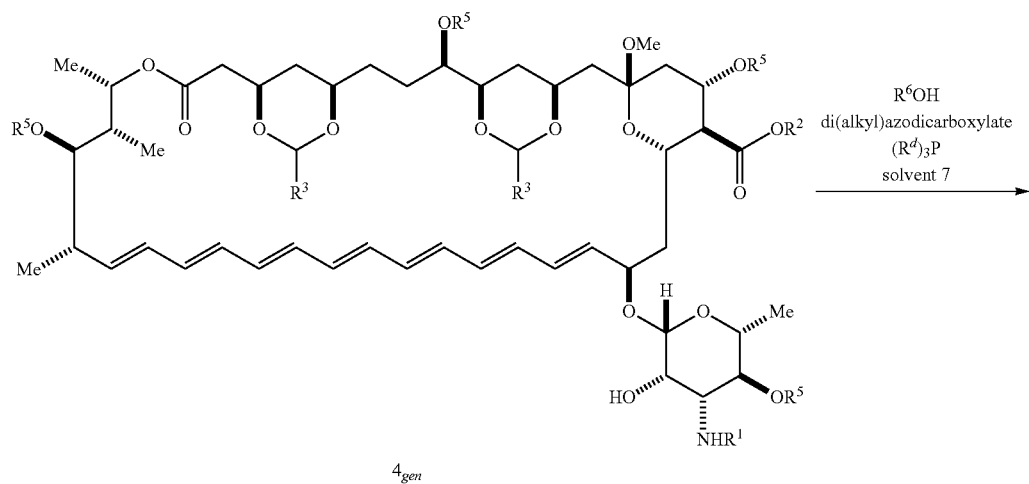
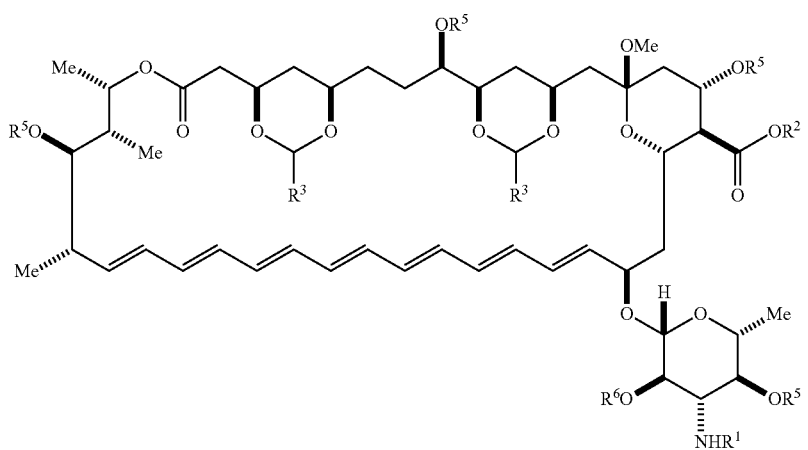

wherein, independently for each occurrence, $R^1$ is $C(O)OR^a$;

$R^2$ is selected from the group consisting of 2-alken-1-yl, benzyl, and $(R^b)_3Si-$;

$R^3$ is substituted or unsubstituted aryl, or $C_1$-$C_6$ alkyl;

$R^5$ is $(R^b)_3Si-$;

$R^6$ is $-C(O)R^c$;

$R^a$ is selected from the group consisting of 2-alken-1-yl, tert-butyl, and benzyl;

$R^b$ is substituted or unsubstituted aryl, or $C_1$-$C_6$ alkyl;

$R^c$ is substituted or unsubstituted aryl;

$R^d$ is $C_1$-$C_6$ alkyl or aryl; and solvent 7 is a nonpolar aprotic solvent.

In certain embodiments, $R^6$ is para-nitrobenzoyl; di(alkyl)azodicarboxylate is di(isopropyl)azodicarboxylate (DIAD); $R^d$ is phenyl; and solvent 7 is benzene.

In an embodiment, $R^a$ is 2-propen-1-yl; $R^2$ is 2-propen-1-yl; $R^3$ is para-methoxyphenyl (PMP); $R^5$ is diethylisopropylsilyl; $R^6$ is para-nitrobenzoyl; di(alkyl)azodicarboxylate is di(isopropyl)azodicarboxylate (DIAD); $R^d$ is phenyl; and solvent 7 is benzene.

In certain embodiments, the method further includes the step of:

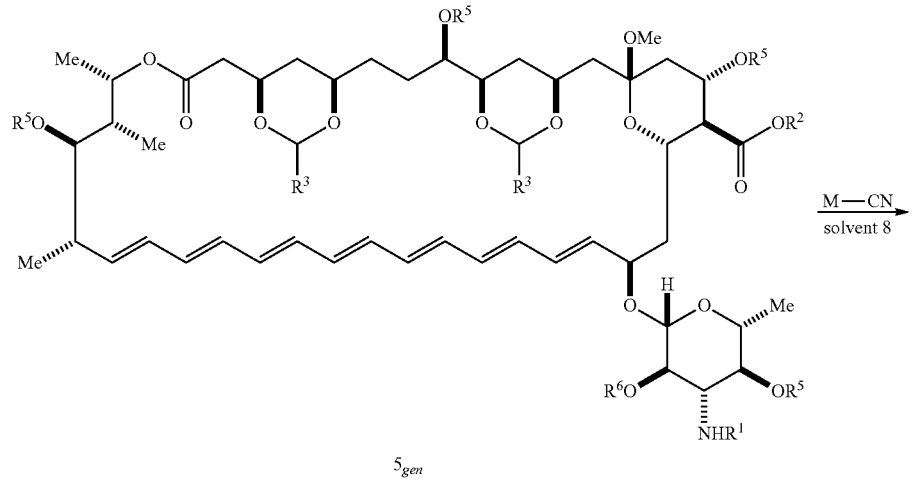

$5_{gen}$

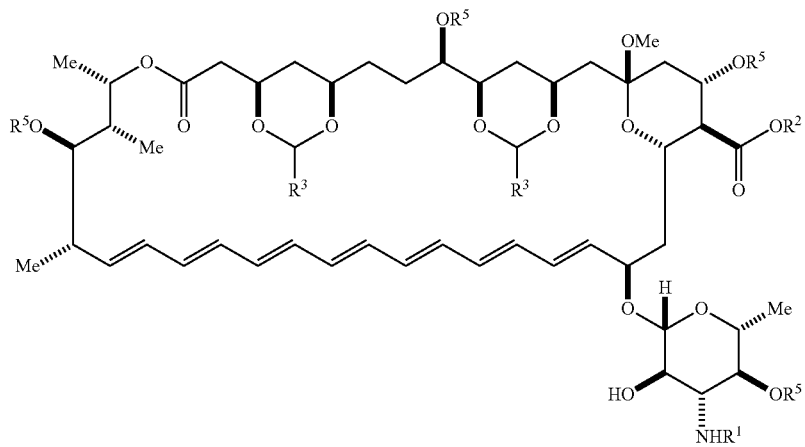

$6_{gen}$ wherein
  M is an alkali metal cation or alkaline earth metal cation; and
  solvent 8 is a polar aprotic solvent, a polar protic solvent, or a mixture thereof.

In certain embodiments, M is K; and solvent 8 is a mixture of tetrahydrofuran (THF) and MeOH.

In certain embodiments, the method further includes the step of:

wherein
  fluoride reagent is selected from the group consisting of tetraalkylammonium fluoride and fluoride salts; and
  solvent 9 is a polar aprotic solvent, a polar protic solvent, or a mixture thereof.

In certain embodiments, fluoride reagent is hydrogen fluoride pyridine; and solvent 9 is tetrahydrofuran (THF).

In certain embodiments, the method further includes the step of:

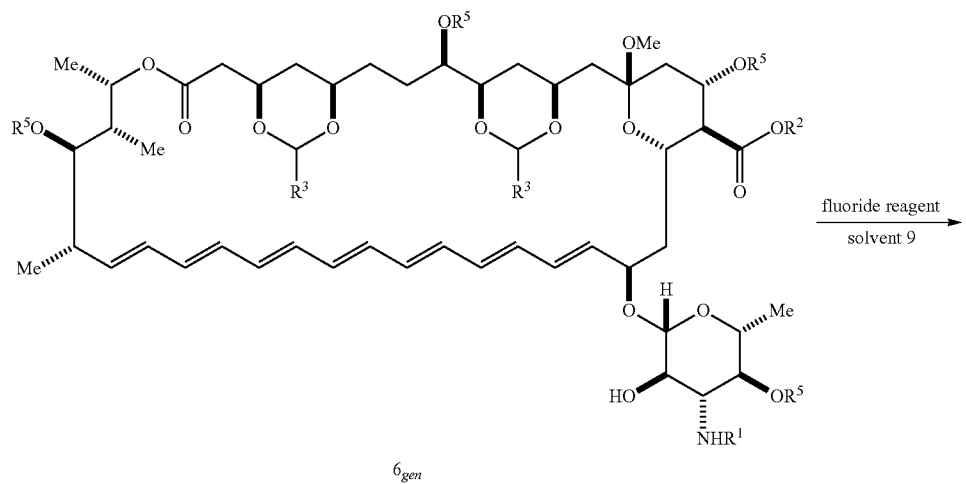

$6_{gen}$

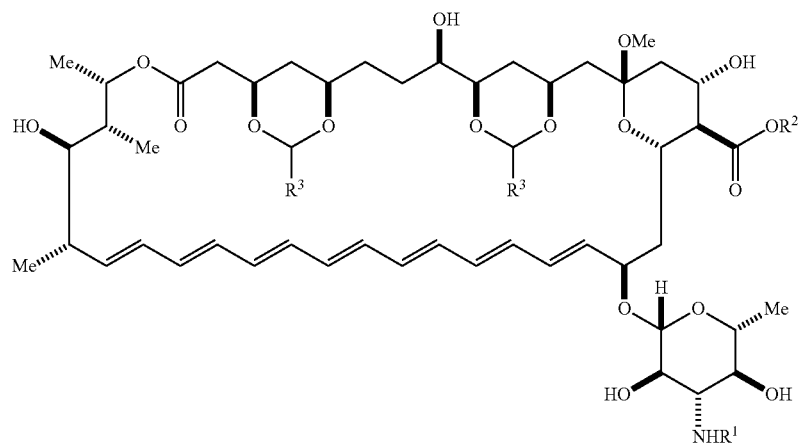

$7_{gen}$

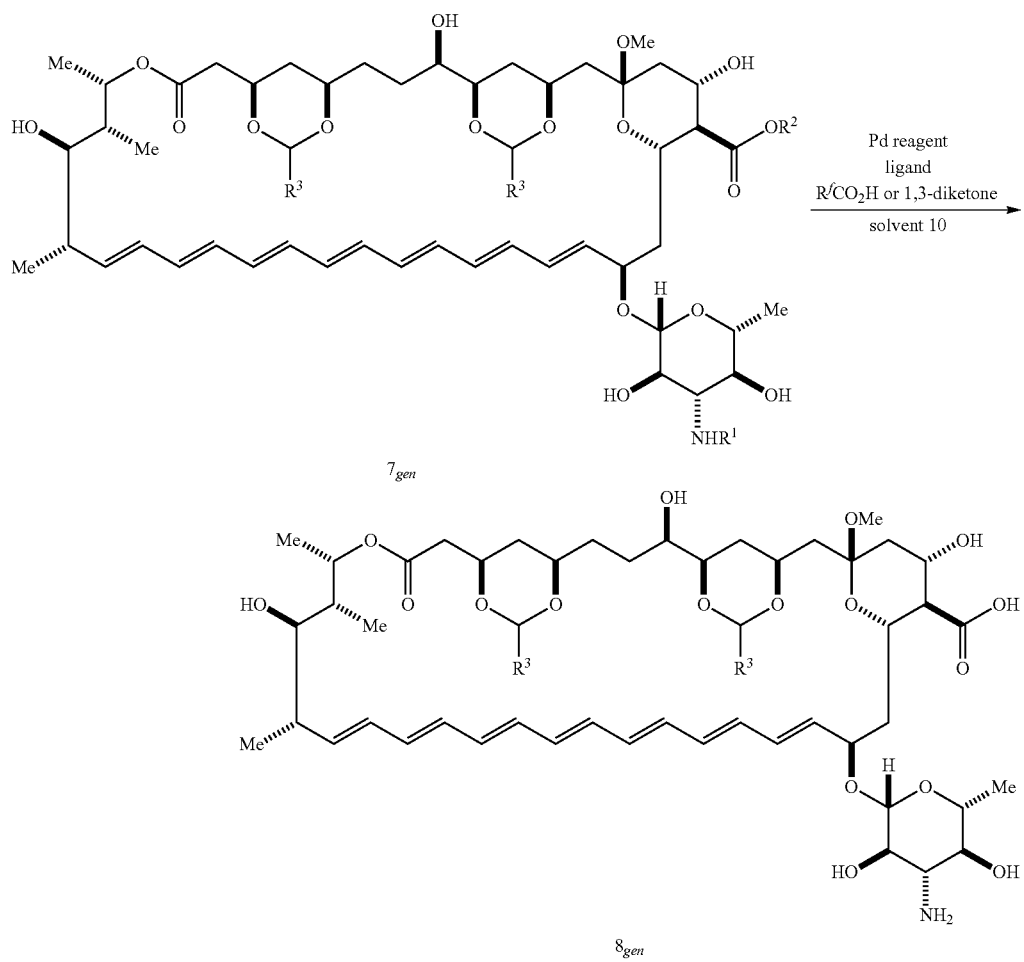

wherein, independently for each occurrence,
Pd reagent is Pd(0) or Pd(II);
ligand is $(R^e)_3P$;
$R^e$ is $C_1$-$C_6$ alkyl or aryl;
$R^f$ is $C_1$-$C_6$ alkyl or aryl; and
solvent 10 is a polar aprotic solvent.

In certain embodiments, Pd reagent is Pd(0); ligand is $(PPh_3)_4$; said $R^fCO_2H$ or 1,3-diketone is thiosalicylic acid; and solvent 10 is dimethylformamide (DMF).

In certain embodiments, the method further includes the step of:

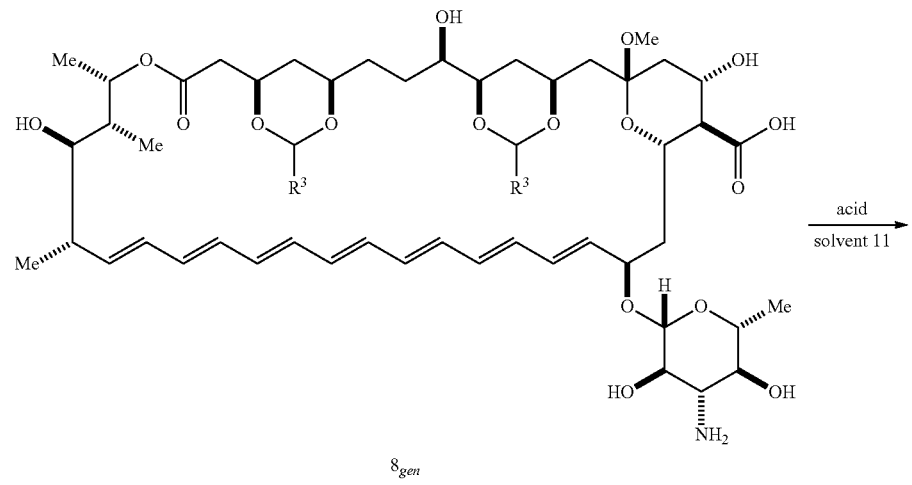

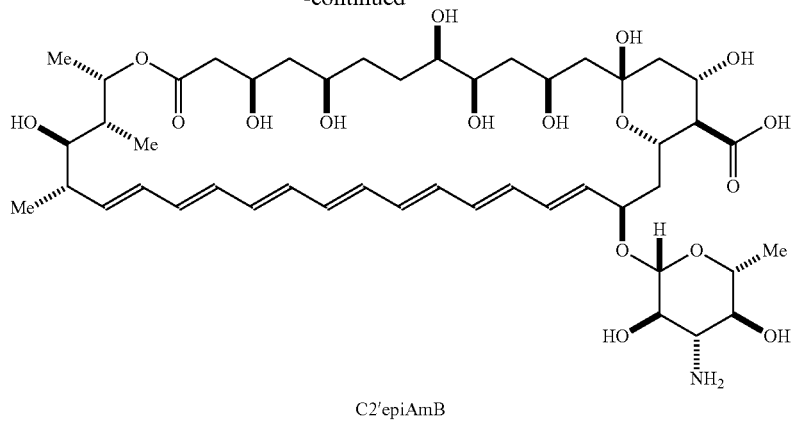

C2'epiAmB wherein
 acid is a Bronsted acid; and
 solvent 11 is a mixture of water and a polar aprotic solvent.

In certain embodiments, acid is camphorsulfonic acid (CSA).

In certain embodiments, solvent 11 is a mixture of water and MeCN.

In certain embodiments, acid is camphorsulfonic acid (CSA); and solvent 11 is a mixture of water and MeCN.

In certain embodiments, the method further includes the step of:

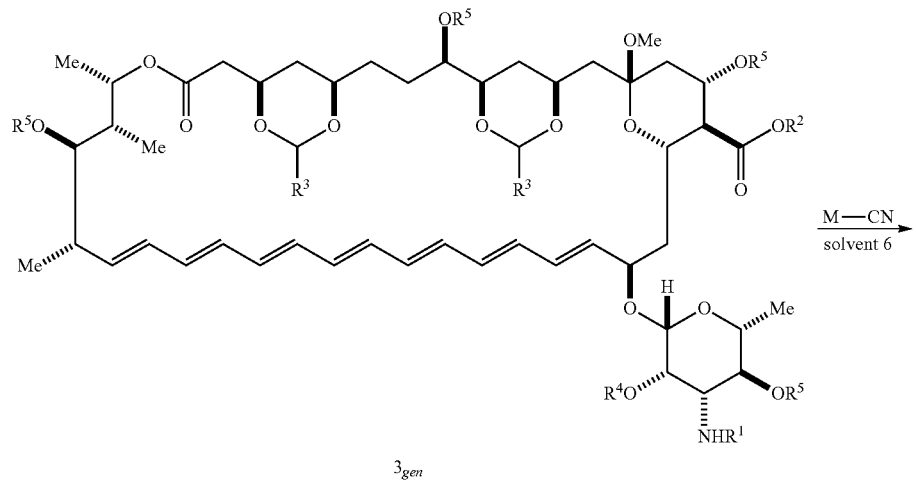

$3_{gen}$

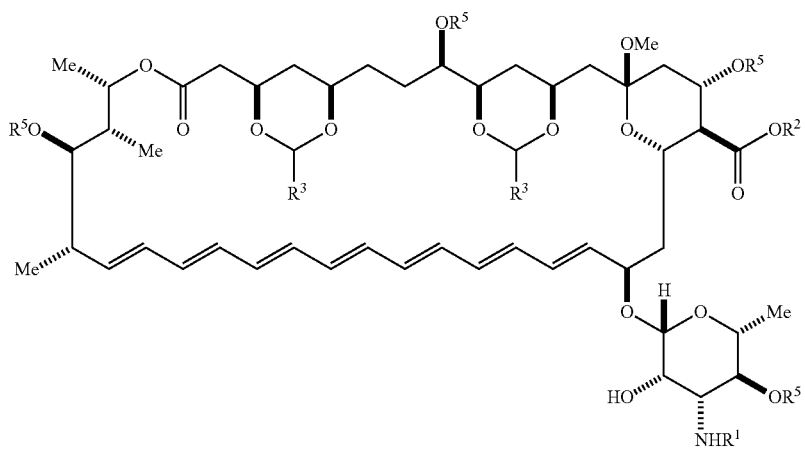

$4_{gen}$ wherein
 R⁴ is —C(O)R$^c$;
 M is an alkali metal cation or alkaline earth metal cation; and
 solvent 6 is a polar aprotic solvent, a polar protic solvent, or a mixture thereof.
 In certain embodiments, M is an alkali metal cation.

In certain embodiments, solvent 6 is a mixture of a polar aprotic solvent and a polar protic solvent.

In certain embodiments, R⁴ is p-(tert-butyl)benzoyl; M is K; and solvent 6 is a mixture of tetrahydrofuran (THF) and MeOH.

In certain embodiments, the method further includes the step of:

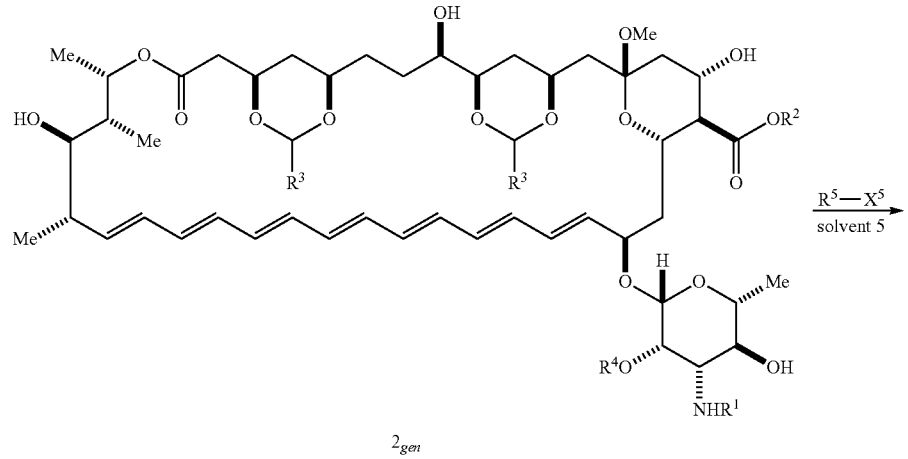

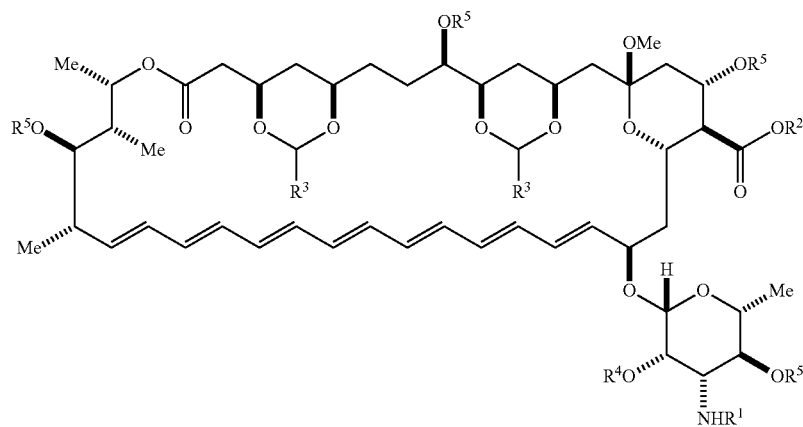

wherein
X⁵ is halide or sulfonate; and
solvent 5 is a polar aprotic solvent, a nonpolar aprotic solvent, or a mixture thereof.
In certain embodiments, $R^5$—$X^5$ is diethyl(isopropyl)silyl trifluoromethanesulfonate; and solvent 5 is a mixture of dichloromethane (DCM) and hexanes.
In certain embodiments, the method further includes the step of:
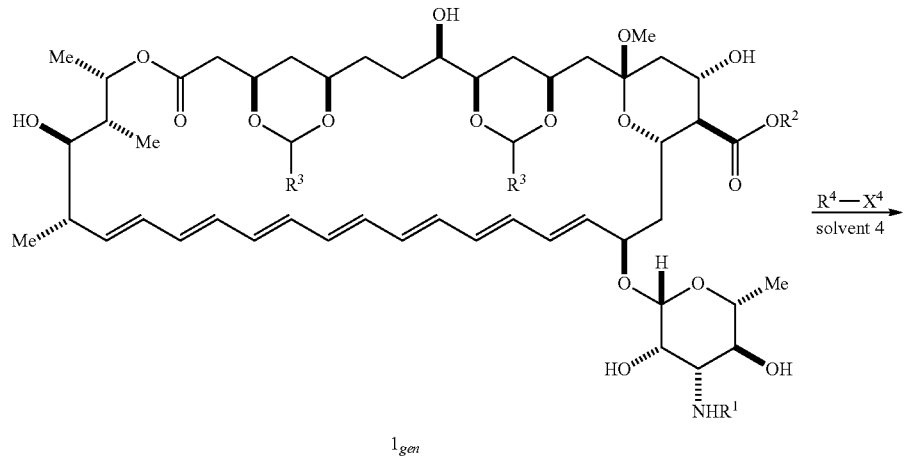
$1_{gen}$
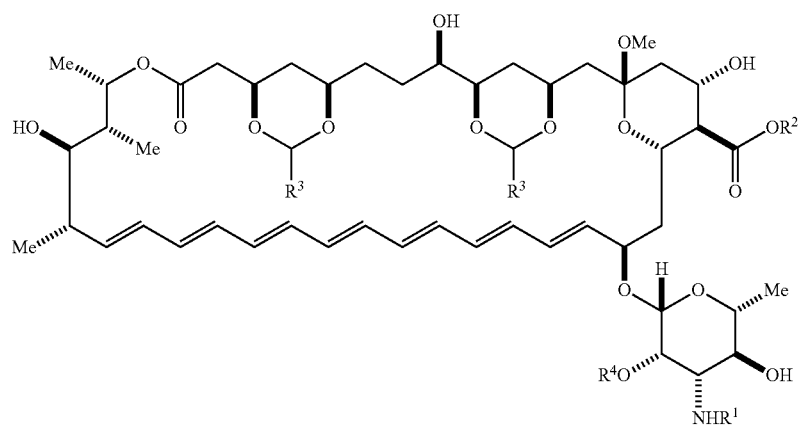
$2_{gen}$ wherein
R⁴ is substituted or unsubstituted aryloyl; and
X⁴ is selected from the group consisting of halide, succinimidyl, hydroxysuccinimidyl, azide, alkenoxyl, and aryloxyl; and solvent 4 is a polar aprotic solvent.

In certain embodiments, R⁴ is substituted aryloyl.

In certain embodiments, $R^4$—$X^4$ is p-(tert-butyl)benzoyl chloride; and solvent 4 is tetrahydrofuran (THF).

In certain embodiments, the method further includes the step of:

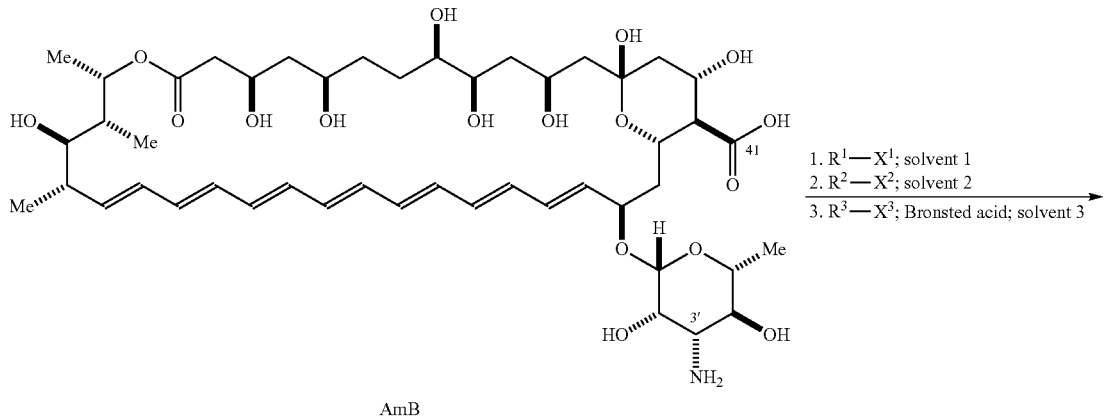

AmB

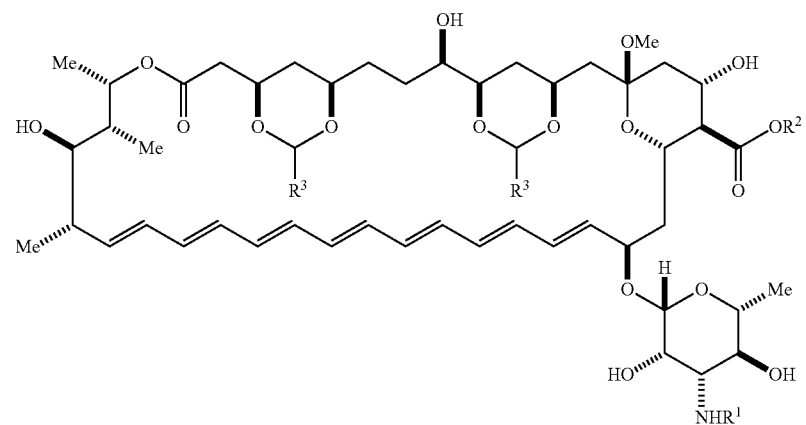

1_gen wherein
X¹ is halide or sulfonate;
X² is selected from the group consisting of halide, succinimidyl,
hydroxysuccinimidyl, azido, alkenoxyl, and aryloxyl;
X³ is —CH(OR)₂;
R is $C_1$-$C_6$ alkyl;
solvent 1 is a polar aprotic solvent, a polar protic solvent, or a mixture thereof;
solvent 2 is a polar aprotic solvent, a polar protic solvent, or a mixture thereof; and
solvent 3 is a polar aprotic solvent, a polar protic solvent, or a mixture thereof.

In certain embodiments, $R^a$ is 2-propen-1-yl; X¹ is succinimidyl; R² is 2-propen-1-yl; X² is halide; R³ is para-methoxyphenyl; solvent 1 is a mixture of dimethylformamide (DMF) and MeOH; solvent 2 is a mixture of DMF and MeOH; and solvent 3 is a mixture of tetrahydrofuran (THF) and MeOH.

An aspect of the invention is a compound, represented by

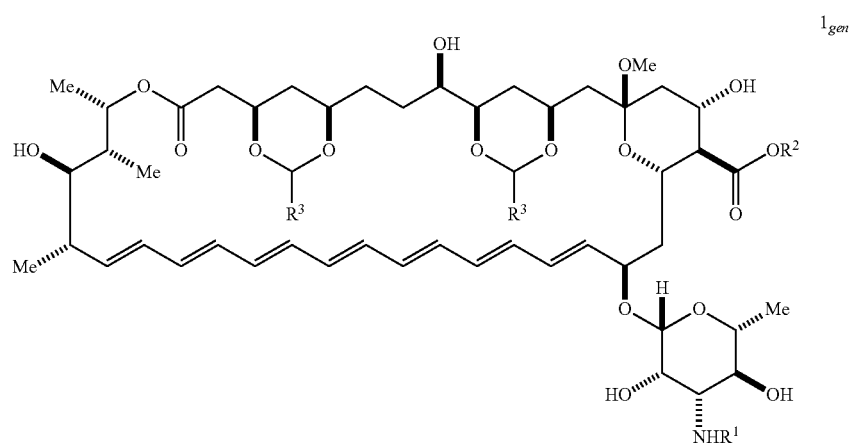

$1_{gen}$ wherein, independently for each occurrence,
R¹ is C(O)OR$^a$;
R² is selected from the group consisting of 2-alken-1-yl, benzyl, and (R$^b$)₃Si—;
R³ is substituted or unsubstituted aryl, or $C_1$-$C_6$ alkyl;
R$^a$ is selected from the group consisting of 2-alken-1-yl, tert-butyl, and benzyl; and
R$^b$ is substituted or unsubstituted aryl, or $C_1$-$C_6$ alkyl.

In an embodiment, the compound is represented by

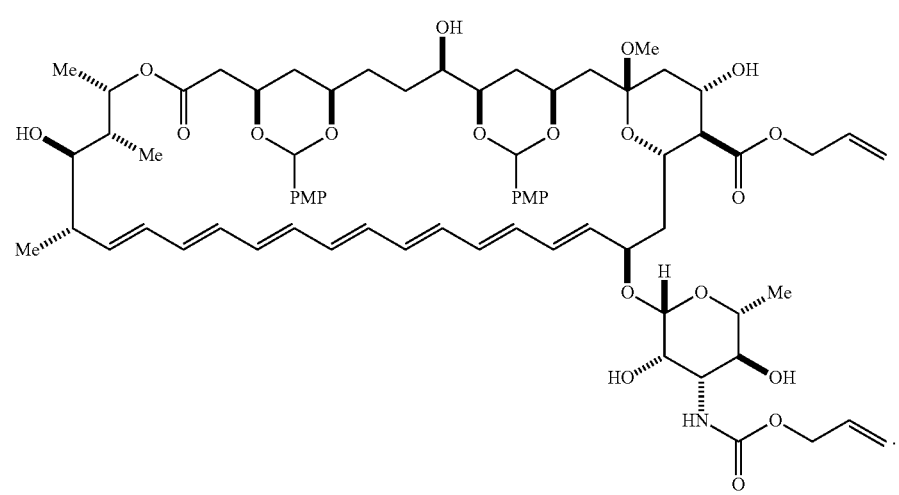

1

An aspect of the invention is a compound, represented by

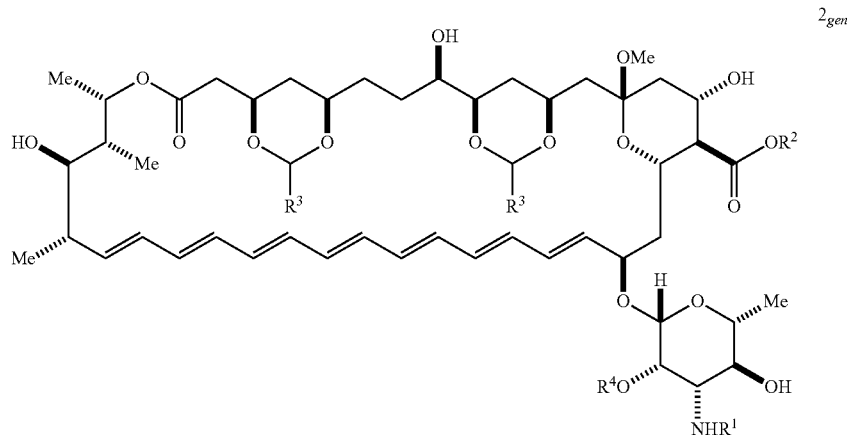

2_gen wherein, independently for each occurrence,
$R^1$ is $C(O)OR^a$;
$R^2$ is selected from the group consisting of 2-alken-1-yl, benzyl, and $(R^b)_3Si$—;
$R^3$ is substituted or unsubstituted aryl, or $C_1$-$C_6$ alkyl;
$R^4$ is —$C(O)R^c$;
$R^a$ is selected from the group consisting of 2-alken-1-yl, tert-butyl, and benzyl;
$R^b$ is substituted or unsubstituted aryl, or $C_1$-$C_6$ alkyl; and
$R^c$ is substituted or unsubstituted aryl.

In an embodiment, the compound is represented by

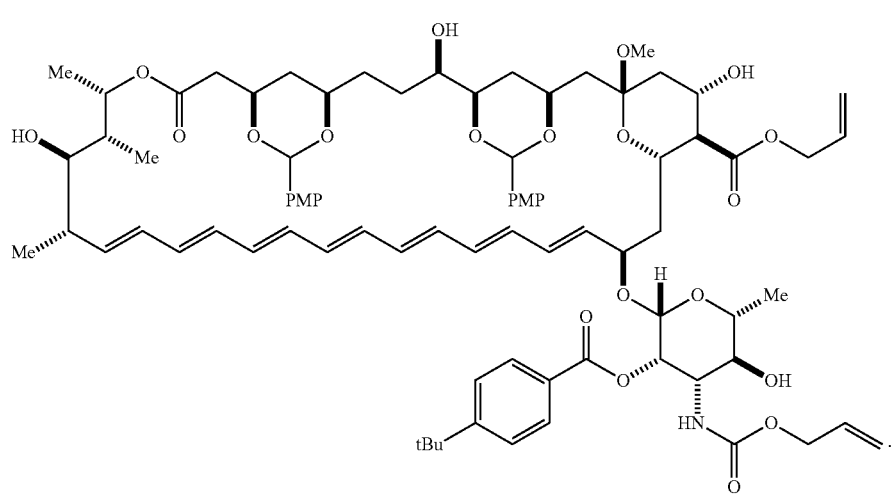

2

An aspect of the invention is a compound, represented by

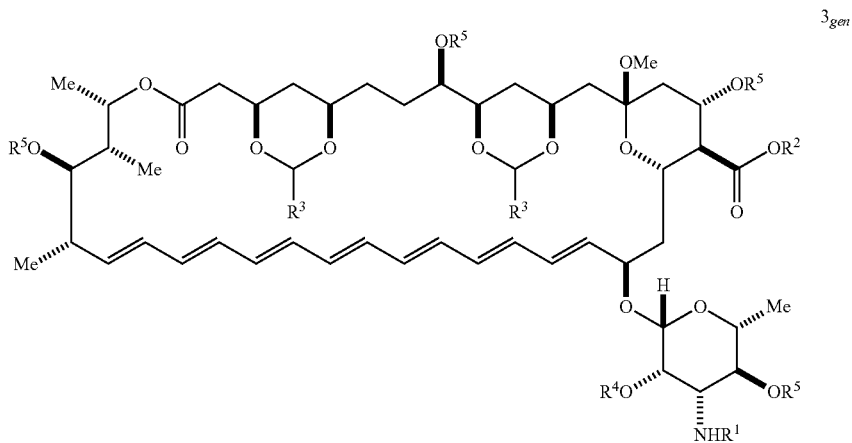

$3_{gen}$ wherein, independently for each occurrence,
$R^1$ is $C(O)OR^a$;
$R^2$ is selected from the group consisting of 2-alken-1-yl, benzyl, and $(R^b)_3Si—$;
$R^3$ is substituted or unsubstituted aryl, or $C_1$-$C_6$ alkyl;
$R^4$ is $—C(O)R^c$;
$R^5$ is $(R^b)_3Si—$;
$R^a$ is selected from the group consisting of 2-alken-1-yl, tert-butyl, and benzyl;
$R^b$ is substituted or unsubstituted aryl, or $C_1$-$C_6$ alkyl; and
$R^c$ is substituted or unsubstituted aryl.

In an embodiment, the compound is represented by

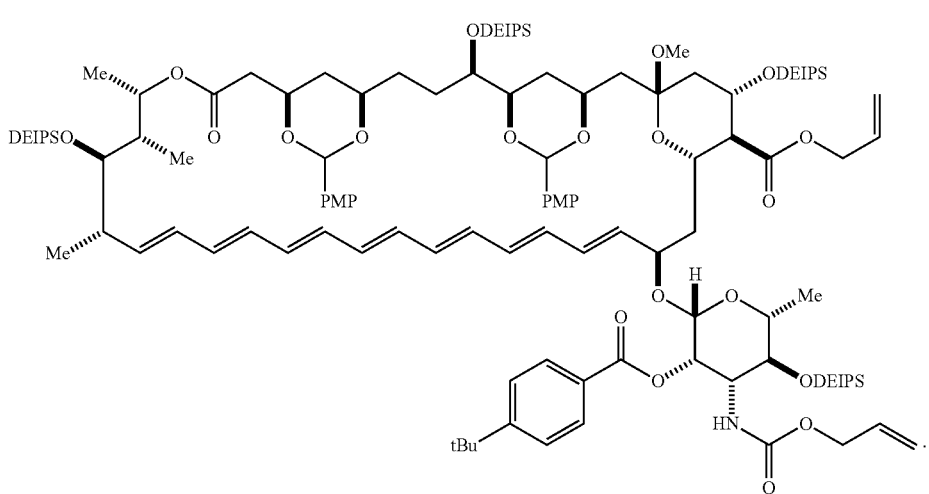

3

An aspect of the invention is a compound, represented by $4_{gen}$ wherein, independently for each occurrence,
$R^1$ is $C(O)OR^a$;
$R^2$ is selected from the group consisting of 2-alken-1-yl, benzyl, and $(R^b)_3Si—$;
$R^3$ is substituted or unsubstituted aryl, or $C_1$-$C_6$ alkyl;
$R^5$ is $(R^b)_3Si—$;
$R^a$ is selected from the group consisting of 2-alken-1-yl, tert-butyl, and benzyl; and
$R^b$ is substituted or unsubstituted aryl, or $C_1$-$C_6$ alkyl.

In an embodiment, the compound is represented by

4

An aspect of the invention is a compound, represented by

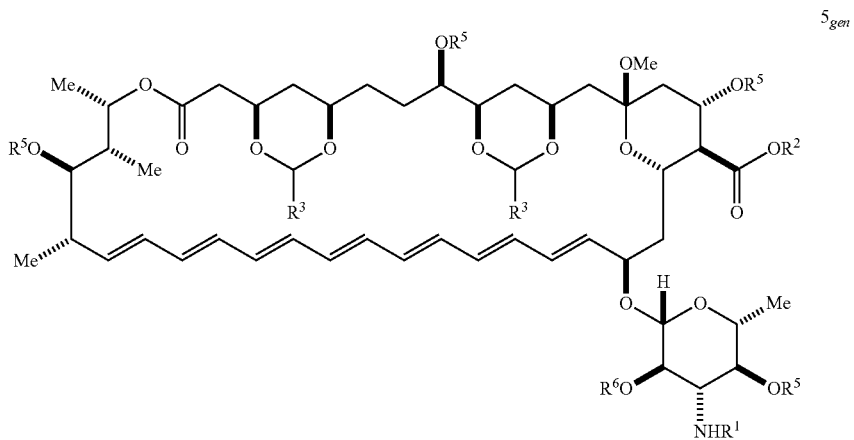

wherein, independently for each occurrence,
$R^1$ is $C(O)OR^a$;
$R^2$ is selected from the group consisting of 2-alken-1-yl, benzyl, and $(R^b)_3Si-$;
$R^3$ is substituted or unsubstituted aryl, or $C_1$-$C_6$ alkyl;
$R^5$ is $(R^b)_3Si-$;
$R^6$ is $-C(O)R^c$;
$R^a$ is selected from the group consisting of 2-alken-1-yl, tert-butyl, and benzyl;
$R^b$ is substituted or unsubstituted aryl, or $C_1$-$C_6$ alkyl; and
$R^c$ is substituted or unsubstituted aryl.

In an embodiment, the compound is represented by

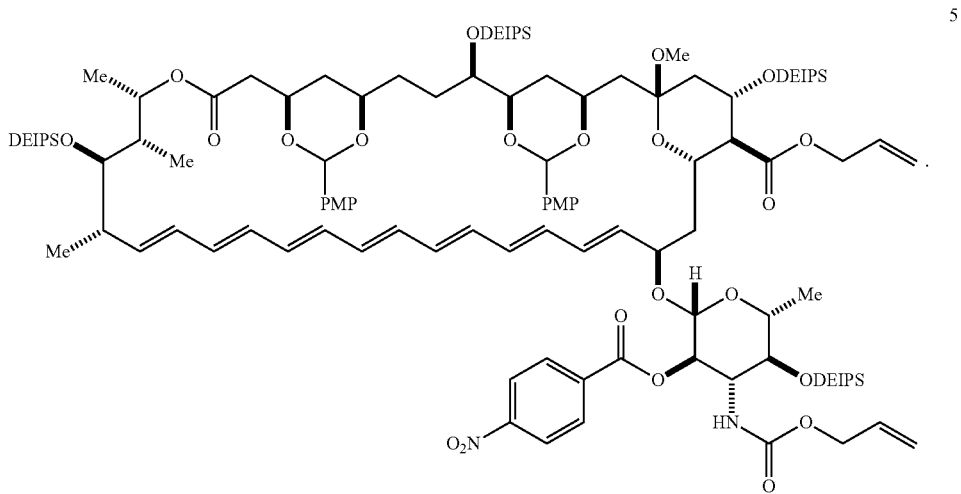

An aspect of the invention is a compound, represented by $6_{gen}$ wherein, independently for each occurrence,
$R^1$ is $C(O)OR^a$;
$R^2$ is selected from the group consisting of 2-alken-1-yl, benzyl, and $(R^b)_3Si-$;
$R^3$ is substituted or unsubstituted aryl, or $C_1$-$C_6$ alkyl;
$R^5$ is $(R^b)_3Si-$;
$R^a$ is selected from the group consisting of 2-alken-1-yl, tert-butyl, and benzyl; and
$R^b$ is substituted or unsubstituted aryl, or $C_1$-$C_6$ alkyl.

In an embodiment, the compound is represented by

6

An aspect of the invention is a compound, represented by

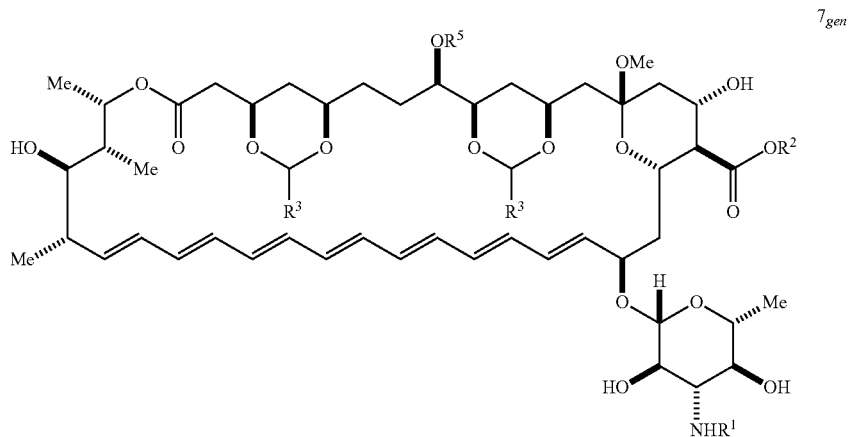

wherein, independently for each occurrence,
R¹ is C(O)OR$^a$;
R² is selected from the group consisting of 2-alken-1-yl, benzyl, and (R$^b$)₃Si—;
R³ is substituted or unsubstituted aryl, or C₁-C₆ alkyl;
R$^a$ is selected from the group consisting of 2-alken-1-yl, tert-butyl, and benzyl; and
R$^b$ is substituted or unsubstituted aryl, or C₁-C₆ alkyl.

In an embodiment, the compound is represented by

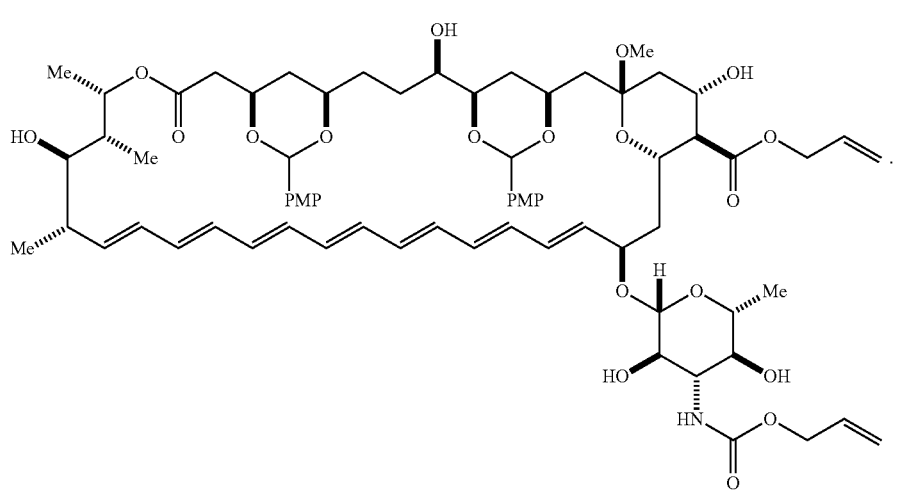

An aspect of the invention is a compound, represented by

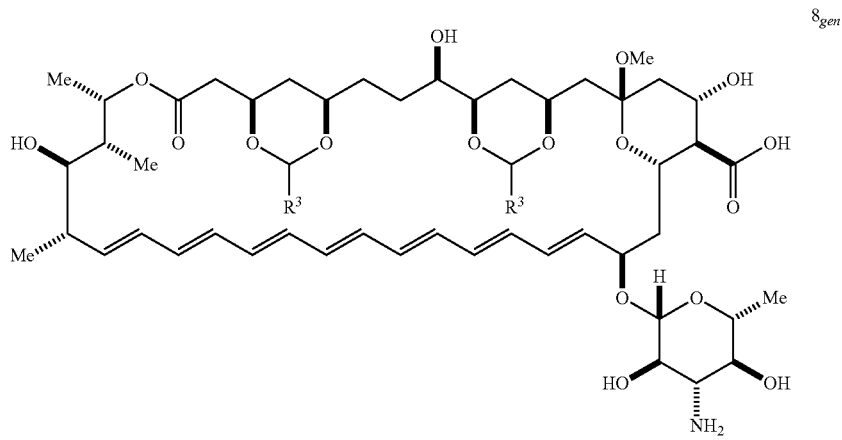

$8_{gen}$ wherein, independently for each occurrence,
R³ is substituted or unsubstituted aryl, or $C_1$-$C_6$ alkyl.
In certain embodiments, R³ is substituted or unsubstituted aryl.
In an embodiment, the compound is represented by

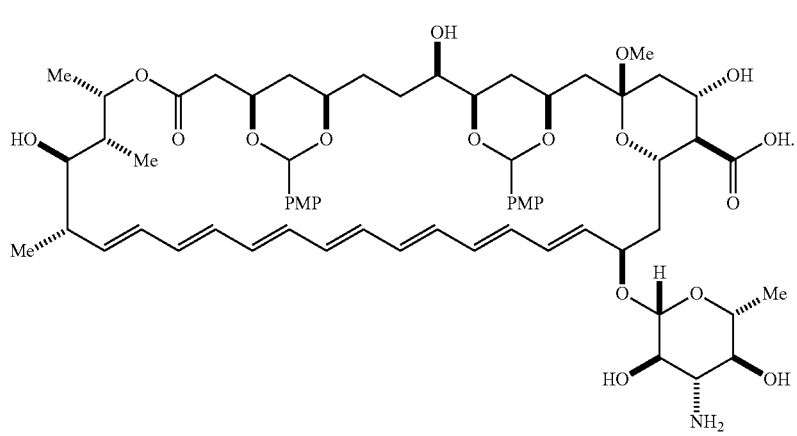

8

DETAILED DESCRIPTION OF THE INVENTION

Figure 1:
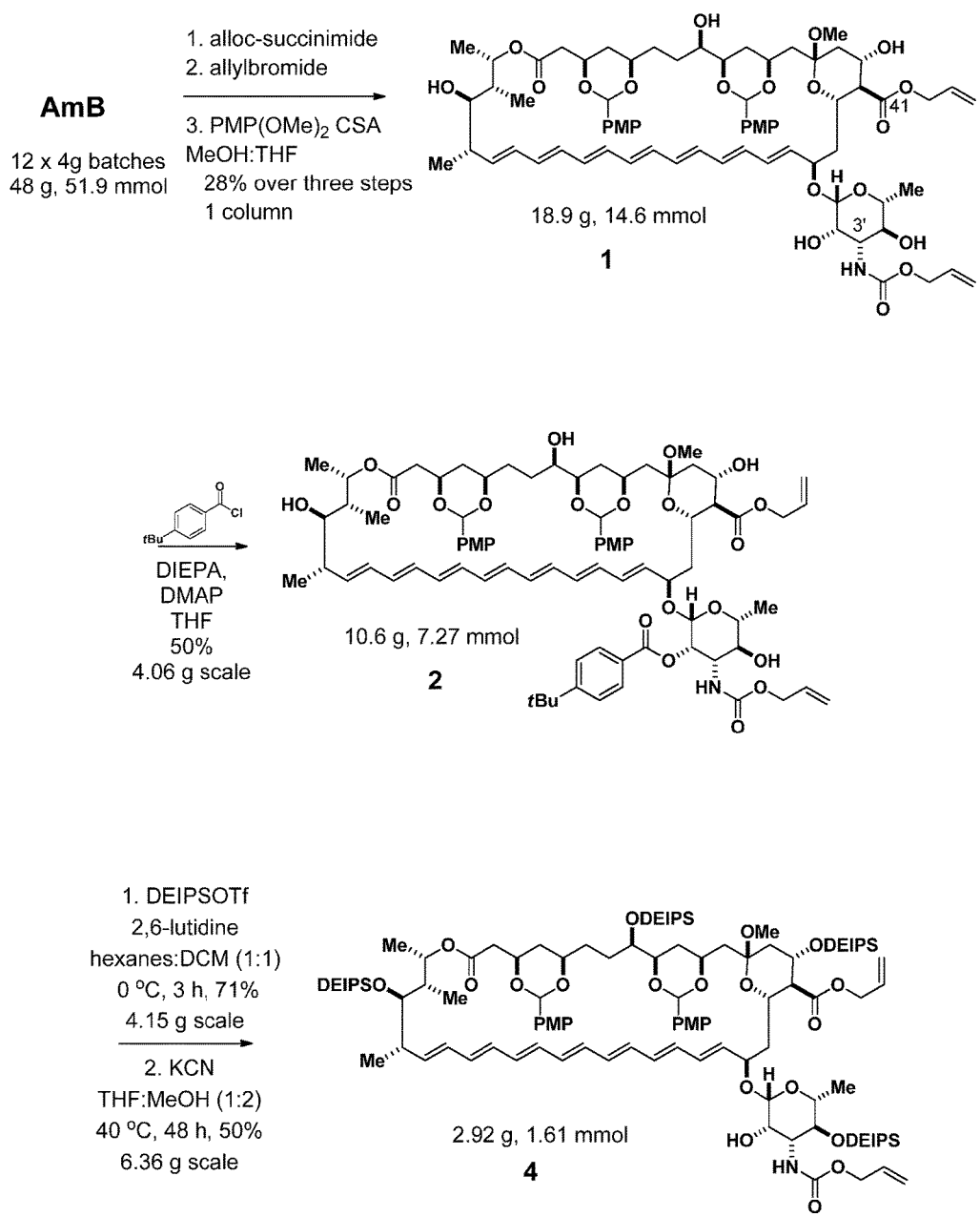
FIG. 1 depicts a portion of a scheme for scalable synthesis of C2' epimer of amphotericin B (C2'epiAmB). Steps shown proceed from amphotericin B (AmB) to compound 4. DCM, dichloromethane; DEIPSOTf, diethyl(isopropyl)silyl trifluorosulfonate; DIEPA, N,N-diisopropylethylamine; DMAP, 4-(dimethylamino)pyridine; PMP, para-methoxyphenyl; THF, tetrahydrofuran.
Figure 2:
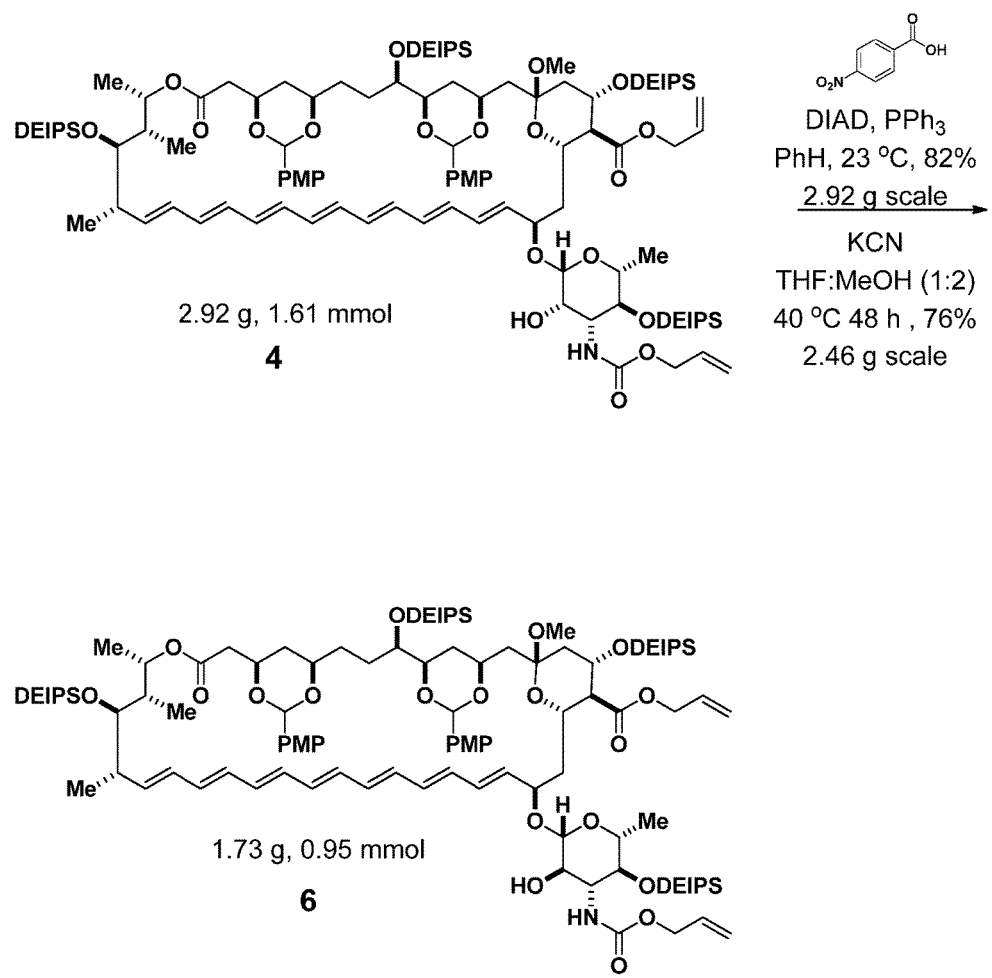
FIG. 2 depicts a portion of a scheme for scalable synthesis of C2'epiAmB. Steps shown proceed from compound 4 to compound 6. DEIPS, diethyl(isopropyl)silyl; DIAD, di(isopropyl)azodicarboxylate; PMP, para-methoxyphenyl; THF, tetrahydrofuran.
Figure 3:
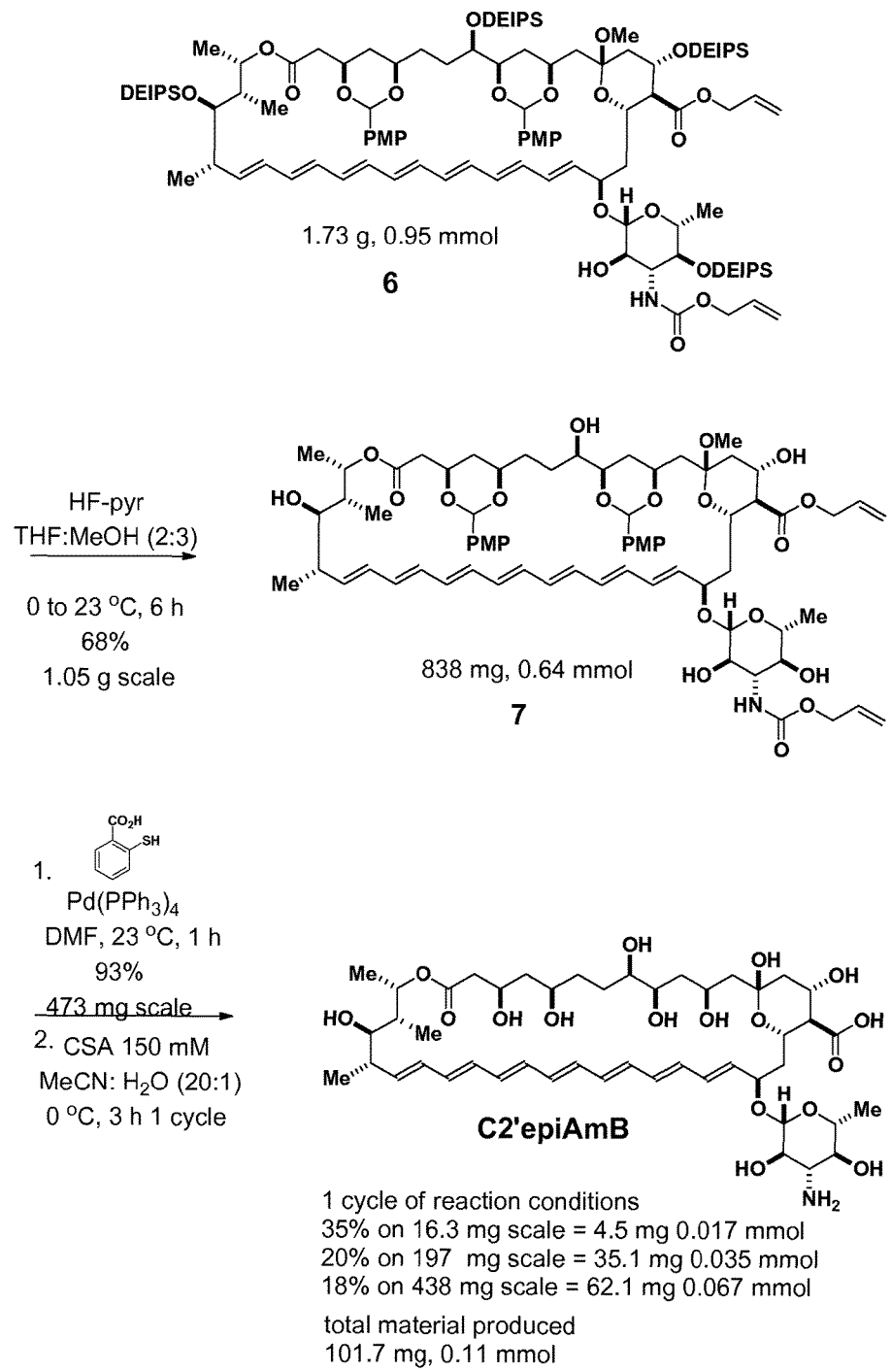
FIG. 3 depicts a portion of a scheme for scalable synthesis of C2'epiAmB. Steps shown proceed from compound 6 to C2'epiAmB. CSA, camphorsulfonic acid; DEIPS, diethyl(isopropyl)silyl; DMF, dimethylformamide; HF-pyr, HF-pyridine; PMP, para-methoxyphenyl; THF, tetrahydrofuran.

Amphotericin B (AmB) is a clinically vital antimycotic but its use is limited by its toxicity. Binding ergosterol, independent of channel formation, is the primary mechanism by which AmB kills yeast, and binding cholesterol may primarily account for toxicity to human cells. A leading structural model predicts that the C2' hydroxyl group on the mycosamine appendage is key to binding to both sterols.

AmB is generally obtained from a strain of Streptomyces nodosus. It is currently approved for clinical use in the United States for the treatment of progressive, potentially life-threatening fungal infections, including infections such as systemic candidiasis, aspergillosis, cryptococcosis, blastomycosis, coccidioidomycosis, histoplasmosis, and mucormycosis. AmB is generally formulated for intravenous injection. Amphotericin B is commercially available, for example, as Fungizone® (Squibb), Amphocin® (Pfizer), Abelcet® (Enzon), and Ambisome® (Astellas). Due to its unwanted toxic side effects, dosing is generally limited to a maximum of about 1.0 mg/kg/day, and total cumulative doses not to exceed about 3 g in humans.

It has for many decades been widely accepted that AmB primarily kills both yeast and human cells via membrane permeabilization. Guided by this model, extensive efforts have focused on the development of derivatives that selectively form ion channels in yeast vs. human cells.

In contrast to this classic model, it has been recently discovered that AmB self assembles into an extramembranous 'sterol-sponge' that primarily kills cells by binding and extracting sterols in a mycosamine-dependent fashion. Evidence supports a model in which the C2'-OH and C3'-NH$_3^+$ on the mycosamine appendage are involved in stabilizing a ground state conformation of AmB that allows for the binding of both ergosterol (Erg) and cholesterol (Chol); i.e., channel formation is not required. When either the C2'-OH or C3'-NH$_3^+$ is deleted, AmB still binds Erg but can no longer bind Chol. These results suggest the C2'-OH and the C3'-NH$_3^+$ do not directly bind sterols but are potential sites of allosteric modification. Furthermore, this shift in sterol binding directly correlates with a substantial decrease of observed toxicity to human cells. This suggests that simply binding cholesterol may alternatively account for the toxicity of AmB to human cells, and that efforts to improve the therapeutic index of this clinically vital antimycotic can focus on the much simpler problem of maximizing the relative binding affinity for ergosterol vs. cholesterol.

In the leading existing structural model, AmB binds both ergosterol and cholesterol via a similar complex in which the C2' hydroxyl group of AmB forms a critical hydrogen bond to the 3-b hydroxyl group on each sterol. However, strong evidence for or against this hypothesis was lacking. For example, computer simulations have suggested that such a hydrogen bond plays an important role in binding ergosterol, but not cholesterol. Alternatively, previous studies comparing the membrane permeabilizing activities of conformationally restricted derivatives of AmB concluded that such a hydrogen bond plays a key role with both sterols. None of these prior studies directly measured sterol binding.

The inventors have discovered an 11-step synthesis of a derivative of amphotericin B (AmB), dubbed C2'epiAmB, that retains potent antifungal activity in vitro and in mice, but is substantially less toxic than the natural product. This synthesis is amenable to large scale production of this lead candidate to enable advanced preclinical/clinical development and/or clinical supply.

The inventors discovered a new collection of protecting groups for AmB that are readily installed and removed at the beginning and end of this synthesis, respectively. This facile addition and removal of these protective groups is critical for the scalability of this route.

The inventors also discovered that the opening protection sequence, which involves the addition of five different protecting groups to AmB (C3'-alloc carbamate, C41-allyl ester, C13 hemiketal, C3,5-PMP ketal, and C9,11-PMP ketal), can proceed over just three steps on multi-gram scale with one normal-phase chromatography step.

The inventors further discovered that all three steps in the opening protection sequence are quenched, triturated with relatively non-polar solvents (Et$_2$O or Et$_2$O:Hexane 1:1), followed by filtration to remove excess reagents and solvents. This procedure yields all intermediates as free-flowing yellow powders. The "cleanliness" and overall yield of the collective process is remarkable.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "cycloalkyl" means mono- or bicyclic or bridged saturated carbocyclic rings, each having from 3 to 12 carbon atoms. Preferred cycloalkyls have from 5-12 carbon atoms in their ring structure, and more preferably have 6-10 carbons in the ring structure.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylthio", as used herein, means an alkyl group, as defined herein, appended to the parent molecular moiety through a sulfur atom. Representative examples of alkylthio include, but are not limited to, methylthio, ethylthio, tert-butylthio, and hexylthio. The terms "arylthio," "alkenylthio" and "arylakylthio," for example, are likewise defined.

The term "amido", as used herein, means —NHC (=O)—, wherein the amido group is bound to the parent molecular moiety through the nitrogen. Examples of amido include alkylamido such as CH$_3$C(=O)N(H)— and CH$_3$CH$_2$C(=O)N(H)—.

The term "amino", as used herein, refers to radicals of both unsubstituted and substituted amines appended to the parent molecular moiety through a nitrogen atom. The two groups are each independently hydrogen, alkyl, alkylcarbonyl, alkylsulfonyl, arylcarbonyl, or formyl. Representative examples include, but are not limited to methylamino, acetylamino, and acetylmethylamino.

The term "alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywhere in the moiety and can have either the (Z) or the (E) configuration about the double bond(s).

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2=CH-CH_2-O-$) and vinyloxy (i.e., $CH_2=CH-O-$).

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl", as used herein, means a phenyl group or a naphthyl group. The aryl groups of the invention can be optionally substituted with 1, 2, 3, 4 or 5 substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "arylene" is art-recognized, and, as used herein, pertains to a bidentate moiety obtained by removing two hydrogen atoms of an aryl ring, as defined above.

The term "arylalkyl" or "aralkyl", as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryloxy" or "aryloxyl" means an aryl group, as defined herein, appended to the parent molecular moiety through an oxygen atom. Representative examples of aryloxy include, but are not limited to, phenoxy and 1-naphthyloxy.

The term "arylcarbonyl" or "aryloyl", as used herein, means an aryl group, as defined herein, appended to the parent molecular moiety through a carbonyl group, as defined herein. Representative examples of arylcarbonyl include, but are not limited to, benzoyl and (2-pyridinyl) carbonyl.

The term "azide" or "azido", as used herein, means an $-N_3$ group.

The term "carbonyl", as used herein, means a $-C(=O)-$ group.

The term "carboxy", as used herein, means a $-CO_2H$ group.

The term "cyano", as used herein, means a $-CN$ group.

The term "halide", "halo", or "halogen" means $-F$, $-Cl$, $-Br$, or $-I$.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl", as used herein, include nonaromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups may be substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroaryl", as used herein, includes aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups may be substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroarylene" is art-recognized, and, as used herein, pertains to a bidentate moiety obtained by removing two hydrogen atoms of a heteroaryl ring, as defined above.

The term "heteroarylalkyl" or "heteroaralkyl", as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "hydroxyl", as used herein, means an $-OH$ group.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto", as used herein, means a —SH group.

The term "nitro", as used herein, means a —NO$_2$ group.

The term "silyl", as used herein, includes hydrocarbyl derivatives of the silyl (H$_3$Si—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

The term "sulfonate" is art-recognized and includes a moiety that can be represented by the formula:

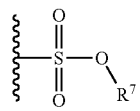

in which R$^7$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

For purposes of this invention, the chemical elements are identified in accordance with the Periodic Table of the Elements, CAS version, Handbook of Chemistry and Physics, 67th Ed., 1986-87, inside cover.

As used herein, a protic solvent is a solvent that has a hydrogen atom bound to an oxygen (as in a hydroxyl group) or a nitrogen (as in an amine group). In general terms, any solvent that contains labile H$^+$ is called a protic solvent. The molecules of such solvents readily donate protons (H$^+$) to reagents. In contrast, an aprotic solvent is a solvent that does not have a hydrogen atom bound to an oxygen (as in a hydroxyl group) or a nitrogen (as in an amine group), and it cannot donate hydrogen.

As used herein, a polar protic solvent is a protic solvent that will dissolve many salts. In general, these solvents have high dielectric constants and high polarity. Non-limiting examples of polar protic solvents include acetic acid, ammonia, ethanol, formic acid, isopropanol, methanol, n-butanol, nitromethane, n-propanol, t-butanol, and water.

As used herein, a polar aprotic solvent is a solvent that will dissolve many salts, but lacks an acidic hydrogen; these solvents generally have intermediate to high dielectric constants and polarity. Non-limiting examples of polar aprotic solvents include acetone, acetonitrile, dichloromethane (DCM), dimethyl sulfoxide (DMSO), ethyl acetate, hexamethylphosphoric triamide (HMPT), N,N-dimethylformamide (DMF), and tetrahydrofuran (THF).

As used herein, a nonpolar aprotic solvent is a solvent that will dissolve many salts, but lacks an acidic hydrogen; these solvents generally have low dielectric constants and polarity. Non-limiting examples of nonpolar aprotic solvents include benzene, chloroform, cyclohexane, diethyl ether, hexane, pentane, and toluene.

Compounds of the Invention
An aspect of the invention is a compound, represented by

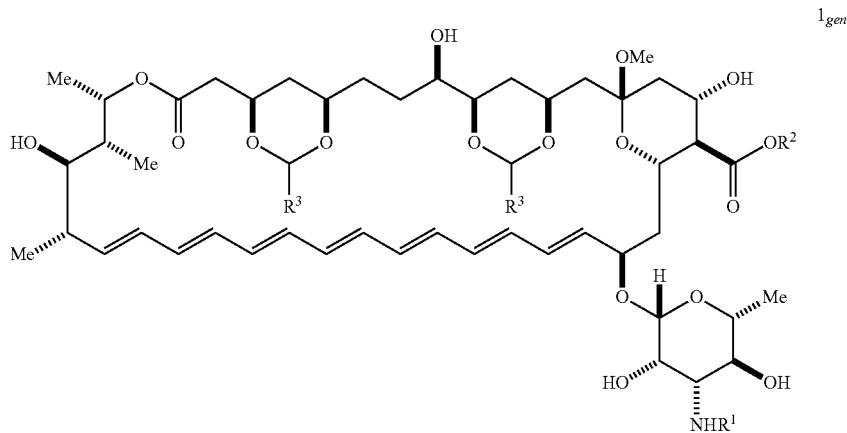

$1_{gen}$ wherein, independently for each occurrence,
$R^1$ is $C(O)OR^a$;
$R^2$ is selected from the group consisting of 2-alken-1-yl, benzyl, and $(R^b)_3Si$—;
$R^3$ is substituted or unsubstituted aryl, or $C_1$-$C_6$ alkyl;
$R^a$ is selected from the group consisting of 2-alken-1-yl, tert-butyl, and benzyl; and
$R^b$ is substituted or unsubstituted aryl, or $C_1$-$C_6$ alkyl.

In certain embodiments, $R^a$ is 2-alken-1-yl.
In certain embodiments, $R^2$ is 2-alken-1-yl.
In certain embodiments, $R^3$ is substituted or unsubstituted aryl.
In certain embodiments, $R^a$ is 2-alken-1-yl; $R^2$ is 2-alken-1-yl; and $R^3$ is substituted or unsubstituted aryl.
In certain embodiments, $R^a$ is 2-propen-1-yl.
In certain embodiments, $R^2$ is 2-propen-1-yl.
In certain embodiments, $R^3$ is para-methoxyphenyl (PMP).

In an embodiment, the compound is represented by

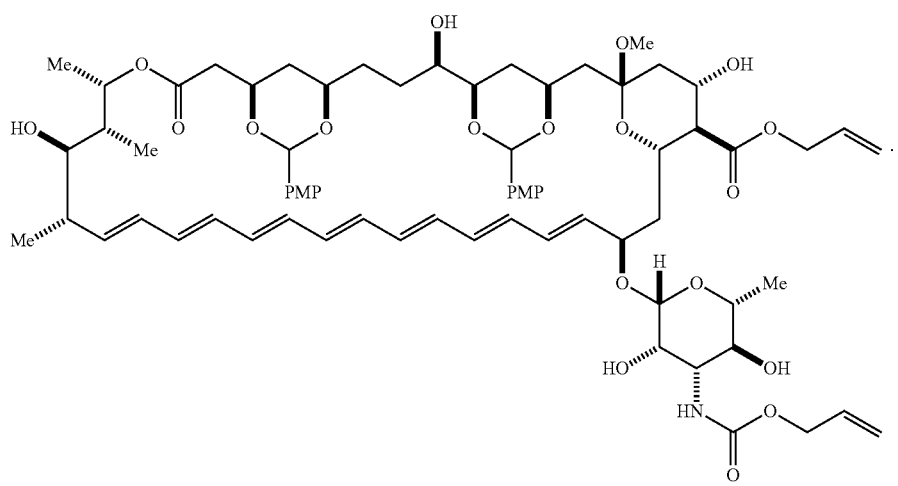

1

An aspect of the invention is a compound, represented by

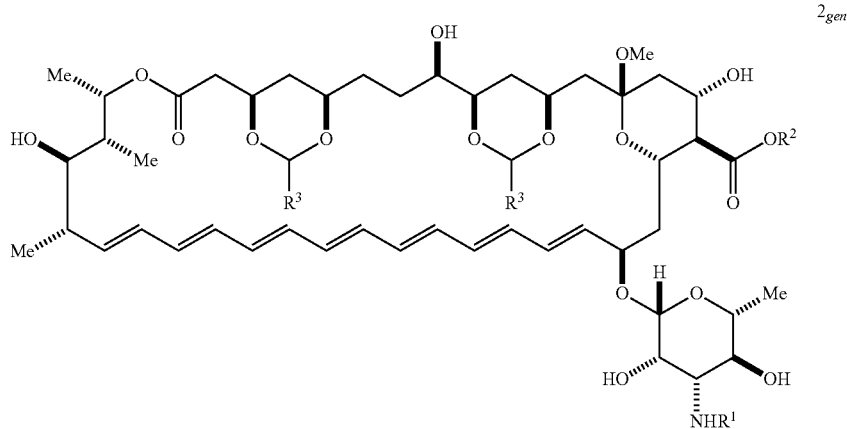

$2_{gen}$ wherein, independently for each occurrence,
$R^1$ is C(O)OR$^a$;
$R^2$ is selected from the group consisting of 2-alken-1-yl, benzyl, and (R$^b$)$_3$Si—;
$R^3$ is substituted or unsubstituted aryl, or $C_1$-$C_6$ alkyl;
$R^4$ is —C(O)R$^c$;
$R^a$ is selected from the group consisting of 2-alken-1-yl, tert-butyl, and benzyl;
$R^b$ is substituted or unsubstituted aryl, or $C_1$-$C_6$ alkyl; and
$R^c$ is substituted or unsubstituted aryl.
In certain embodiments, $R^a$ is 2-alken-1-yl.
In certain embodiments, $R^2$ is 2-alken-1-yl.
In certain embodiments, $R^3$ is substituted or unsubstituted aryl.
In certain embodiments, $R^c$ is substituted or unsubstituted phenyl.
In certain embodiments, $R^a$ is 2-alken-1-yl; $R^2$ is 2-alken-1-yl; $R^3$ is substituted or unsubstituted aryl; and $R^c$ is substituted or unsubstituted phenyl.
In certain embodiments, $R^a$ is 2-propen-1-yl.
In certain embodiments, $R^2$ is 2-propen-1-yl.
In certain embodiments, $R^3$ is para-methoxyphenyl (PMP).
In certain embodiments, $R^4$ is p-(tert-butyl)benzoyl.
In an embodiment, the compound is represented by

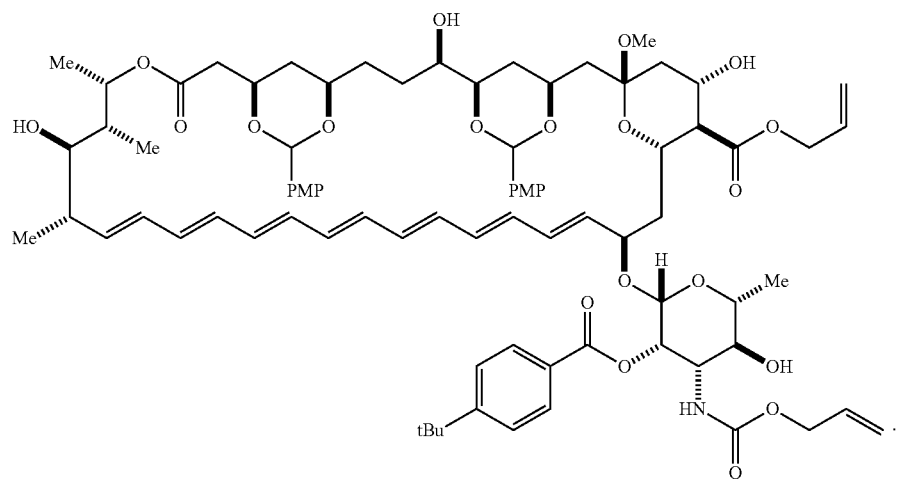

2

An aspect of the invention is a compound, represented by

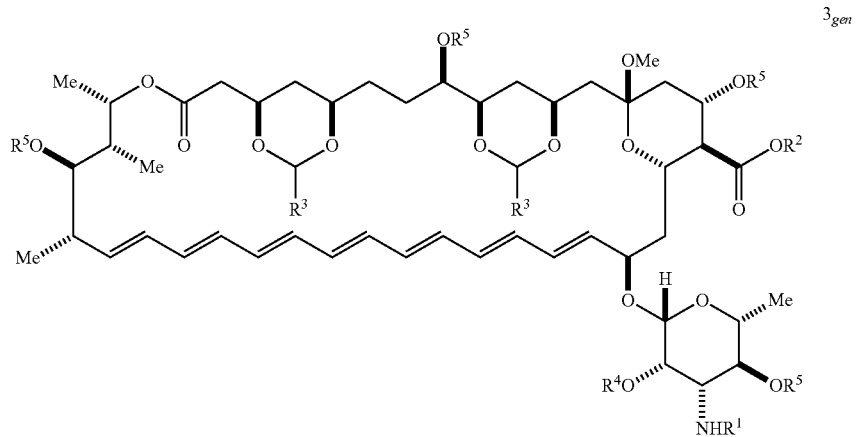

$3_{gen}$ wherein, independently for each occurrence,
$R^1$ is $C(O)OR^a$;
$R^2$ is selected from the group consisting of 2-alken-1-yl, benzyl, and $(R^b)_3Si-$;
$R^3$ is substituted or unsubstituted aryl, or $C_1$-$C_6$ alkyl;
$R^4$ is $-C(O)R^c$;
$R^5$ is $(R^b)_3Si-$;
$R^a$ is selected from the group consisting of 2-alken-1-yl, tert-butyl, and benzyl;
$R^b$ is substituted or unsubstituted aryl, or $C_1$-$C_6$ alkyl; and
$R^c$ is substituted or unsubstituted aryl.
In certain embodiments, $R^a$ is 2-alken-1-yl.
In certain embodiments, $R^2$ is 2-alken-1-yl.
In certain embodiments, $R^3$ is substituted or unsubstituted aryl.

In certain embodiments, $R^c$ is substituted or unsubstituted phenyl.
In certain embodiments, $R^b$ is $C_1$-$C_6$ alkyl.
In certain embodiments, $R^a$ is 2-alken-1-yl; $R^2$ is 2-alken-1-yl; $R^3$ is substituted or unsubstituted aryl; $R^c$ is substituted or unsubstituted phenyl; and $R^b$ is $C_1$-$C_6$ alkyl.
In certain embodiments, $R^a$ is 2-propen-1-yl.
In certain embodiments, $R^2$ is 2-propen-1-yl.
In certain embodiments, $R^3$ is para-methoxyphenyl (PMP).
In certain embodiments, $R^4$ is p-(tert-butyl)benzoyl.
In certain embodiments, $R^5$ is diethylisopropylsilyl.
In an embodiment, the compound is represented by

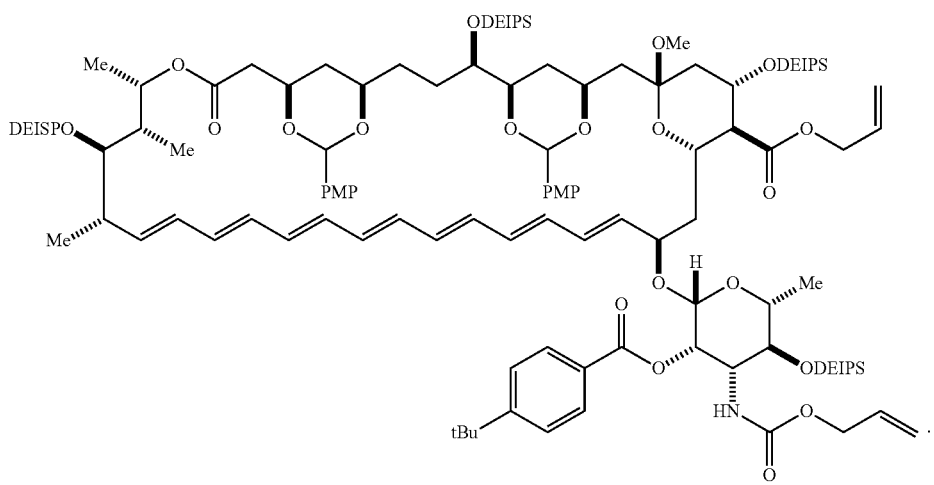

3

An aspect of the invention is a compound, represented by

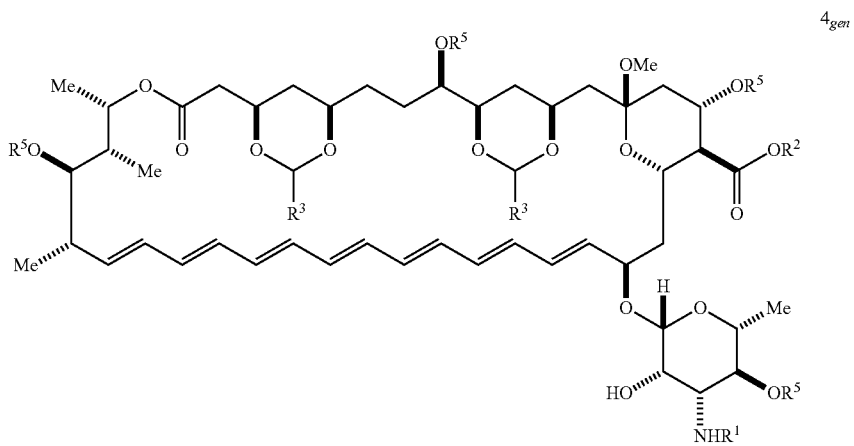

$4_{gen}$ wherein, independently for each occurrence,
R$^1$ is C(O)OR$^a$;
R$^2$ is selected from the group consisting of 2-alken-1-yl, benzyl, and (R$^b$)$_3$Si—;
R$^3$ is substituted or unsubstituted aryl, or C$_1$-C$_6$ alkyl;
R$^5$ is (R$^b$)$_3$Si—;
R$^a$ is selected from the group consisting of 2-alken-1-yl, tert-butyl, and benzyl; and
R$^b$ is substituted or unsubstituted aryl, or C$_1$-C$_6$ alkyl.
In certain embodiments, R$^a$ is 2-alken-1-yl.
In certain embodiments, R$^2$ is 2-alken-1-yl.

In certain embodiments, R$^3$ is substituted or unsubstituted aryl.
In certain embodiments, R$^b$ is C$_1$-C$_6$ alkyl.
In certain embodiments, R$^a$ is 2-alken-1-yl; R$^2$ is 2-alken-1-yl; R$^3$ is substituted or unsubstituted aryl; and R$^b$ is C$_1$-C$_6$ alkyl.
In certain embodiments, R$^a$ is 2-propen-1-yl.
In certain embodiments, R$^2$ is 2-propen-1-yl.
In certain embodiments, R$^3$ is para-methoxyphenyl (PMP).
In certain embodiments, R$^5$ is diethylisopropylsilyl.
In an embodiment, the compound is represented by

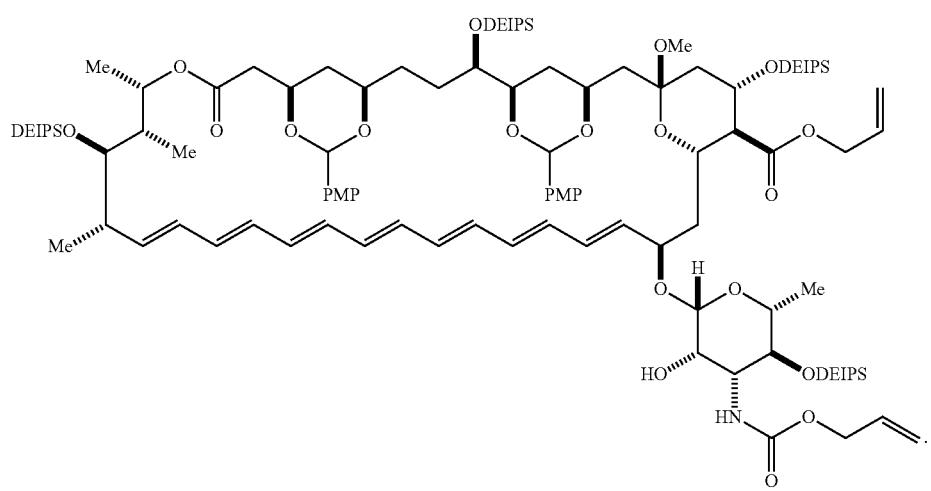

4

An aspect of the invention is a compound, represented by

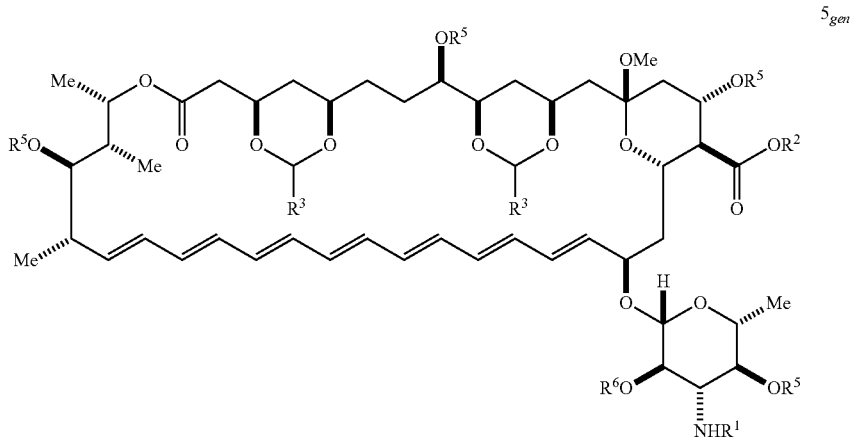

wherein, independently for each occurrence,
R$^1$ is C(O)OR$^a$;
R$^2$ is selected from the group consisting of 2-alken-1-yl, benzyl, and (R$^b$)$_3$Si—;
R$^3$ is substituted or unsubstituted aryl, or C$_1$-C$_6$ alkyl;
R$^5$ is (R$^b$)$_3$Si—;
R$^6$ is —C(O)R$^c$;
R$^a$ is selected from the group consisting of 2-alken-1-yl, tert-butyl, and benzyl;
R$^b$ is substituted or unsubstituted aryl, or C$_1$-C$_6$ alkyl; and
R$^c$ is substituted or unsubstituted aryl.
In certain embodiments, R$^a$ is 2-alken-1-yl.
In certain embodiments, R$^2$ is 2-alken-1-yl.
In certain embodiments, R$^3$ is substituted or unsubstituted aryl.

In certain embodiments, R$^c$ is substituted or unsubstituted phenyl.
In certain embodiments, R$^b$ is C$_1$-C$_6$ alkyl.
In certain embodiments, R$^a$ is 2-alken-1-yl; R$^2$ is 2-alken-1-yl; R$^3$ is substituted or unsubstituted aryl; R$^c$ is substituted or unsubstituted phenyl; and R$^b$ is C$_1$-C$_6$ alkyl.
In certain embodiments, R$^a$ is 2-propen-1-yl.
In certain embodiments, herein R$^2$ is 2-propen-1-yl.
In certain embodiments, R$^3$ is para-methoxyphenyl (PMP).
In certain embodiments, R$^6$ is p-nitrobenzoyl.
In certain embodiments, R$^5$ is diethylisopropylsilyl.
In an embodiment, the compound is represented by

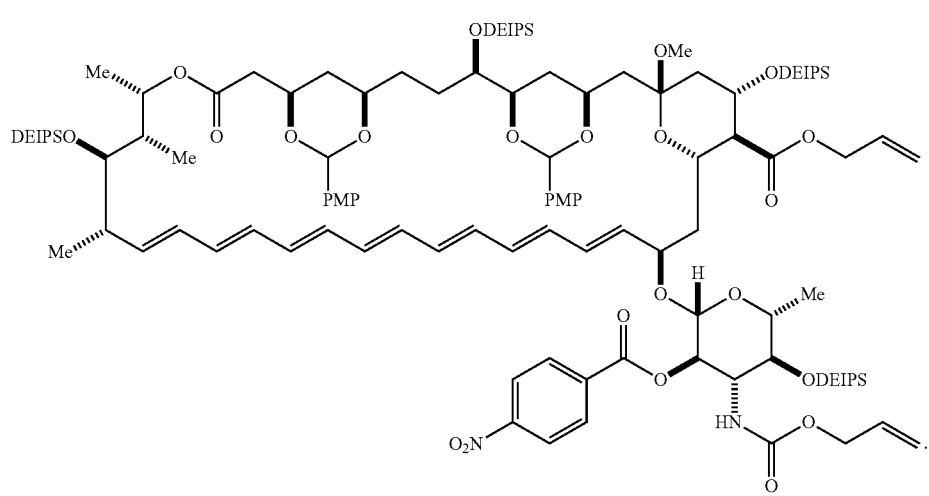

An aspect of the invention is a compound, represented by

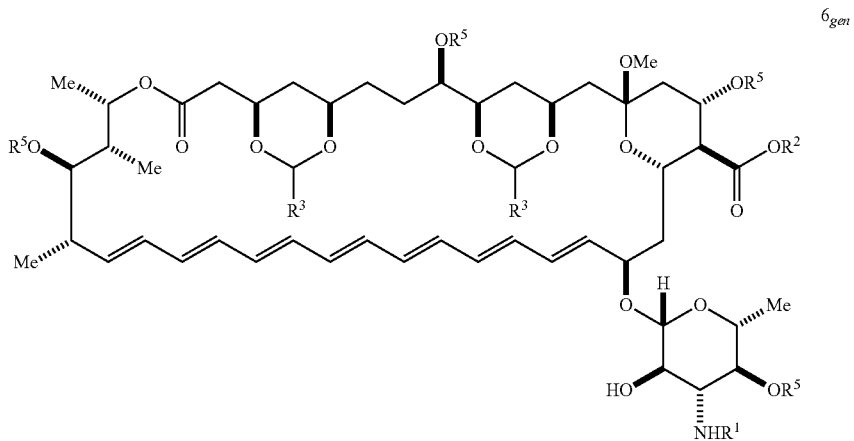

6_gen wherein, independently for each occurrence,
$R^1$ is $C(O)OR^a$;
$R^2$ is selected from the group consisting of 2-alken-1-yl, benzyl, and $(R^b)_3Si-$;
$R^3$ is substituted or unsubstituted aryl, or $C_1$-$C_6$ alkyl;
$R^5$ is $(R^b)_3Si-$;
$R^a$ is selected from the group consisting of 2-alken-1-yl, tert-butyl, and benzyl; and
$R^b$ is substituted or unsubstituted aryl, or $C_1$-$C_6$ alkyl.
In certain embodiments, $R^a$ is 2-alken-1-yl.
In certain embodiments, $R^2$ is 2-alken-1-yl.

In certain embodiments, $R^3$ is substituted or unsubstituted aryl.
In certain embodiments, $R^b$ is $C_1$-$C_6$ alkyl.
In certain embodiments, $R^a$ is 2-alken-1-yl; $R^2$ is 2-alken-1-yl; $R^3$ is substituted or unsubstituted aryl; and $R^b$ is $C_1$-$C_6$ alkyl.
In certain embodiments, $R^a$ is 2-propen-1-yl.
In certain embodiments, $R^2$ is 2-propen-1-yl.
In certain embodiments, $R^3$ is para-methoxyphenyl (PMP).
In certain embodiments, $R^5$ is diethylisopropylsilyl.
In an embodiment, the compound is represented by

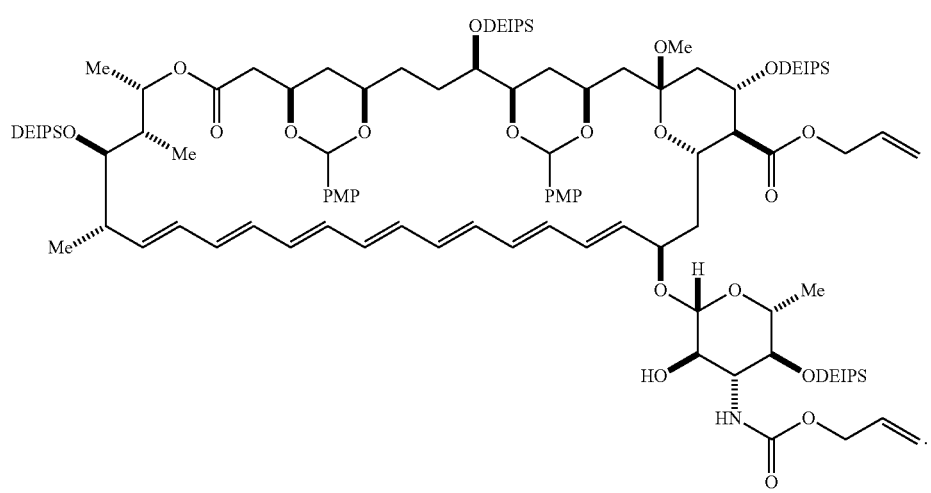

6

An aspect of the invention is a compound, represented by

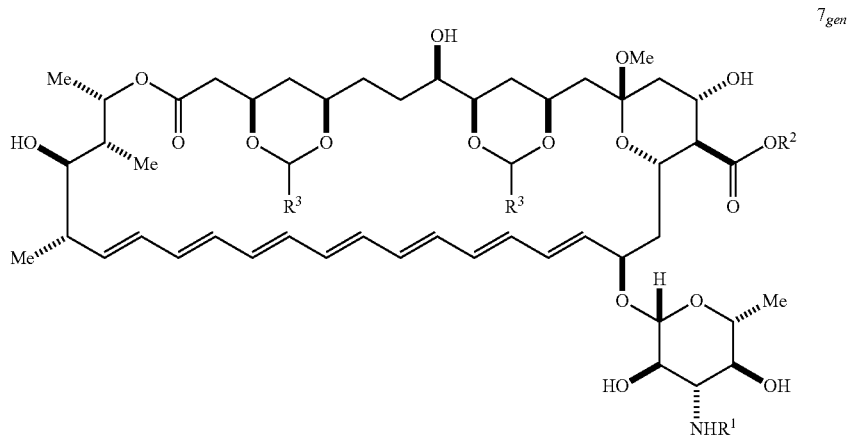

7<sub>gen</sub> wherein, independently for each occurrence,
R$^1$ is C(O)OR$^a$;
R$^2$ is selected from the group consisting of 2-alken-1-yl, benzyl, and (R$^b$)$_3$Si—;
R$^3$ is substituted or unsubstituted aryl, or C$_1$-C$_6$ alkyl;
R$^a$ is selected from the group consisting of 2-alken-1-yl, tert-butyl, and benzyl; and
R$^b$ is substituted or unsubstituted aryl, or C$_1$-C$_6$ alkyl.
In certain embodiments, R$^a$ is 2-alken-1-yl.
In certain embodiments, R$^2$ is 2-alken-1-yl.
In certain embodiments, R$^3$ is substituted or unsubstituted aryl.
In certain embodiments, R$^a$ is 2-alken-1-yl; R$^2$ is 2-alken-1-yl; and R$^3$ is substituted or unsubstituted aryl.
In certain embodiments, R$^a$ is 2-propen-1-yl.
In certain embodiments, R$^2$ is 2-propen-1-yl.
In certain embodiments, R$^3$ is para-methoxyphenyl (PMP).
In an embodiment, the compound is represented by

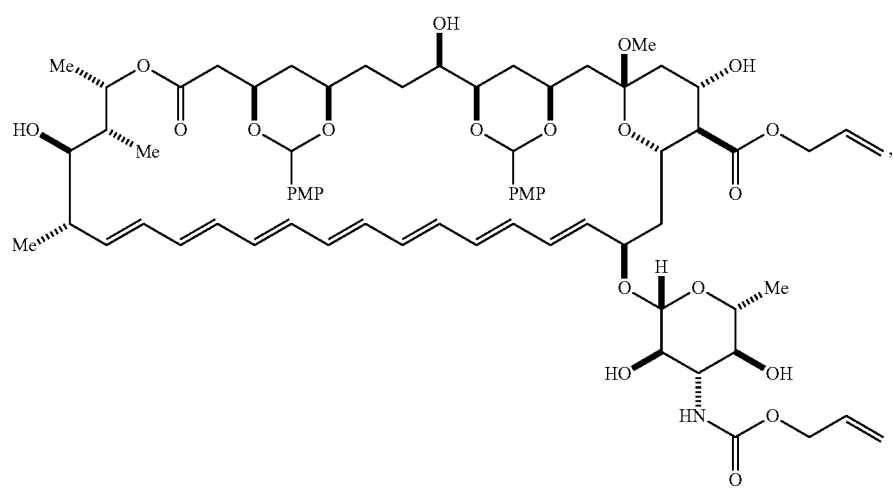

7

An aspect of the invention is a compound, represented by
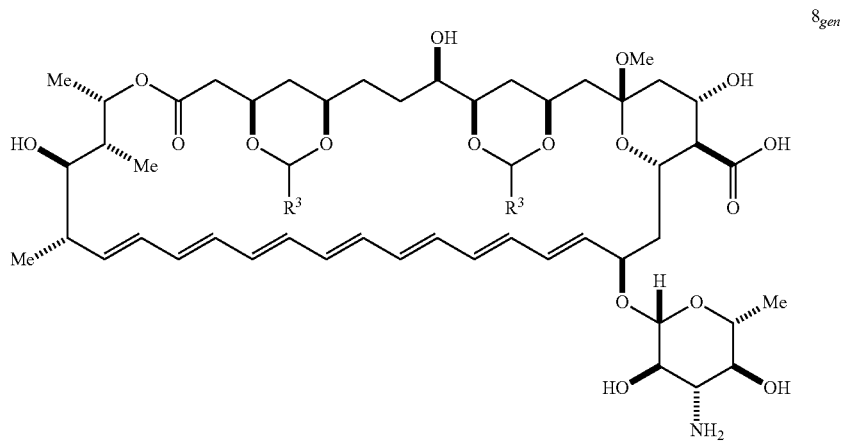
8_gen
wherein, independently for each occurrence,
R³ is substituted or unsubstituted aryl, or $C_1$-$C_6$ alkyl.
In certain embodiments, R³ is substituted or unsubstituted aryl.
In an embodiment, the compound is represented by
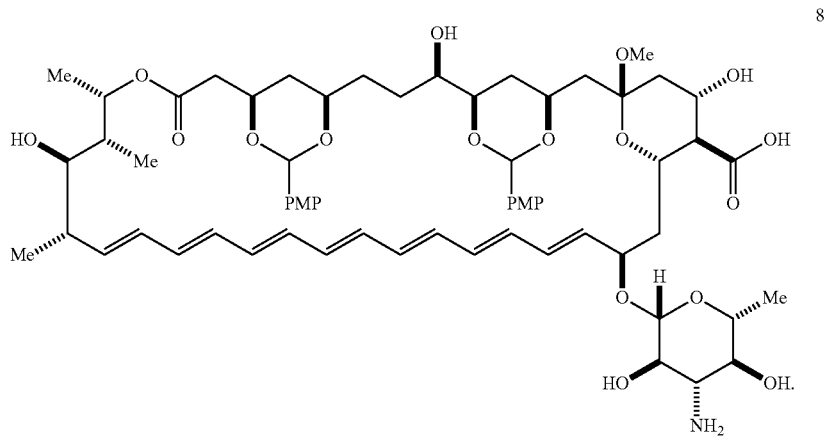
8

An aspect of the invention is a compound represented by
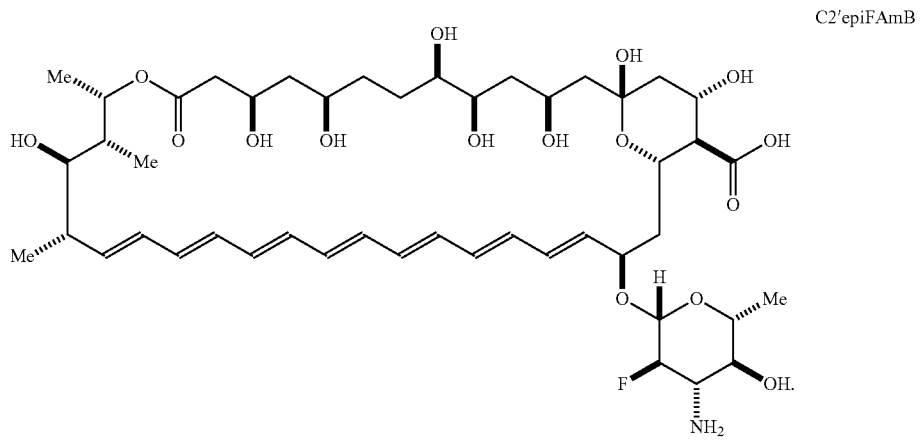
Methods of the Invention
An aspect of the invention is a method of making 2'-epi-AmB
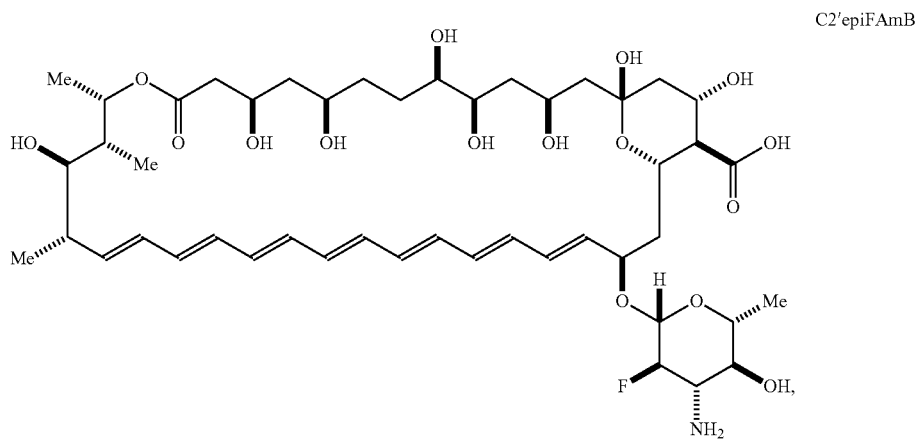
45
comprising the step of:
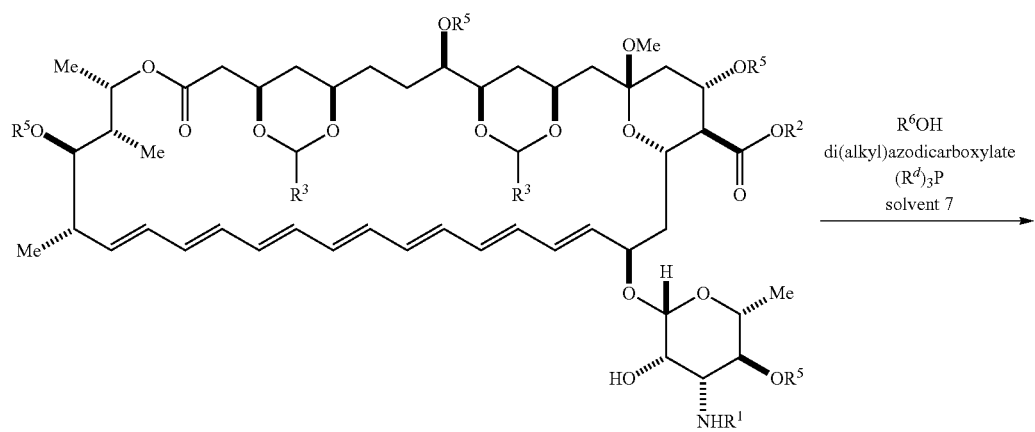

-continued

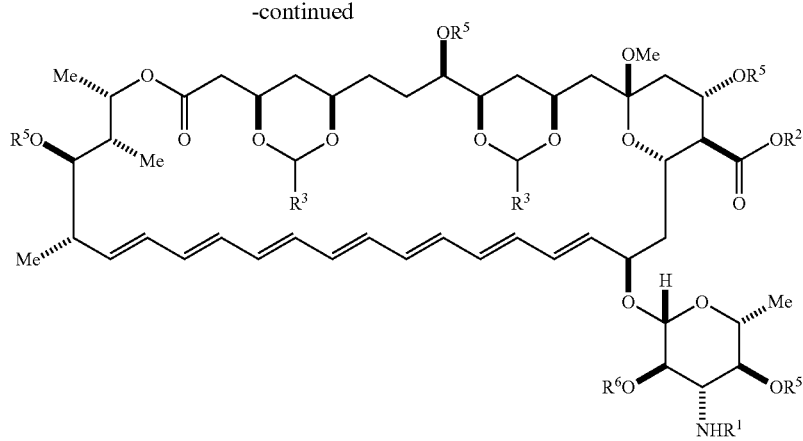

5_gen wherein, independently for each occurrence,
$R^1$ is $C(O)OR^a$;
$R^2$ is selected from the group consisting of 2-alken-1-yl, benzyl, and $(R^b)_3Si—$;
$R^3$ is substituted or unsubstituted aryl, or $C_1$-$C_6$ alkyl;
$R^5$ is $(R^b)_3Si—$;
$R^6$ is $—C(O)R^c$;
$R^a$ is selected from the group consisting of 2-alken-1-yl, tert-butyl, and benzyl;
$R^b$ is substituted or unsubstituted aryl, or $C_1$-$C_6$ alkyl;
$R^c$ is substituted or unsubstituted aryl;
$R^d$ is $C_1$-$C_6$ alkyl or aryl; and
solvent 7 is a nonpolar aprotic solvent.

In certain embodiments, $R^6$ is substituted aryloyl.
In certain embodiments, $R^d$ is aryl.
In certain embodiments, $R^6$ is substituted aryloyl; and $R^d$ is aryl.
In certain embodiments, $R^6$ is para-nitrobenzoyl.
In certain embodiments, in $R^d$ is phenyl.

In certain embodiments, solvent 7 is benzene.

In certain embodiments, di(alkyl)azodicarboxylate is di(isopropyl)azodicarboxylate (DIAD) or di(ethyl)azodicarboxylate (DEAD).

In certain embodiments, $R^6$ is para-nitrobenzoyl; di(alkyl)azodicarboxylate is di(isopropyl)azodicarboxylate (DIAD); and $R^d$ is phenyl.

In certain embodiments, $R^6$ is para-nitrobenzoyl; di(alkyl)azodicarboxylate is di(isopropyl)azodicarboxylate (DIAD); $R^d$ is phenyl; and solvent 7 is benzene.

In an embodiment, $R^a$ is 2-propen-1-yl; $R^2$ is 2-propen-1-yl; $R^3$ is para-methoxyphenyl (PMP); $R^5$ is diethylisopropylsilyl; $R^6$ is para-nitrobenzoyl; di(alkyl)azodicarboxylate is di(isopropyl)azodicarboxylate (DIAD); $R^d$ is phenyl; and solvent 7 is benzene In certain embodiments, the method in accordance with any one of the preceding embodiments further includes the step of:

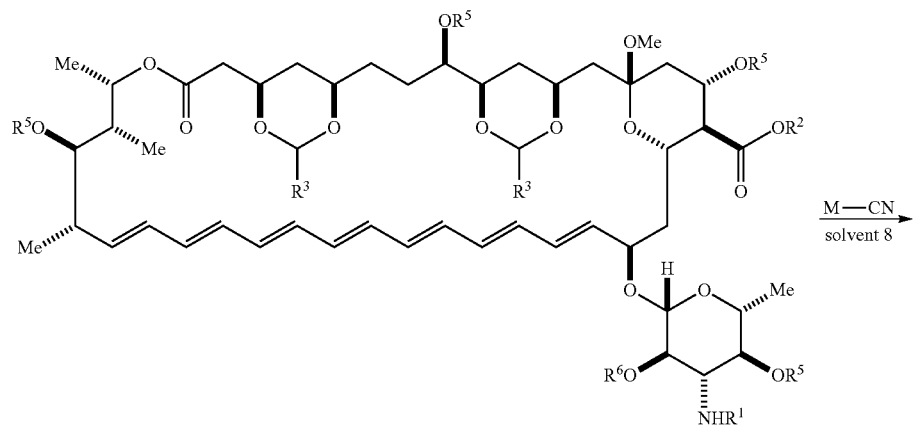

5_gen

-continued

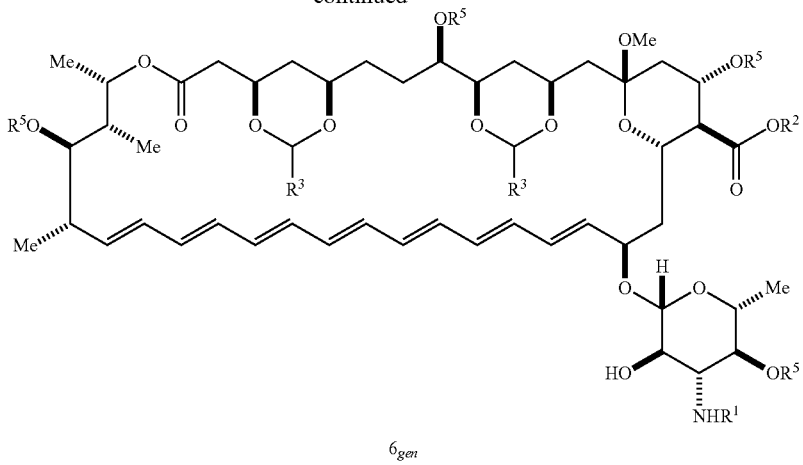

6_gen wherein

M is an alkali metal cation or alkaline earth metal cation; and solvent 8 is a polar aprotic solvent, a polar protic solvent, or a mixture thereof.

In certain embodiments, M is an alkali metal cation.

In certain embodiments, M is K.

In certain embodiments, solvent 8 is a mixture of tetrahydrofuran (THF) and MeOH.

In certain embodiments, M is K; and solvent 8 is a mixture of tetrahydrofuran (THF) and MeOH.

In an embodiment, $R^a$ is 2-propen-1-yl; $R^2$ is 2-propen-1-yl; $R^3$ is para-methoxyphenyl (PMP); $R^5$ is diethylisopropylsilyl; $R^6$ is para-nitrobenzoyl; M is K; and solvent 8 is a mixture of tetrahydrofuran (THF) and MeOH.

In certain embodiments, the method in accordance with any one of the preceding embodiments further includes the step of:

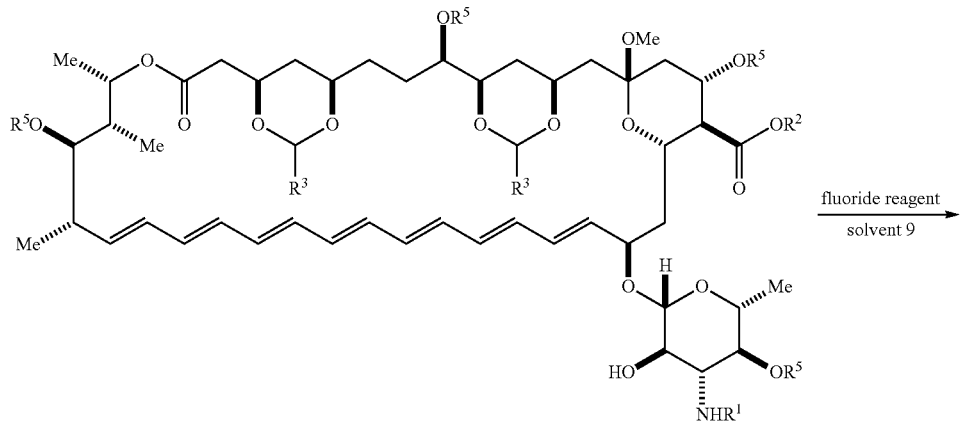

6_gen

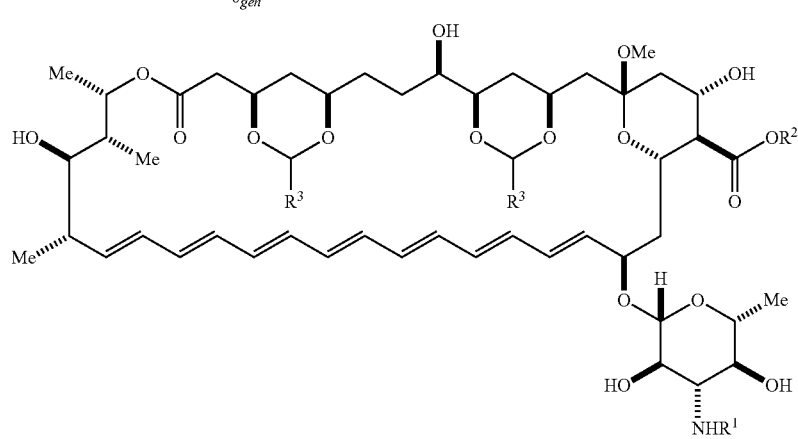

7_gen wherein fluoride reagent is selected from the group consisting of tetraalkylammonium fluoride and fluoride salts; and solvent 9 is a polar aprotic solvent, a polar protic solvent, or a mixture thereof.

In certain embodiments, fluoride reagent is a fluoride salt.

In certain embodiments, fluoride reagent is hydrogen fluoride pyridine.

In certain embodiments, solvent 9 is tetrahydrofuran (THF).

In certain embodiments, fluoride reagent is hydrogen fluoride pyridine; and solvent 9 is tetrahydrofuran (THF).

In an embodiment, $R^a$ is 2-propen-1-yl; $R^2$ is 2-propen-1-yl; $R^3$ is para-methoxyphenyl (PMP); $R^5$ is diethylisopropylsilyl; fluoride reagent is hydrogen fluoride pyridine; and solvent 9 is tetrahydrofuran (THF).

In certain embodiments, the method in accordance with any one of the preceding embodiments further includes the step of:

solvent 10 is a polar aprotic solvent.

In certain embodiments, Pd reagent is Pd(0).

In certain embodiments, $R^e$ is aryl.

In certain embodiments, $R^f$ is aryl.

In certain embodiments, said $R^f CO_2 H$ or 1,3-diketone is $R^f CO_2 H$.

In certain embodiments, Pd reagent is Pd(0); $R^e$ is aryl; $R^f$ is aryl; and said $R^f CO_2 H$ or 1,3-diketone is $R^f CO_2 H$.

In certain embodiments, ligand is $(PPh_3)_4$.

In certain embodiments, said $R^f CO_2 H$ or 1,3-diketone is thiosalicylic acid.

In certain embodiments, solvent 10 is dimethylformamide (DMF).

In certain embodiments, Pd reagent is Pd(0); ligand is $(PPh_3)_4$; and said $R^f CO_2 H$ or 1,3-diketone is thiosalicylic acid.

In certain embodiments, Pd reagent is Pd(0); ligand is $(PPh_3)_4$; said $R^f CO_2 H$ or 1,3-diketone is thiosalicylic acid; and solvent 10 is dimethylformamide (DMF).

In an embodiment, $R^a$ is 2-propen-1-yl; $R^2$ is 2-propen-1-yl; $R^3$ is para-methoxyphenyl (PMP); Pd reagent is Pd(0);

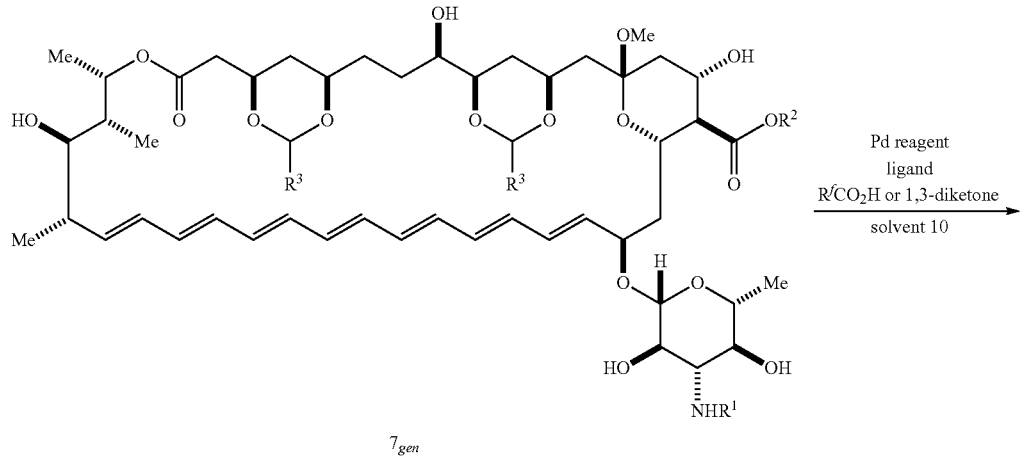

7$_{gen}$

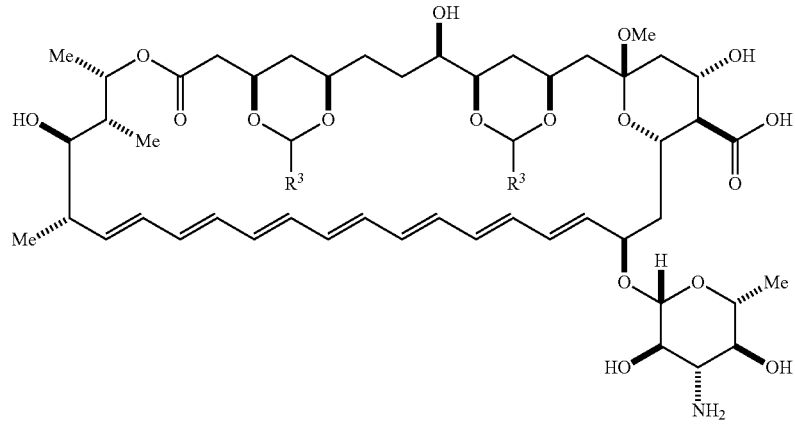

8$_{gen}$ wherein, independently for each occurrence,

Pd reagent is Pd(0) or Pd(II);

ligand is $(R^e)_3 P$;

$R^e$ is $C_1$-$C_6$ alkyl or aryl;

$R^f$ is $C_1$-$C_6$ alkyl or aryl; and ligand is $(PPh_3)_4$; said $R^f CO_2 H$ or 1,3-diketone is thiosalicylic acid; and solvent 10 is dimethylformamide (DMF).

In certain embodiments, the method in accordance with any one of the preceding embodiments further includes the step of:

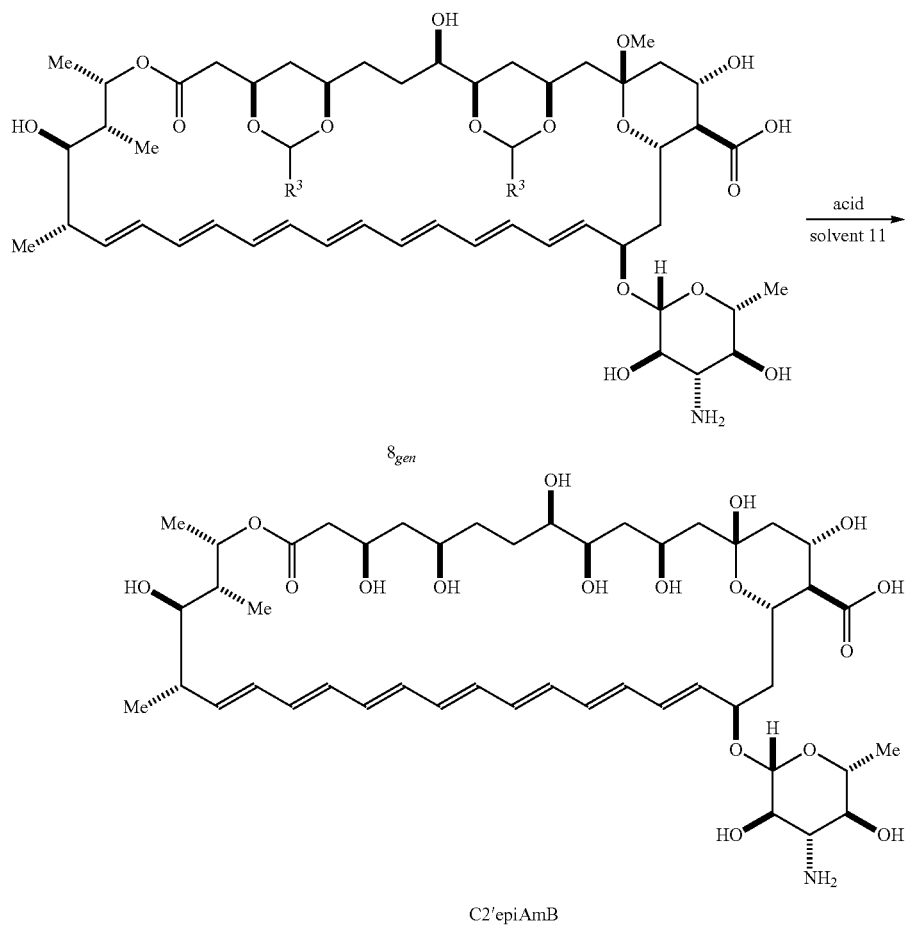

8_gen

C2'epiAmB wherein acid is a Bronsted acid; and solvent 11 is a mixture of water and a polar aprotic solvent.

In certain embodiments, acid is camphorsulfonic acid (CSA).

In certain embodiments, solvent 11 is a mixture of water and MeCN.

In certain embodiments, acid is camphorsulfonic acid (CSA); and solvent 11 is a mixture of water and MeCN.

In an embodiment, $R^3$ is para-methoxyphenyl (PMP); acid is camphorsulfonic acid (CSA); and solvent 11 is a mixture of water and MeCN.

In certain embodiments, the method in accordance with any one of the preceding embodiments further includes the step of:

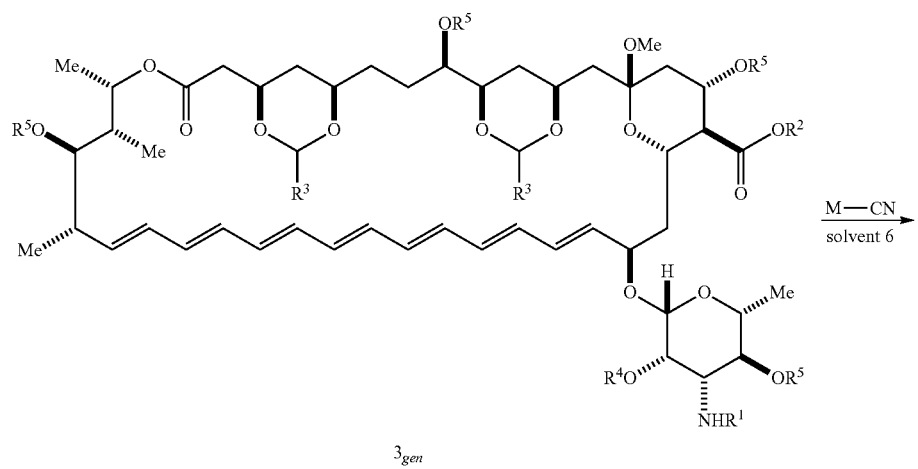

3_gen

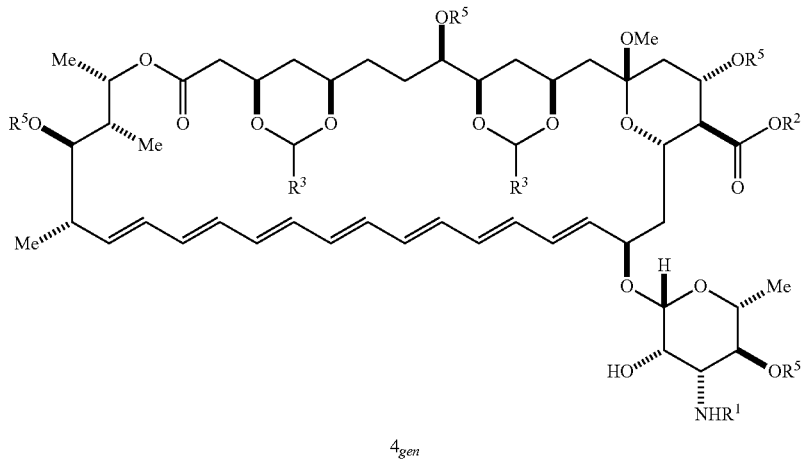

$4_{gen}$ wherein $R^4$ is —C(O)$R^c$;

M is an alkali metal cation or alkaline earth metal cation; and solvent 6 is a polar aprotic solvent, a polar protic solvent, or a mixture thereof.

In certain embodiments, M is an alkali metal cation.

In certain embodiments, solvent 6 is a mixture of a polar aprotic solvent and a polar protic solvent.

In certain embodiments, $R^4$ is p-(tert-butyl)benzoyl.

In certain embodiments, M is K.

In certain embodiments, $R^4$ is p-(tert-butyl)benzoyl; and M is K.

In certain embodiments, solvent 6 is a mixture of tetrahydrofuran (THF) and MeOH.

In certain embodiments, $R^4$ is p-(tert-butyl)benzoyl; M is K; and solvent 6 is a mixture of tetrahydrofuran (THF) and MeOH.

In an embodiment, $R^a$ is 2-propen-1-yl; $R^2$ is 2-propen-1-yl; $R^3$ is para-methoxyphenyl (PMP); $R^4$ is p-(tert-butyl)benzoyl; M is K; and solvent 6 is a mixture of tetrahydrofuran (THF) and MeOH.

In certain embodiments, the method in accordance with any one of the preceding embodiments further includes the step of:

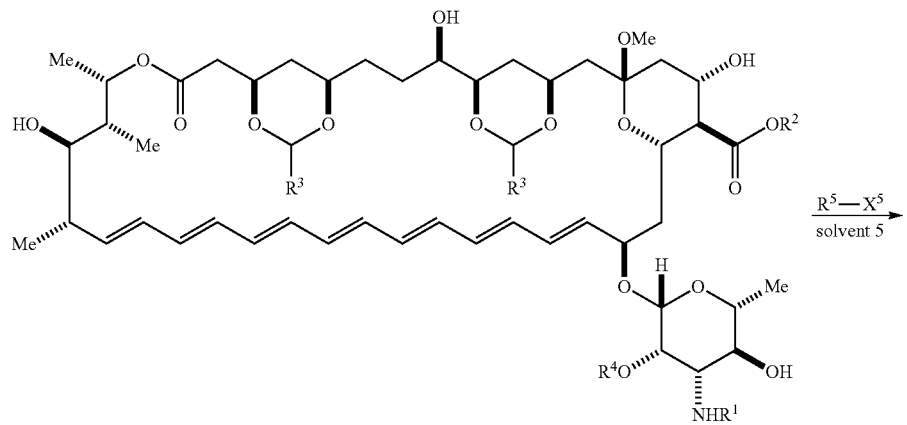

$2_{gen}$

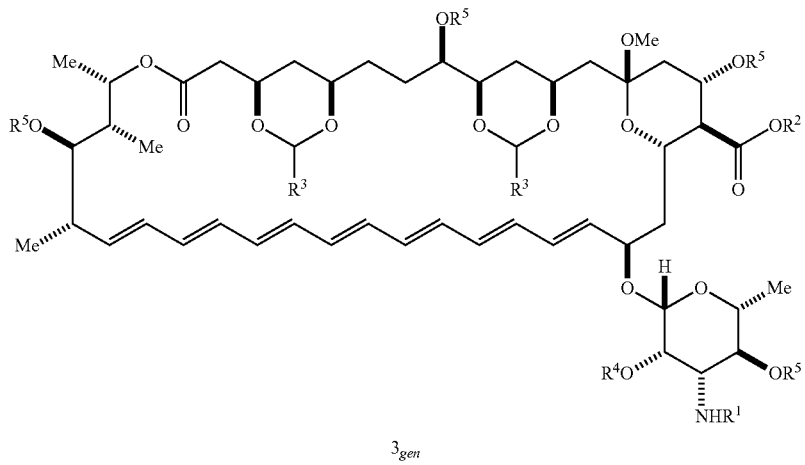

3_gen wherein

X⁵ is halide or sulfonate; and solvent 5 is a polar aprotic solvent, a nonpolar aprotic solvent, or a mixture thereof.

In certain embodiments, $R^b$ is $C_1$-$C_6$ alkyl.

In certain embodiments, X⁵ is sulfonate.

In certain embodiments, $R^b$ is $C_1$-$C_6$ alkyl; and X⁵ is sulfonate.

In certain embodiments, solvent 5 is a mixture of a polar aprotic solvent and a nonpolar aprotic solvent.

In certain embodiments, solvent 5 is a mixture of dichloromethane (DCM) and hexanes.

In certain embodiments, R⁵—X⁵ is diethyl(isopropyl)silyl trifluoromethanesulfonate.

In certain embodiments, R⁵—X⁵ is diethyl(isopropyl)silyl trifluoromethanesulfonate; and solvent 5 is a mixture of dichloromethane (DCM) and hexanes.

In an embodiment, $R^a$ is 2-propen-1-yl; R² is 2-propen-1-yl; R³ is para-methoxyphenyl (PMP); R⁴ is p-(tert-butyl)benzoyl; R⁵—X⁵ is diethyl(isopropyl)silyl trifluoromethanesulfonate; and solvent 5 is a mixture of dichloromethane (DCM) and hexanes.

In certain embodiments, the method in accordance with any one of the preceding embodiments further includes the step of:

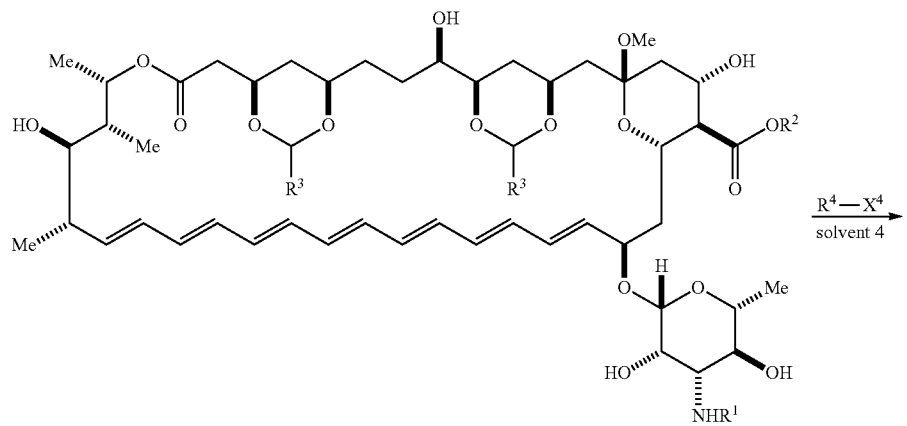

1_gen

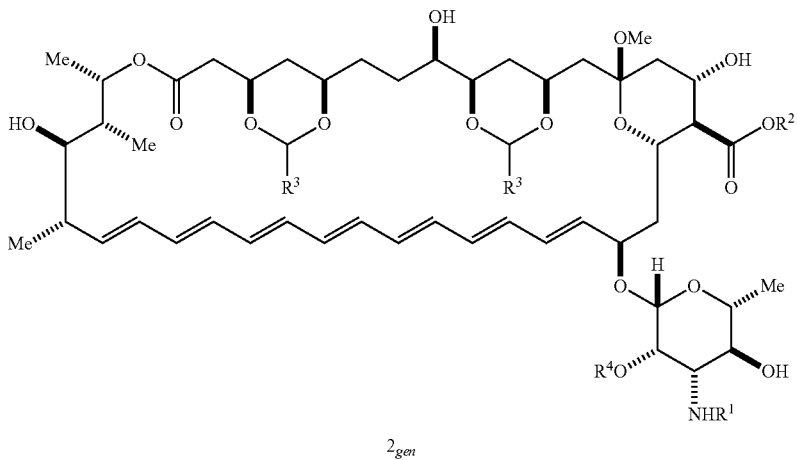

2<sub>gen</sub> wherein

R⁴ is substituted or unsubstituted aryloyl; and

X⁴ is selected from the group consisting of halide, succinimidyl, hydroxysuccinimidyl, azide, alkenoxyl, and aryloxyl; and solvent 4 is a polar aprotic solvent.

In certain embodiments, R⁴ is substituted aryloyl.

In certain embodiments, X⁴ is halide.

In certain embodiments, R⁴ is substituted phenyl; and X⁴ is halide.

In certain embodiments, R⁴—X⁴ is p-(tert-butyl)benzoyl chloride.

In certain embodiments, solvent 4 is tetrahydrofuran (THF).

In certain embodiments, R⁴—X⁴ is p-(tert-butyl)benzoyl chloride; and solvent 4 is tetrahydrofuran (THF).

In an embodiment, $R^a$ is 2-propen-1-yl; $R^2$ is 2-propen-1-yl; $R^3$ is para-methoxyphenyl (PMP); $R^4$ is p-(tert-butyl)benzoyl; $R^4$—$X^4$ is p-(tert-butyl)benzoyl chloride; and solvent 4 is tetrahydrofuran (THF).

In certain embodiments, the method in accordance with any one of the preceding embodiments further includes the step of:

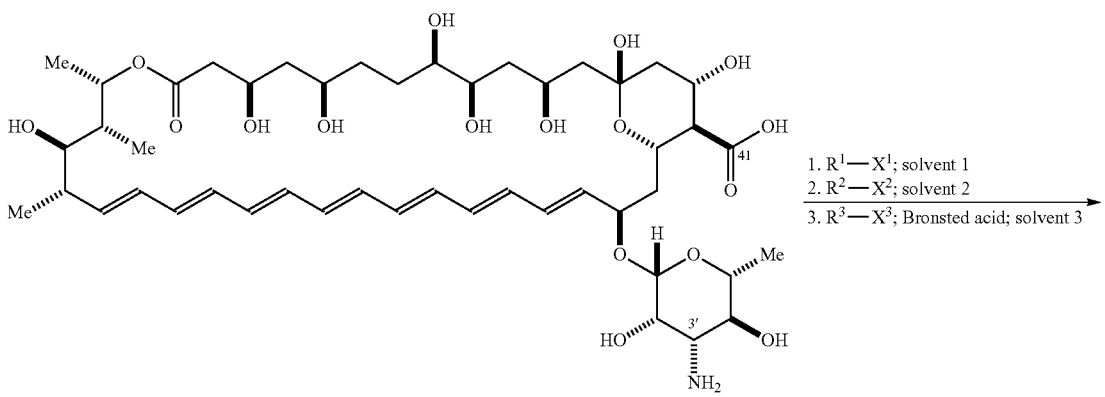

AmB

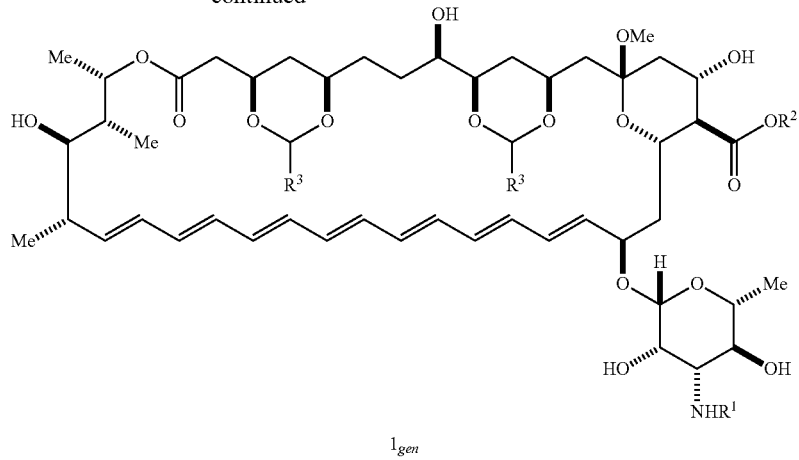

1_gen wherein
X¹ is halide or sulfonate;
X² is selected from the group consisting of halide, succinimidyl, hydroxysuccinimidyl, azido, alkenoxyl, and aryloxyl;
X³ is —CH(OR)₂;
R is $C_1$-$C_6$ alkyl;
solvent 1 is a polar aprotic solvent, a polar protic solvent, or a mixture thereof;
solvent 2 is a polar aprotic solvent, a polar protic solvent, or a mixture thereof; and
solvent 3 is a polar aprotic solvent, a polar protic solvent, or a mixture thereof.
In certain embodiments, $R^a$ is 2-alken-1-yl.
In certain embodiments, $X^1$ is succinimidyl.
In certain embodiments, $R^a$ is 2-alken-1-yl; and $X^1$ is succinimidyl.
In certain embodiments, $R^2$ is 2-alken-1-yl.
In certain embodiments, $X^2$ is halide.
In certain embodiments, $R^2$ is 2-alken-1-yl; and $X^2$ is halide.
In certain embodiments, $R^3$ is substituted aryl.
In certain embodiments, $R^a$ is 2-propen-1-yl.
In certain embodiments, $R^2$ is 2-propen-1-yl.
In certain embodiments, $R^3$ is para-methoxyphenyl.
In certain embodiments, solvent 1 is a mixture of a polar aprotic solvent and a polar protic solvent.
In certain embodiments, solvent 2 is a mixture of a polar aprotic solvent and a polar protic solvent.
In certain embodiments, solvent 3 is a mixture of a polar aprotic solvent and a polar protic solvent.
In certain embodiments, solvent 1 is a mixture of dimethylformamide (DMF) and MeOH.
In certain embodiments, solvent 2 is a mixture of dimethylformamide (DMF) and MeOH.
In certain embodiments, solvent 3 is a mixture of tetrahydrofuran (THF) and MeOH.
In certain embodiments, Bronsted acid is camphorsulfonic acid (CSA).
In certain embodiments, $R^a$ is 2-propen-1-yl; $X^1$ is succinimidyl; $R^2$ is 2-propen-1-yl; $X^2$ is halide; and $R^3$ is para-methoxyphenyl.
In certain embodiments, $R^a$ is 2-propen-1-yl; $X^1$ is succinimidyl; $R^2$ is 2-propen-1-yl; $X^2$ is halide; $R^3$ is para-methoxyphenyl; solvent 1 is a mixture of dimethylformamide (DMF) and MeOH; solvent 2 is a mixture of DMF and MeOH; and solvent 3 is a mixture of tetrahydrofuran (THF) and MeOH.

In one embodiment, allyl esterification of the C41-carboxylate as the second step is achieved in a clean fashion under the given reaction conditions, as judged by analytical HPLC. Trituration with a 1:1 Et₂O:Hexane solution and rinsing with Et₂O followed by filtration most effectively removes the excess allylating reagent, providing an odorless free-flowing yellow powder. Previous syntheses installed the C41-allyl ester protecting group last, creating a situation where an aqueous work-up was necessary (non-polar AmB derivatives can't be crashed-out in non-polar solvents). Not protecting the C41-carboxylic acid resulted in complicated normal-phase flash chromatography purification for the prior steps.

In connection with the present invention, it was further discovered that the simultaneous installation of all three ketals in the third step can be efficiently carried out on multi-gram scale in a concentrated MeOH solution. It was surprisingly discovered that the best reaction time is very short (30 min) and allows for the cleanest conversion to product. Under normal MeOH:THF conditions, the reaction is longer with more decomposition and requires excessive equivalents of ketal reagent.

In order to effectively triturate the reaction after triethyl amine quenching, it was found that the concentrated MeOH solution must be diluted with THF to 0.03 M. This enables the formation of a fine yellow powder upon trituration into hexane. Once the semi-crude product is collected via filtration, it is then purified via normal-phase silica gel chromatography. It is noteworthy that in addition to obviating an aqueous extraction, the semi-crude dry, yellow powder can be stored for up to at least a month in the freezer under argon without significant decomposition. This allows for a focused stockpiling of the earlier stage material before transitioning to chromatography steps.

The inventors previously reported the C2' site-selective acylation of a different amphotericin B intermediate, but it was not clear whether the analogous site selectivity would be observed with this derivative having a very different collection of appended protecting groups. In the event, it was discovered that highly site-selective acylation of the C2' position of novel intermediate 1, proceeds with high efficiency and can be readily scaled. This reaction has been successfully run on 8 g scale.

In accordance with the invention, it was discovered that the first KCN-mediated selective hydrolysis of the C2'-benzoate intermediate 3 proceeds very efficiently and was successfully run on 6 g scale.

In accordance with the invention, also discovered were conditions that promote the conversion of 4 to 5 in excellent efficiency and in a scalable fashion. Mitsunobu conditions were optimized and successfully scaled-up to multi-gram scale from milligram scale. This was achieved by lowering the reaction temperature to 23° C. and by changing the solvent from toluene to benzene.

a single peak by analytical HPLC. Surprisingly, the reaction can be worked up by simple trituration with $Et_2O$, filtration and washing with excess $Et_2O$. Surprisingly, the semi-crude penultimate material can be taken on successfully to the final step without additional purification.

The final deprotection step was carried out on multi-hundred milligram and gram scale. By analytical HPLC, full consumption of the starting material and good conversion to the desired product is achieved.

An aspect of the invention is a method of making C2'epiFAmB

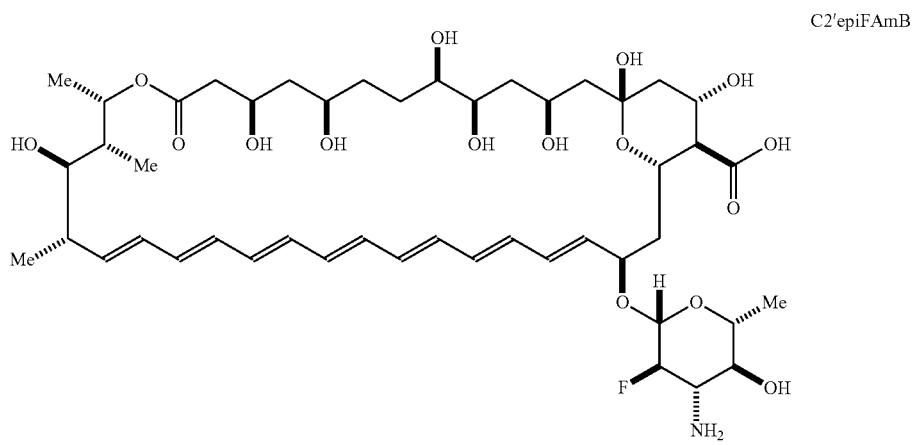

C2'epiFAmB

The second KCN-mediated selective hydrolysis of the C2'-nitrobenzoate 5 to yield 6 was surprisingly efficient and this reaction was successfully run on multi-gram scale. The reaction time was also reduced.

Surprisingly, both the C41-Allyl ester and C3'alloc carbamate survive all of the necessary chemistry steps. Notably, the C41-allyl ester is surprisingly unreactive to both KCN-mediated selective C2'-benzoate hydrolysis steps.

The final deprotection sequence was discovered to proceed with very few steps and HPLC purifications. In accordance with the invention, it was discovered that the ketals were much more readily cleaved if the C41 carboxylic acid and the C3' amine were unprotected. This discovery was harnessed to maximize the efficiency of the final deprotections sequence by performing these reactions in the following order:

1. HF-pyridine desilylation; then
2. Simultaneous removal of both C41-allyl ester and C3'-alloc carbamate; then
3. Global ketal hydrolysis.

HF-pyridine removal of the DEIPS groups cleanly generates the desired product along with a moderate amount of a mono-PMP ketalized product mixture. Both the product and the mono-PMP ketalized product mixture can be successfully chromatographed to purity via normal-phase flash chromatography. Furthermore, the mono-PMP ketalized mixture is successfully able to undergo the subsequent steps and successfully generate the desired final product.

Both C41-Allyl ester and C3'alloc carbamate are readily removed in a single step under identical palladium-mediated conditions. The zwitterionic product is generated cleanly as comprising the step of: combining $4_{gen}$ or a disclosed species thereof and a di(alkyl)azodicarboxylate, $(R^d)_3P$, a nucleophilic fluoride reagent, and solvent 7, thereby forming a variant of $5_{gen}$ or a disclosed species thereof in which a fluorine atom takes the place of $R^6O—$ in $5_{gen}$ or the disclosed species thereof. In other words, the method of making C2'epiFAmB is analogous to the methods described above in connection with making C2'epiAmB, except that a nucleophilic fluoride reagent (e.g., a tetraalkylammonium fluoride (e.g., TBAF), alkali metal fluoride (e.g., CsF or KF), alkaline earth fluoride, transition metal fluoride (e.g., AgF), diethylaminosulfur trifluoride (DAST), morpholinosulfur trifluoride, arylsulfur trifluoride, aminosulphur trifluoride, triethylamine trihydrofluoride, or HF/pyridine) is used in place of $R^6OH$ in the preparation of $5_{gen}$ from $4_{gen}$. The method of making C2'epiFAmB may further comprise any one of one or more of the other steps described above, either preceding or following the preparation of $5_{gen}$ from $4_{gen}$, in the methods of making C2'epiAmB.

EXAMPLES

Having now described the invention in detail, the same will be more clearly understood by reference to the following examples, which are included herewith for purposes of illustration only and are not intended to be limiting of the scope of the invention.

Example 1. Synthesis of Intermediate 1

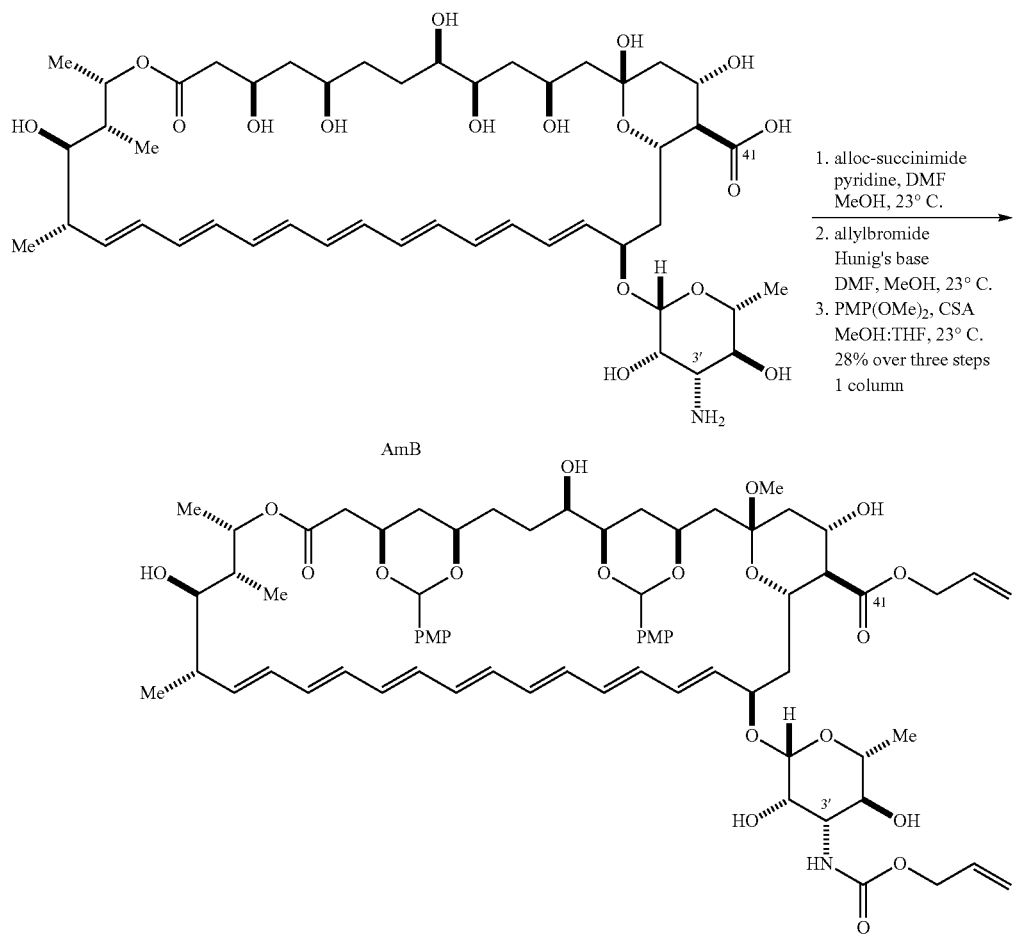

To a stirred suspension of AmB (4.0 g, 4.3 mmol, 1.0 equiv.) in DMF:MeOH (75 mL: 75 mL) in a 300 mL round bottom flask at 23° C. was added pyridine (5.0 mL, 50.0 mmol, 11.5 equiv.) and alloc-succinimide (2.4 g, 12.05 mmol, 2.8 equiv.). After stirring for 16 h at 23° C., the dark orange, homogeneous solution was slowly poured into rapidly stirring Et$_2$O (3.5 L). The yellow suspension was filtered through Whatman 42 filter paper (110 mm diameter) and washed with Et$_2$O (3×100 mL) before the cake was allowed to fully dry. The fully dried alloc-AmB yellow powder (4.3 mmol, quantitative) was taken on to the subsequent reaction without further purification.

To a stirred suspension of alloc-AmB (4.0 g, 4.3 mmol, 1.0 equiv.) in DMF:MeOH (10:1) in a 300 mL round bottom flask at 23° C. was added sequentially Hunig's base (3.75 mL, 21.5 mmol, 5.0 equiv.) and allyl bromide (11.2 mL, 129.0 mmol, 30 equiv.). After stirring for 8 h at 23° C., the dark orange, homogeneous solution was slowly poured into rapidly stirring Et$_2$O:Hex (1:1, 3.5 L). The subsequent yellow suspension was filtered through Whatman 42 filter paper (110 mm diameter) and washed with Et$_2$O (3×100 mL) before the cake was allowed to fully dry. The fully dried alloc-allylester-AmB (4.3 mmol, quantitative) was taken on to the subsequent reaction as a yellow powder without further purification.

To a stirred suspension of alloc-allylester-AmB (4.3 mmol, 1.0 equiv.) in MeOH (35 mL, 0.1 M) in a 300 mL round bottom flask at 23° C. was added anisaldehyde dimethylacetal (4.0 mL, 23.5 mmol, 5.5 equiv.) and stirred for 10 min until a very fine, uniform suspension formed. CSA (250 mg, 1.08 mmol, 0.25 equiv.) as a white crystalline solid was then added in one portion. After stirring at 23° C. for 30 min, Et$_3$N was added (~160 µL) followed by THF (81 mL to dilute down to 0.03M). The reaction was slowly poured into rapidly stirring hexane (3.5 L). The subsequent yellow suspension was filtered through Whatman 42 filter paper (110 mm diameter) and washed with Et$_2$O (3×100 mL) before the cake was allowed to fully dry. The product was purified via flash chromatography (SiO$_2$, gradient elution 50:49:1 EtOAc:Hex:MeOH to 75:24:1 EtOAc:Hex:MeOH) to afford 1 (1.56 g, 1.204 mmol, 28%) as an orange solid.

$R_f$=0.21 (50:49:1 EtOAc:Hex:MeOH)

$^1$H NMR: (500 MHz, CD$_3$C(O)CD$_3$) δ 7.43 (d, J=8.5 Hz, 2H), 7.38-7.33 (m, 2H), 6.90-6.82 (m, 4H), 6.48-6.18 (m, 11H), 6.05-5.84 (m, 3H), 5.59 (dd, J=14.3, 9.3 Hz, 1H), 5.52 (s, 1H), 5.46 (s, 1H), 5.45-5.38 (m, 1H), 5.28-5.22 (m, 1H), 4.71-4.62 (m, 3H), 4.60 (d, J=7.0 Hz, 1H), 4.53 (q, J=7.2, 4.6 Hz, 2H), 4.17 (tt, J=10.4, 6.0 Hz, 2H), 3.95 (dd, J=9.9, 6.9 Hz, 3H), 3.79 (d, J=2.9 Hz, 7H), 3.77-3.66 (m, 3H), 3.61 (td, J=9.0, 3.2 Hz, 1H), 3.45 (d, J=8.0 Hz, 1H), 3.39 (p, J=6.8 Hz, 2H), 3.33 (q, J=8.6 Hz, 3H), 3.08 (s, 2H), 2.36-2.25 (m, 3H), 1.96-1.88 (m, 2H), 1.88-1.78 (m, 3H), 1.73 (dt, J=16.4, 8.1 Hz, 3H), 1.69-1.42 (m, 8H), 1.41-1.21 (m, 28H), 1.19 (p, J=5.2 Hz, 4H), 1.13-1.08 (m, 5H), 1.02 (d, J=7.1 Hz, 4H), 0.95 (d, J=6.6 Hz, 2H), 0.87 (dt, J=12.0, 7.0 Hz, 22H).

HRMS (ESI)

Calculated for $C_{71}H_{95}NO_{21}$ (M+Na)$^+$: 1320.6294.
Found: 1320.6285.

Example 2. Synthesis of Intermediate 2

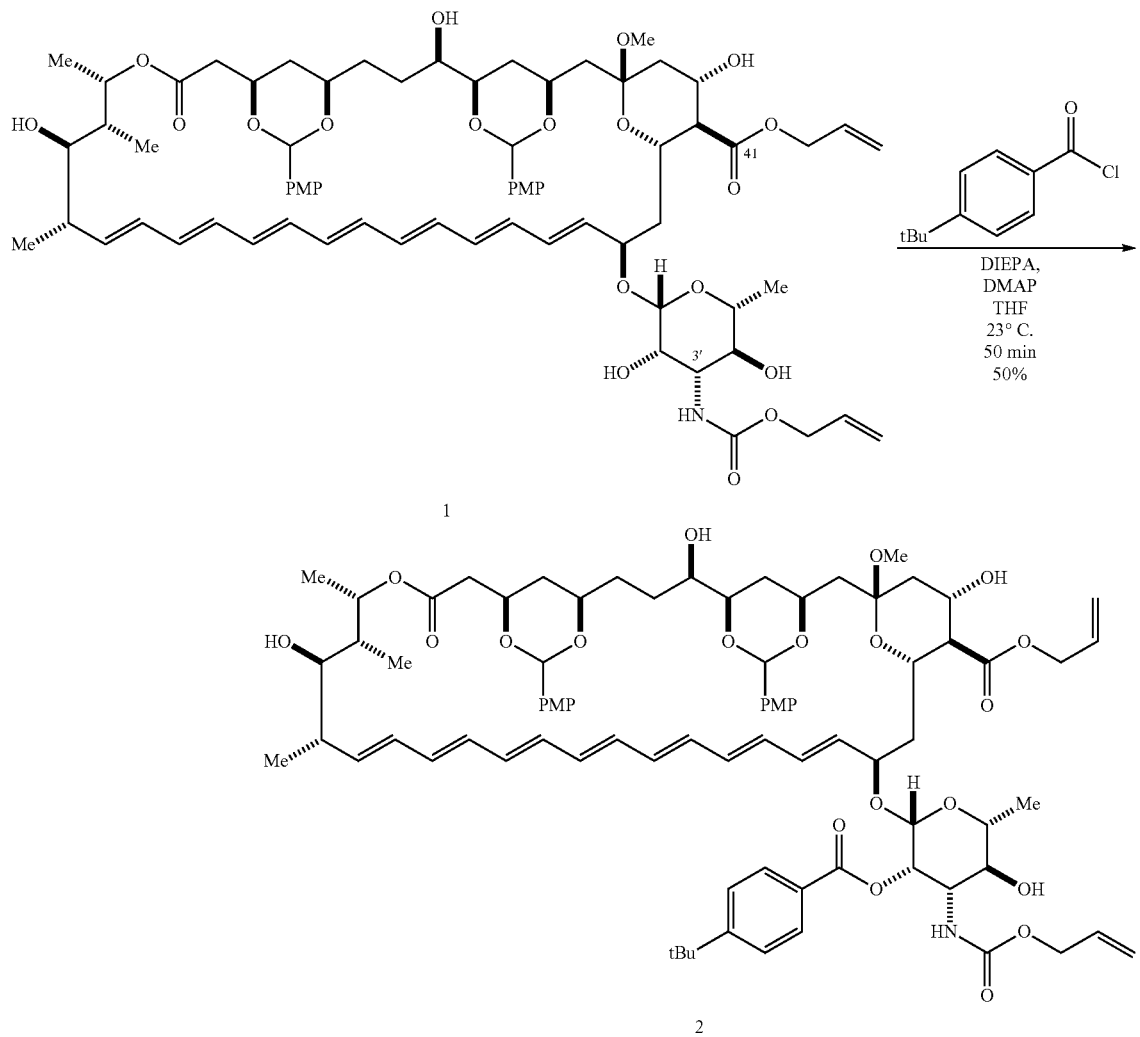

dried over sodium sulfate, filtered and concentrated under reduced pressure. Purification by flash chromatography (SiO$_2$, gradient eluent 65:33:2 EtOAc:Hex:MeOH isocratic) afforded 2 (2.28 g, 1.56 mmol, 50% yield) as an orange solid.

$R_f$=0.24 (65:33:2 EtOAc:Hex:MeOH)

$^1$H NMR: (500 MHz, CD$_3$C(O)CD$_3$) δ 8.07-7.89 (m, 2H), 7.64-7.48 (m, 2H), 7.38 (ddt, J=25.4, 8.0, 2.2 Hz, 4H), 6.86 (ddd, J=9.5, 4.6, 2.4 Hz, 4H), 6.46-6.11 (m, 10H), 6.10-5.96

Intermediate 1 (4.06 g, 3.127 mmol, 1.0 equiv.) was azeotropically dried with benzene (3×10 mL) and placed on high vacuum overnight in a 500 mL round bottom flask. To intermediate 1 was added THF (105 mL) followed by DIPEA (0.87 mL, 5.0 mmol, 1.6 equiv.). In a separate 200 mL round bottom flask was added sequentially THF (64 mL), DMAP (611.2 mg, 5.0 mmol, 1.6 equiv.), and dropwise p-tertbutylbenzoylchloride (855 μL, 4.38 mmol, 1.4 equiv.) forming a fine, white suspension. Most of this suspension was slowly added dropwise via cannula to the THF, DIPEA and 1 solution over ~50 min until a majority of the starting material was converted as judged by TLC. The reaction was diluted with EtOAc and transferred to a reparatory funnel containing aqueous saturated sodium bicarbonate and extracted with EtOAc. The combined organic phases were (m, 3H), 5.96-5.82 (m, 3H), 5.82-5.65 (m, 1H), 5.58 (d, J=3.7 Hz, 1H), 5.52-5.38 (m, 2H), 5.33-5.18 (m, 1H), 5.11 (td, J=9.2, 7.5, 3.9 Hz, 1H), 4.88 (s, 0H), 4.73-4.56 (m, 2H), 4.49 (t, J=5.9 Hz, 1H), 4.24-4.10 (m, 1H), 4.01-3.82 (m, 2H), 3.82-3.75 (m, 4H), 3.75-3.63 (m, 1H), 3.59 (td, J=9.6, 6.1 Hz, 1H), 3.56-3.46 (m, 1H), 3.45-3.34 (m, 1H), 2.85 (s, 1H), 2.60 (s, 1H), 2.45-2.35 (m, 1H), 2.35-2.23 (m, 1H), 2.02-1.94 (m, 1H), 1.91-1.82 (m, 1H), 1.80-1.40 (m, 6H), 1.36 (d, J=3.6 Hz, 8H), 1.32-1.26 (m, 3H), 1.22-1.15 (m, 2H), 1.12 (d, J=6.7 Hz, 2H), 1.01 (d, J=7.1 Hz, 2H).

HRMS (ESI)

Calculated for $C_{82}H_{107}NO_{22}$ (M+Na)$^+$: 1480.7182.
Found: 1480.7172.

Example 3. Synthesis of Intermediate 3

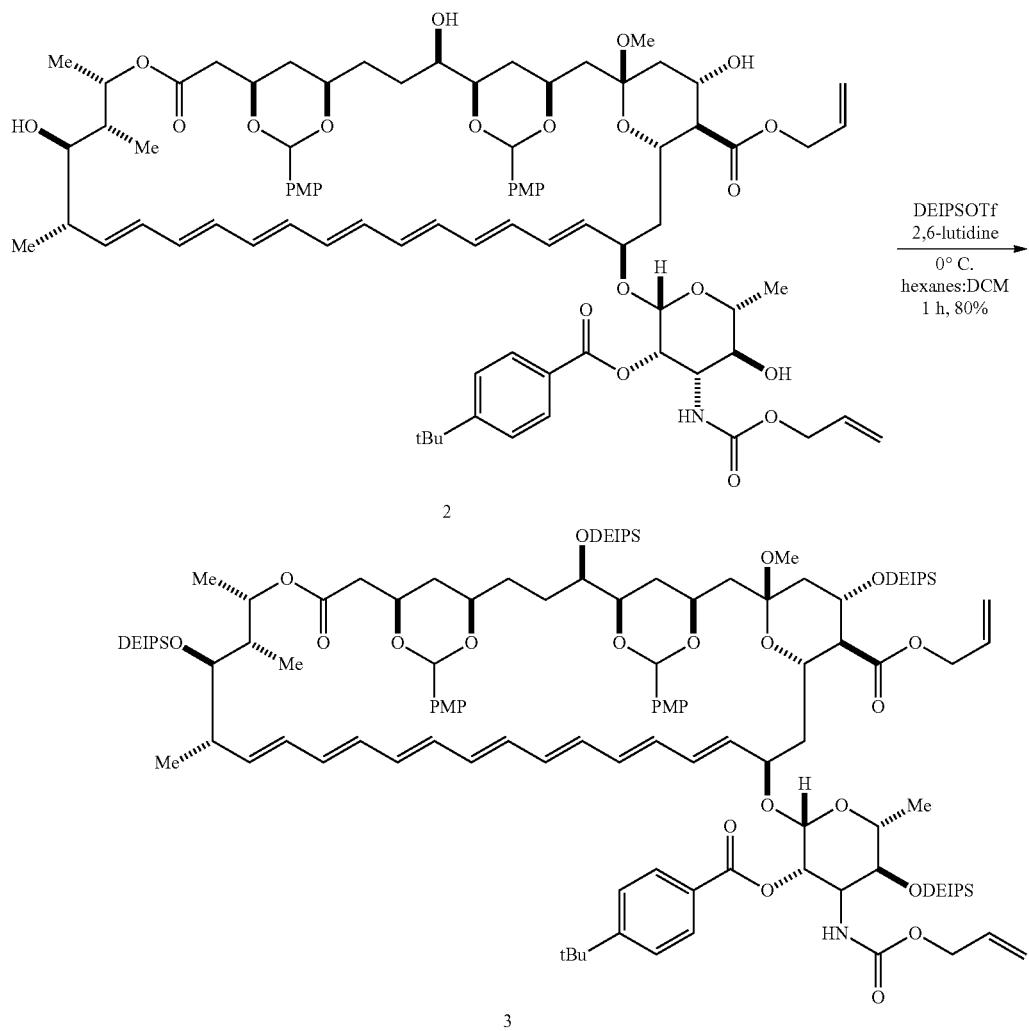

Intermediate 2 (4.15 g, 2.846 mmol, 1.0 equiv.) was azeotropically dried with benzene (3×10 mL) and placed on high vacuum overnight in a 300 mL round bottom flask. To intermediate 3 was added DCM (48 mL) and hexanes (48 mL) followed by freshly distilled 2,6-lutidine (2.98 mL, 25.58 mmol, 9.1 equiv.) and cooled to 0° C. Diethylisopropylsilyl triflate (DEIPSOTf; 3.39 mL, 17.05 mmol, 6.0 equiv.) was added dropwise over 10 min and stirred for another hour at 0° C. The reaction was diluted with $Et_2O$ (200 mL), transferred to a reparatory funnel containing $Et_2O$ and aqueous saturated bicarbonate, and extracted with $Et_2O$. The combined organic phases were dried over sodium sulfate, filtered and concentrated under reduced pressure. Purification by flash chromatography ($SiO_2$, gradient eluent 1:9 EtOAc:Hex to 1:4 EtOAx:Hex) afforded 3 (4.46 g, 2.28 mmol, 80% yield) as an orange solid.

$R_f$=0.21 (1:4 EtOAc:Hex)

$^1$H NMR: (500 MHz, $CD_3C(O)CD_3$) δ 8.07-7.95 (m, 2H), 7.65-7.54 (m, 2H), 7.37-7.31 (m, 4H), 6.94-6.81 (m, 6H), 6.41-6.32 (m, 5H), 6.32-6.24 (m, 3H), 6.20-6.13 (m, 3H), 6.10-5.84 (m, 4H), 5.72 (ddd, J=21.6, 15.2, 6.4 Hz, 2H), 5.52 (d, J=3.3 Hz, 1H), 5.45 (q, J=1.6 Hz, 0H), 5.41 (d, J=10.3 Hz, 3H), 5.34 (dt, J=10.3, 1.4 Hz, 1H), 5.27 (dq, J=17.3, 1.8 Hz, 1H), 5.13 (dq, J=10.4, 1.5 Hz, 1H), 4.91 (d, J=1.1 Hz, 1H), 4.75 (s, 1H), 4.71-4.62 (m, 2H), 4.62-4.55 (m, 2H), 4.52 (dt, J=5.6, 1.6 Hz, 2H), 4.33-4.25 (m, 1H), 4.19-4.08 (m, 1H), 4.07-3.94 (m, 1H), 3.93-3.81 (m, 3H), 3.81-3.73 (m, 10H), 3.72-3.60 (m, 4H), 3.51 (dq, J=8.8, 6.1 Hz, 1H), 2.75 (s, 3H), 2.53-2.39 (m, 2H), 2.27 (dd, J=17.7, 4.4 Hz, 1H), 2.23-2.11 (m, 2H), 2.09 (s, 7H), 1.99-1.94 (m, 1H), 1.89 (ddt, J=12.5, 8.0, 3.9 Hz, 1H), 1.78-1.56 (m, 5H), 1.56-1.41 (m, 4H), 1.37 (d, J=3.4 Hz, 14H), 1.32-1.21 (m, 6H), 1.21-1.11 (m, 7H), 1.09 (d, J=6.8 Hz, 3H), 1.07-0.76 (m, 79H), 0.76-0.65 (m, 12H), 0.61-0.49 (m, 7H), 0.43 (dqd, J=14.1, 7.9, 1.7 Hz, 5H).

$^{13}$C NMR: (126 MHz, $CD_3C(O)CD_3$) δ 172.60, 170.01, 166.28, 160.93, 160.80, 157.48, 157.01, 138.66, 135.17, 134.93, 134.66, 134.40, 134.27, 134.01, 133.67, 133.05, 132.92, 132.79, 132.29, 131.26, 130.93, 130.90, 129.29, 129.12, 128.87, 128.47, 127.24, 126.28, 119.43, 117.28, 114.09, 114.08, 113.99, 102.02, 101.18, 100.78, 96.73, 81.57, 75.89, 75.03, 74.97, 74.17, 73.14, 73.02, 72.98, 68.92, 66.82, 65.95, 65.84, 58.56, 57.01, 55.68, 48.58, 43.99, 42.91, 41.29, 38.08, 36.90, 35.90, 33.75, 32.97, 31.64, 30.77, 28.14, 19.27, 18.24, 18.19, 18.07, 18.01, 17.70, 17.68, 14.19, 14.17, 14.03, 13.76, 7.94, 7.90, 7.82, 7.77, 7.72, 7.71, 7.48, 7.36, 5.21, 5.10, 4.94, 4.89, 4.69, 4.44.

HRMS (ESI)

Calculated for $C_{110}H_{171}NO_{22}$ (M+Na)$^+$: 1993.1268. Found: 1993.1189.

Example 4. Synthesis of Intermediate 4 tography (SiO$_2$, gradient eluent 1:9 EtOAc:Hex to 1:4 EtOAx:Hex) afforded 4 (2.93 g, 1.62 mmol, 50% yield) as an orange solid.

R$_f$=0.22 (3:7 EtOAc:Hex)

$^1$H NMR: (500 MHz, CD$_3$C(O)CD$_3$) δ 7.43-7.30 (m, 5H), 6.92-6.79 (m, 5H), 6.48-6.14 (m, 12H), 6.11 (dd, J=15.0, 10.0 Hz, 1H), 6.03-5.89 (m, 3H), 5.88-5.73 (m, 2H), 5.43 (d, J=3.6 Hz, 3H), 5.37 (dq, J=21.8, 1.6 Hz, 1H), 5.33-5.26 (m, 2H), 5.17 (dq, J=10.6, 1.5 Hz, 1H), 4.79 (s, 1H), 4.71-4.48

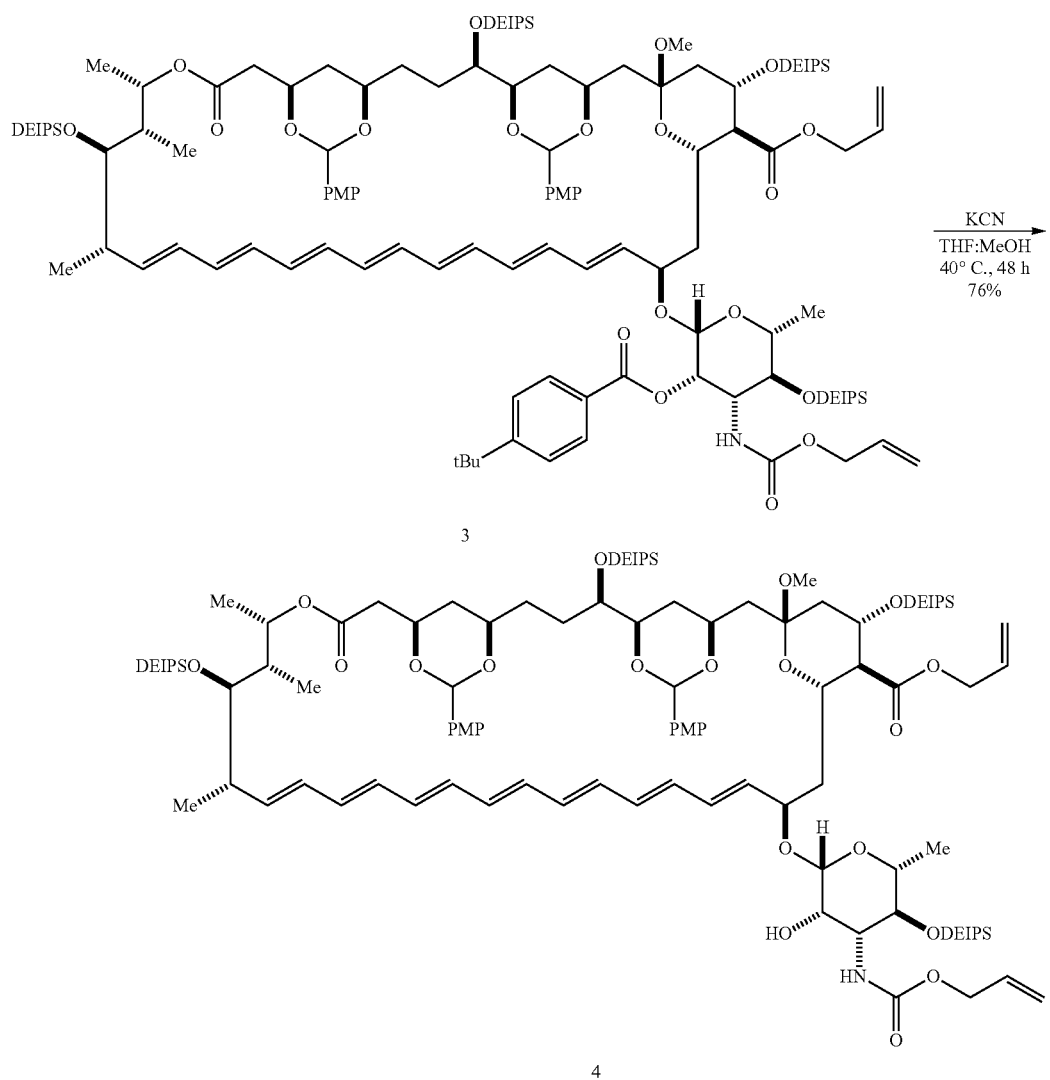

Intermediate 3 (6.39 g, 3.24 mmol, 1.0 equiv.) was azeotropically dried with benzene (3×10 mL) and placed on high vacuum overnight in a 300 mL round bottom flask. To intermediate 3 was added THF (71 mL) and MeOH (140 mL) followed by KCN (314.8 mg, 4.83 mmol, 1.5 equiv.) placed under Ar atmosphere, sealed and warmed to 40° C. and stirred for 48 h behind a blast shield. The reaction transferred to a reparatory funnel containing Et$_2$O and aqueous saturated bicarbonate. The organic phase was washed with water followed by brine. The combined aqueous phases were extracted with Et$_2$O. The combined organic phases were dried over sodium sulfate, filtered and concentrated under reduced pressure. Purification by flash chroma- (m, 7H), 4.27 (td, J=10.6, 4.7 Hz, 1H), 4.21-4.11 (m, 1H), 3.95-3.82 (m, 4H), 3.79 (s, 4H), 3.78 (s, 4H), 3.77-3.63 (m, 6H), 3.54 (t, J=9.2 Hz, 1H), 3.38-3.26 (m, 1H), 2.49 (dd, J=17.6, 7.6 Hz, 1H), 2.43 (q, J=7.1 Hz, 1H), 2.32-2.24 (m, 3H), 1.96 (s, 3H), 1.94-1.86 (m, 2H), 1.82-1.67 (m, 3H), 1.66-1.57 (m, 2H), 1.58-1.27 (m, 7H), 1.26 (d, J=6.1 Hz, 4H), 1.23-1.10 (m, 8H), 1.10-0.86 (m, 58H), 0.86-0.76 (m, 15H), 0.70 (tdt, J=8.2, 4.4, 2.9 Hz, 11H), 0.63-0.48 (m, 5H), 0.48-0.36 (m, 4H).

HRMS (ESI)

Calculated for $C_{99}H_{159}NO_{21}$ (M+Na)$^+$: 1833.0379. Found: 1833.0355.

Example 5. Synthesis of Intermediate 5

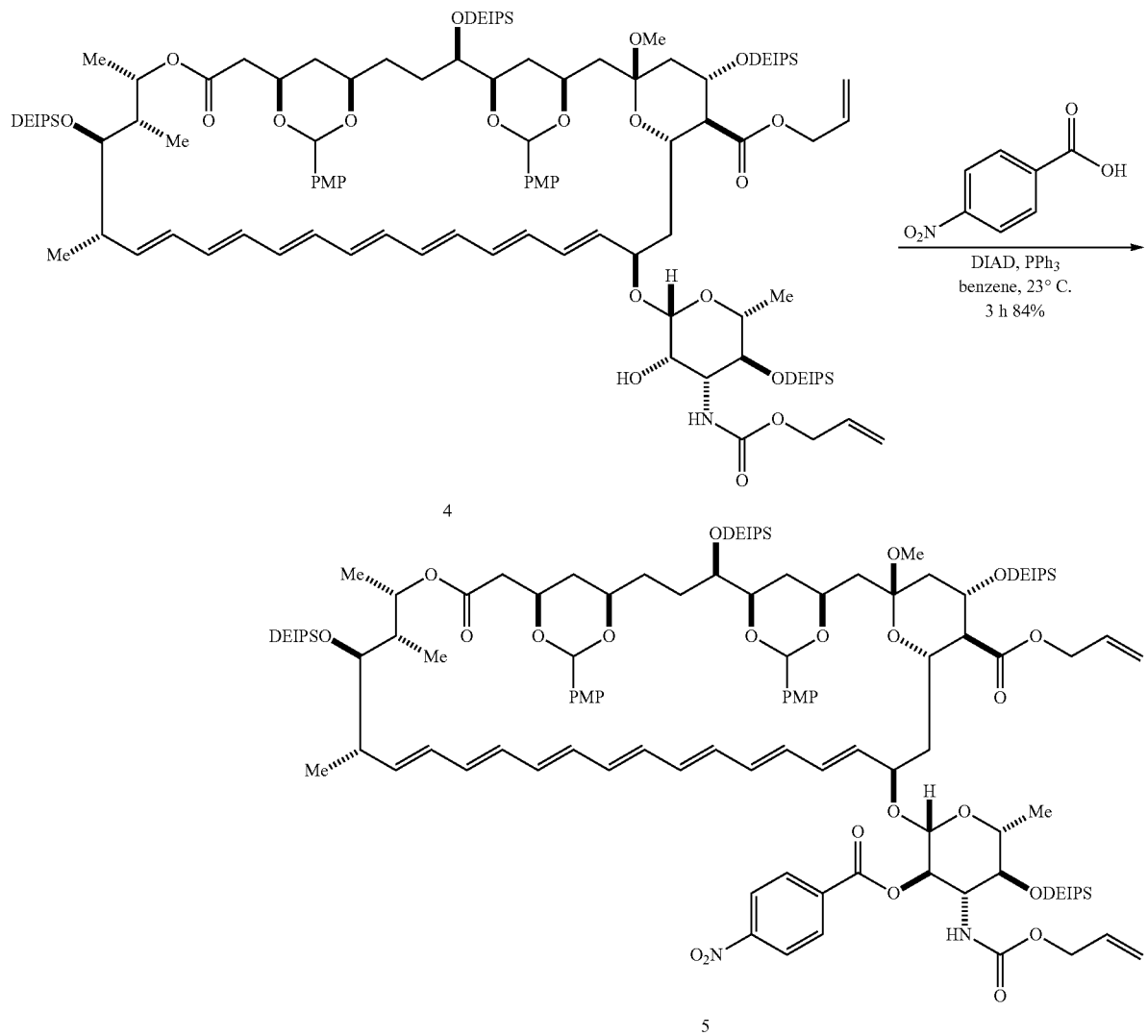

Intermediate 4 (2.93 g, 1.62 mmol, 1.0 equiv.) was azeotropically dried with benzene (3×10 mL) and placed on high vacuum overnight in a 250 mL round bottom flask. To intermediate 4 was added p-nitrobenzoic acid (1.62 g, 9.7 mmol, 6.0 equiv.), PPh$_3$ (2.54 mg, 9.7 mmol, 6.0 equiv.) and benzene (54 mL). The solution was cooled to 0° C. and DIAD (1.91 mL, 9.7 mmol, 6.0 equiv.) was added drop-wise and stirred at 0° C. for 1 h. The reaction was then stirred at 23° C. for 3 h. The reaction was transferred to a separatory funnel containing Et$_2$O and aqueous saturated sodium bicarbonate. The organic phase was washed with water followed by brine. The combined aqueous phases were extracted with Et$_2$O. The combined organic phases were dried over sodium sulfate, filtered and concentrated under reduced pressure. Purification by flash chromatography (SiO$_2$, gradient eluent 1:9 EtOAc:Hex to 1:4 EtOAx:Hex) afforded C2'epi nitrobenzoate 5 (2.66 g, 1.36 mmol, 84% yield) as an orange solid.

R$_f$=0.2 (1:4 EtOAc:Hex)

$^1$H NMR: (500 MHz, CD$_3$C(O)CD$_3$) δ 8.37 (s, 4H), 7.37-7.30 (m, 4H), 6.89-6.81 (m, 5H), 6.50 (d, J=9.8 Hz, 1H), 6.45-6.09 (m, 15H), 6.07-5.95 (m, 1H), 5.86 (ddd, J=19.1, 14.5, 5.8 Hz, 2H), 5.67 (ddt, J=17.3, 10.6, 5.4 Hz, 1H), 5.47-5.39 (m, 2H), 5.35 (s, 1H), 5.30 (dq, J=10.4, 1.3 Hz, 1H), 5.15 (dd, J=10.4, 7.9 Hz, 1H), 5.08 (dq, J=17.2, 1.7 Hz, 1H), 4.92 (dq, J=10.5, 1.4 Hz, 1H), 4.82 (d, J=7.8 Hz, 1H), 4.79-4.69 (m, 2H), 4.61 (qdt, J=13.1, 6.0, 1.4 Hz, 3H), 4.33 (qdt, J=13.6, 5.4, 1.5 Hz, 2H), 4.18-4.09 (m, 1H), 3.97 (td, J=10.6, 4.6 Hz, 1H), 3.90-3.81 (m, 3H), 3.77 (d, J=2.9 Hz, 8H), 3.75-3.63 (m, 7H), 3.52 (dq, J=9.0, 6.1 Hz, 1H), 2.69 (s, 3H), 2.53-2.39 (m, 2H), 2.34-2.21 (m, 1H), 2.19-2.07 (m, 2H), 2.04-1.98 (m, 1H), 1.88 (dddd, J=12.9, 10.2, 6.6, 3.8 Hz, 1H), 1.79 (d, J=15.5 Hz, 1H), 1.76-1.64 (m, 2H), 1.61 (dt, J=13.0, 2.5 Hz, 1H), 1.56-1.40 (m, 5H), 1.37-1.24 (m, 14H), 1.23-1.12 (m, 8H), 1.10-0.95 (m, 45H), 0.94-0.84 (m, 19H), 0.84-0.76 (m, 13H), 0.74-0.60 (m, 15H), 0.53 (dqd, J=26.8, 7.8, 3.2 Hz, 5H), 0.42-0.28 (m, 5H).

$^{13}$C NMR: (126 MHz, CD$_3$C(O)CD$_3$) δ 173.00, 170.05, 164.87, 160.93, 160.79, 157.06, 151.67, 138.05, 136.54, 134.87, 134.73, 134.64, 134.56, 134.45, 134.16, 133.82, 133.65, 133.35, 132.91, 132.75, 132.48, 132.40, 131.84, 130.96, 128.86, 128.47, 127.65, 124.39, 119.57, 117.11, 114.07, 113.98, 101.97, 101.21, 100.71, 98.47, 81.53, 76.09, 76.00, 75.09, 74.92, 73.67, 73.04, 72.94, 68.84, 66.84, 66.12, 65.56, 59.60, 58.12, 55.66, 55.12, 48.39, 43.94, 42.99, 41.32, 38.08, 36.35, 33.68, 32.96, 28.21, 22.01, 18.87, 18.20, 18.14, 18.00, 17.98, 17.93, 17.62, 17.60, 14.15, 14.12, 14.02, 13.67, 7.90, 7.86, 7.76, 7.73, 7.69, 7.66, 7.36, 5.15, 5.06, 4.93, 4.91, 4.88, 4.63, 4.36.

HRMS (ESI)
Calculated for $C_{106}H_{162}N_2O_{24}Si_4$ (M+Na)$^+$: 1982.0492. Found: 1982.0464.

Example 6. Synthesis of Intermediate 6

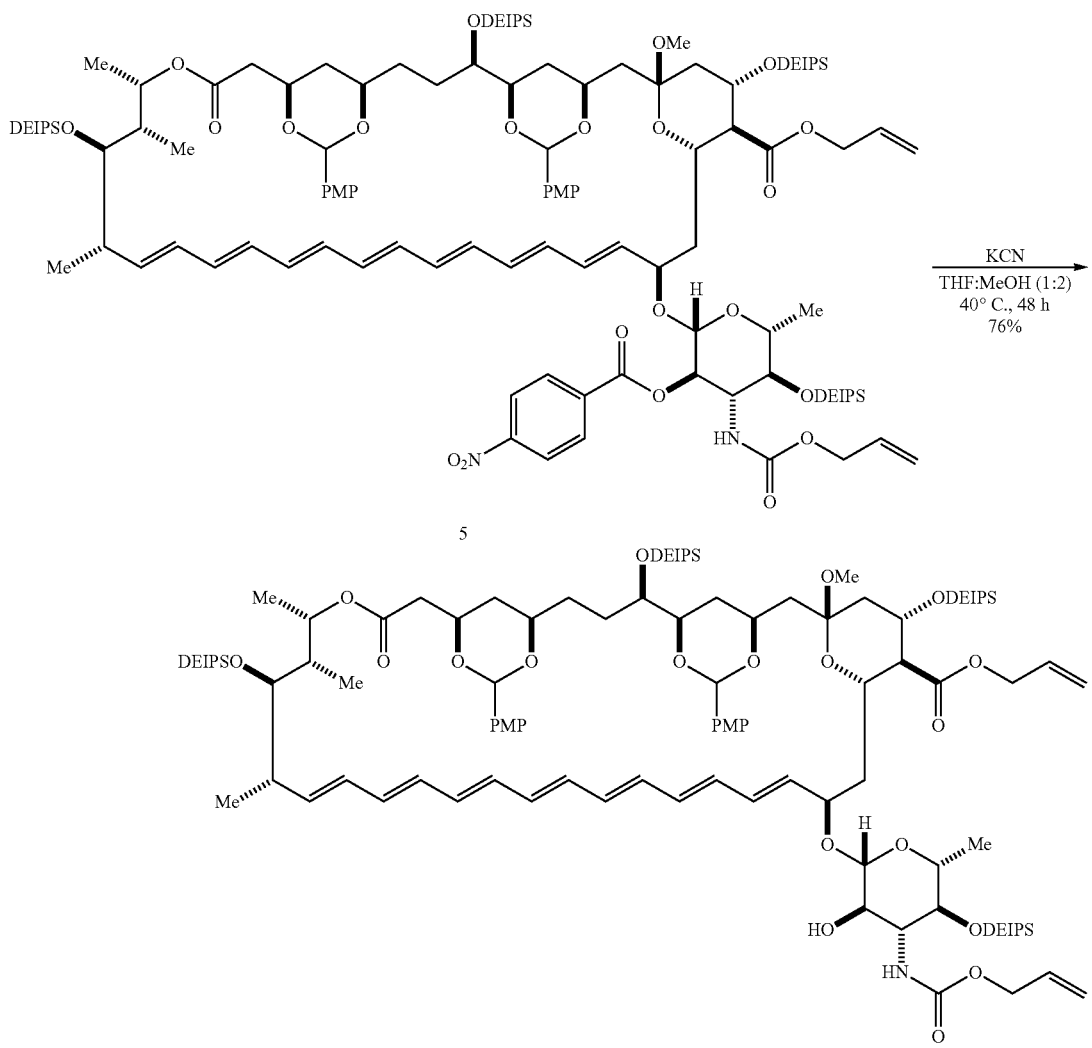

Intermediate 5 (2.46 g, 1.25 mmol, 1.0 equiv.) was azeotropically dried with benzene (3×10 mL) and placed on high vacuum overnight in a 250 mL iChem. To intermediate 5 was added THF (27.3 mL) and MeOH (54.6 mL) followed by KCN (121.8 mg, 1.87 µmol, 1.5 equiv.) placed under Ar atmosphere, sealed and warmed to 40° C. and stirred for 48 h behind a blast shield. The reaction transferred to a reparatory funnel containing Et$_2$O and aqueous saturated bicarbonate. The organic phase was washed with water followed by brine. The combined aqueous phases were extracted with Et$_2$O. The combined organic phases were dried over sodium sulfate, filtered and concentrated under reduced pressure. Purification by flash chromatography (SiO$_2$, gradient eluent 1:9 EtOAc:Hex to 1:4 EtOAx:Hex) afforded 6 (1.72 g, 0.948 mmol, 76% yield) as an orange solid.

R$_f$=0.2 (3:7 EtOAc:Hex)

$^1$H NMR: (500 MHz, CD$_3$C(O)CD$_3$) δ 7.43-7.32 (m, 4H), 6.87 (ddd, J=13.9, 8.9, 2.1 Hz, 4H), 6.47-6.15 (m, 13H), 6.10 (dd, J=15.1, 10.0 Hz, 1H), 6.06-5.82 (m, 3H), 5.78 (dd, J=15.1, 8.6 Hz, 1H), 5.43 (d, J=6.0 Hz, 3H), 5.36 (dt, J=31.2, 1.6 Hz, 1H), 5.31-5.25 (m, 1H), 5.16 (dt, J=10.7, 1.5 Hz, 1H), 4.81 (s, 1H), 4.66-4.55 (m, 3H), 4.51 (td, J=4.9, 3.9, 1.5 Hz, 2H), 4.37 (d, J=6.5 Hz, 1H), 4.33-4.23 (m, 1H), 4.22-4.12 (m, 1H), 4.01-3.82 (m, 3H), 3.79 (d, J=1.8 Hz, 3H), 3.78 (d, J=1.9 Hz, 3H), 3.76-3.66 (m, 4H), 3.43 (tt, J=9.2, 3.9 Hz, 3H), 3.34 (h, J=6.3 Hz, 1H), 3.05 (d, J=1.9 Hz, 3H), 2.49 (dd, J=17.6, 7.7 Hz, 1H), 2.46-2.38 (m, 1H), 2.27 (dt, J=14.3, 4.6 Hz, 3H), 2.09 (d, J=1.6 Hz, 4H), 2.01-1.93 (m, 1H), 1.93-1.85 (m, 2H), 1.85-1.77 (m, 1H), 1.73 (q, J=10.2, 9.4 Hz, 1H), 1.68-1.38 (m, 7H), 1.31 (q, J=10.9 Hz, 5H), 1.24 (t, J=5.4 Hz, 4H), 1.22-1.16 (m, 6H), 1.10-0.86 (m, 52H), 0.86-0.75 (m, 14H), 0.69 (dddd, J=13.6, 11.6, 8.0, 3.8 Hz, 10H), 0.63-0.49 (m, 4H), 0.49-0.34 (m, 4H).

$^{13}$C NMR: (126 MHz, CD$_3$C(O)CD$_3$) δ 173.37, 170.15, 160.95, 160.81, 157.34, 137.97, 134.87, 134.84, 134.77, 134.74, 134.35, 134.15, 133.96, 133.77, 133.56, 133.36, 132.90, 132.78, 132.42, 131.08, 129.69, 128.90, 128.50, 119.55, 117.30, 114.08, 114.01, 103.12, 102.07, 101.27, 100.90, 81.60, 76.29, 76.20, 75.23, 74.59, 73.32, 73.28, 72.97, 69.07, 67.63, 66.27, 65.64, 61.38, 57.67, 55.66, 48.58, 44.14, 43.33, 41.41, 38.08, 37.66, 33.73, 32.93, 30.76, 28.33, 19.26, 19.11, 18.21, 18.14, 18.05, 18.02, 18.00, 17.69, 17.67, 14.15, 14.04, 13.72, 7.90, 7.87, 7.80, 7.78, 7.75, 7.71, 7.47, 7.45, 5.18, 5.06, 5.02, 4.96, 4.90, 4.88, 4.66, 4.43.

HRMS (ESI)
Calculated for C$_{99}$H$_{159}$NO$_{21}$Si$_4$ (M+Na)$^+$: 1833.0379.
Found: 1833.0309.

Example 7. Synthesis of Intermediate 7

To a 30 mL Teflon vial charged with MeOH (14.5 mL) at 0° C. was added HF-pyridine 70% solution (2.05 mL). To a separate 100 mL Teflon vial containing 6 (1.05 g, 0.65 mmol) as an azeotropically dried solid was charged with THF (7.2 mL) and cooled to 0° C. The contents of the first vial were transferred slowly via cannula to the second vial over 20 min. At this point the ice bath was removed and the reaction was allowed to stir at 23° C. for 6 h. Upon completion, the reaction was cooled to 0° C. and quenched by slow addition of saturated aqueous sodium bicarbonate (60 mL) and allowed to warm to 23° C. for 1 h. The biphasic suspension was then transferred to a reparatory funnel containing saturated aqueous sodium bicarbonate and EtOAc. The combined organics were washed with H$_2$O, saturated brine, dried with sodium sulfate, filtered and concentrated under vacuum. Purification by flash chromatography (SiO$_2$, gradient eluent 49:1 DCM:MeOH to 97:3 DCM:MeOH to 19:1 DCM:MeOH) afforded 7 (574 mg, 0.442 mmol, 68% yield) as an orange solid.

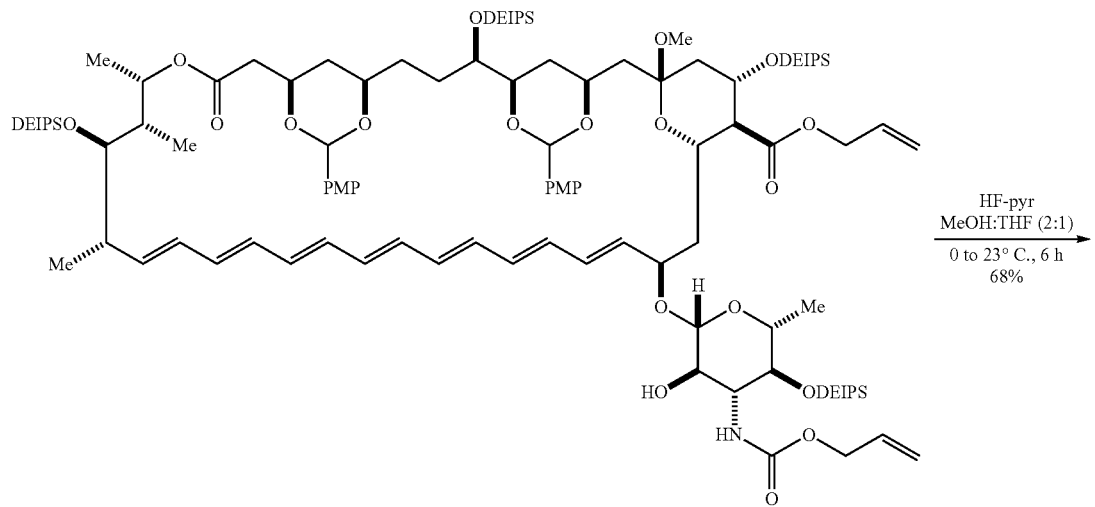

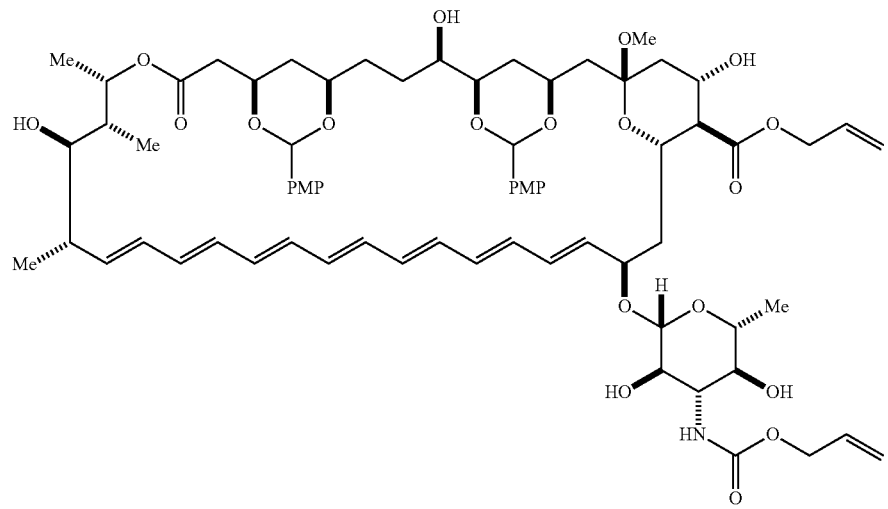

$R_f$=0.2 (19:1 DCM:MeOH)

¹H NMR: (500 MHz, Acetone-$d_6$) δ 7.48-7.32 (m, 5H), 6.91-6.81 (m, 5H), 6.35 (dddd, J=53.1, 19.0, 13.1, 8.3 Hz, 18H), 6.06-5.87 (m, 3H), 5.60 (p, J=8.4, 7.5 Hz, 1H), 5.54-5.38 (m, 3H), 5.35-5.20 (m, 3H), 5.19-5.11 (m, 1H), 4.70-4.56 (m, 4H), 4.52 (d, J=5.4 Hz, 3H), 4.38 (d, J=7.5 Hz, 2H), 4.27-4.08 (m, 3H), 4.10-3.90 (m, 3H), 3.89-3.83 (m, 1H), 3.77 (d, J=3.6 Hz, 9H), 3.56 (d, J=5.6 Hz, 1H), 3.52-3.33 (m, 6H), 3.22-3.13 (m, 1H), 3.08 (s, 3H), 2.59 (dt, J=14.5, 7.3 Hz, 1H), 2.36 (tdd, J=27.1, 16.2, 7.3 Hz, 5H), 2.09 (s, 1H), 2.07-1.99 (m, 2H), 1.97 (s, 1H), 1.96-1.82 (m, 3H), 1.83-1.64 (m, 3H), 1.62-1.56 (m, 1H), 1.38 (d, J=11.8 Hz, 1H), 1.28-1.19 (m, 8H), 1.15 (d, J=6.4 Hz, 4H), 1.04 (d, J=7.0 Hz, 4H).

¹³C NMR: (126 MHz, Acetone) δ 206.32, 173.28, 170.86, 169.77, 160.51, 160.43, 158.26, 150.38, 137.62, 137.01, 134.35, 134.24, 134.18, 134.06, 133.88, 133.77, 133.42, 133.05, 132.81, 132.57, 132.51, 132.32, 130.13, 128.29, 128.24, 128.19, 124.55, 118.50, 117.18, 114.18, 113.87, 102.86, 101.05, 100.73, 100.55, 81.03, 77.97, 76.51, 76.34, 75.25, 73.92, 73.25, 73.19, 72.92, 70.58, 67.58, 67.10, 65.74, 65.67, 60.88, 60.46, 56.96, 55.45, 48.64, 43.54, 42.66, 41.80, 41.47, 37.89, 37.66, 33.85, 33.34, 30.58, 28.76, 23.21, 20.80, 18.99, 18.34, 17.60, 14.44, 14.32, 11.97.

HRMS (ESI)
Calculated for $C_{71}H_{95}NO_{21}(M+Na)^+$: 1320.6274.
Found: 1320.6294.

Example 8. Synthesis of Intermediate 8

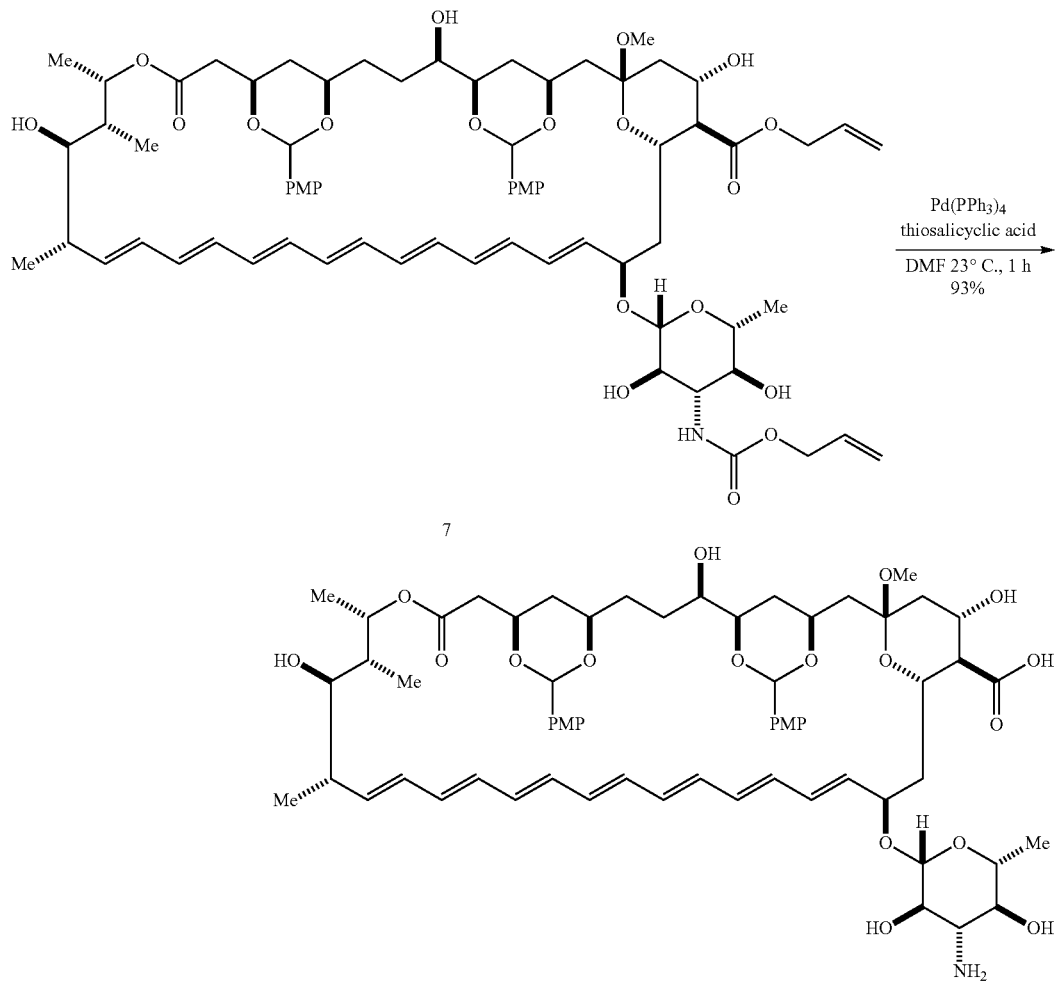

To a 40 mL iChem vial charged with 7 (473 mg, 0.364 mmol, 1.0 eq.) was added in the glove box Pd(PPh$_3$)$_4$ (126 mg, 0.109 mmol, 0.3 eq.), thiosalicylic acid (112 mg, 0.726 mmol, 2.0 eq.) and sealed. Outside of the glove box was then added DMF (14.7 mL) at 23° C. and stirred for 1 h. The reaction was then added dropwise to stirring Et$_2$O (300 mL). The resulting yellow precipitate was then filtered through Whatman 50 filter paper and rinsed with excess Et$_2$O. The filtrate was then concentrated and slowly added to stirring Et$_2$O (150 mL). This process was repeated until all of the precipitate was collected. The orange-yellow solid intermediate 8—a single peak by analytical HPLC (397.4 mg, 0.339 mmol, 93%) was taken on to the next reaction without further purification.

$R_t$=15.9 min ($C_{18}SiO_2$ 5.95→95:5 MeCN:H$_2$O 5 mM NH$_4$OAc over 20 min @ 1 mL/min)

¹H NMR: (500 MHz, Methanol-$d_4$) δ 7.51-7.39 (m, 4H), 6.84-6.75 (m, 4H), 6.32 (dddd, J=36.2, 31.5, 17.4, 9.9 Hz, 13H), 6.01 (dd, J=14.5, 6.0 Hz, 1H), 5.57 (s, 1H), 5.52 (q, J=4.5 Hz, 2H), 5.40-5.35 (m, 1H), 5.30 (s, 18H), 4.81-4.74 (m, 1H), 4.72 (d, J=7.5 Hz, 1H), 4.47 (td, J=10.7, 4.6 Hz, 1H), 4.36-4.27 (m, 2H), 4.08-4.00 (m, 1H), 3.86-3.72 (m, 2H), 3.69-3.54 (m, 9H), 3.47-3.35 (m, 3H), 3.33 (dq, J=3.1, 1.4 Hz, 7H), 3.09 (d, J=0.9 Hz, 3H), 2.64 (dd, J=16.8, 6.6 Hz, 1H), 2.52 (dd, J=13.1, 4.6 Hz, 1H), 2.49-2.37 (m, 2H), 2.34 (dd, J=16.9, 6.1 Hz, 1H), 2.15-2.04 (m, 1H), 2.02-1.83 (m, 5H), 1.70 (q, J=11.7 Hz, 1H), 1.61-1.52 (m, 4H), 1.44-1.36 (m, 1H), 1.33 (d, J=6.0 Hz, 3H), 1.28 (dd, J=12.9, 10.4 Hz, 1H), 1.22 (d, J=6.3 Hz, 3H), 1.15 (d, J=6.4 Hz, 4H), 1.12-1.08 (m, 1H), 1.06 (d, J=7.0 Hz, 3H).

$^{13}$C NMR: (126 MHz, CD$_3$OD) δ 179.76, 170.66, 160.94, 160.80, 135.39, 135.30, 134.42, 134.30, 134.16, 134.40, 133.98, 133,54, 133.45, 132.89, 132.78, 132.67, 131.25, 128.72, 128.59, 114.22, 114.17, 102.51, 101.69, 101.26, 101.14, 81.52, 78.40, 77.94, 77.00, 74.38, 73.37, 73.66, 73.49, 72.28, 71.21, 68.59, 67.89, 60.19, 59.72, 55.62, 55.60, 41.82, 38.22, 33.80, 19.31, 18.29, 17.75, 12.37.

HRMS (ESI)
Calculated for C$_{64}$H$_{88}$NO$_{19}$: 1174.5941.
Found: 1174.5951.

Example 9. Synthesis of C2'epiAmB

To a 300 mL round bottom flask containing in azeotropically dried 8 (197 mg, 0.168 mmol, 1.0 eq.) was added MeCN (160 mL) and DI H$_2$O (8.0 mL). The suspension was then cooled to 0° C. whereupon CSA (5.85 g, 25.2 mmol, 150 mM) was added in one portion. The yellow orange suspension became a yellow orange clear solution upon the addition of CSA. Over time a fine precipitate forms. After stirring for 3 h at 0° C., triethyl amine (7.03 mL, 50.4 mmol, 300 eq.) was added. The reaction was then partially concentrated and purified by preparative HPLC (C$_{18}$SiO$_2$ 5:95→95:5 MeCN:H$_2$O 5 mM NH$_4$OAc over 20 min @ 1 mL/min) to yield C2'epiAmB (35.1 mg, 0.035 mmol, 21% yield) as a lyophilized free-flowing yellow powder.

R$_f$=11.17 min (C$_{18}$SiO$_2$ analytical HPLC, 5:95 to 95:5 MeCN:NH$_4$OAc (5 mM) over 20 min, 1 mL/min)

$^1$H NMR: (500 MHz, CD$_3$S(O)CD$_3$) δ 6.55-6.03 (m, 10H), 5.97 (dd, J=15.5, 8.7 Hz, 1H), 5.75 (d, J=10.9 Hz, 1H), 5.44 (dd, J=15.0, 10.1 Hz, 1H), 5.34 (s, 1H), 5.21 (d, J=7.9 Hz, 1H), 4.89-4.71 (m, 3H), 4.62 (d, J=5.7 Hz, 1H), 4.41 (d, J=6.3 Hz, 1H), 4.39-4.30 (m, 2H), 4.25 (t, J=10.5 Hz, 2H), 4.06 (s, 1H), 3.91 (d, J=10.4 Hz, 1H), 3.49 (d, J=31.6 Hz, 2H), 3.17-3.04 (m, 2H), 3.04-2.84 (m, 2H), 2.66 (d, J=11.9 Hz, 1H), 2.40 (s, 1H), 2.28 (dd, J=14.6, 7.5 Hz, 1H), 2.17 (t, J=8.5 Hz, 2H), 2.05-1.68 (m, 5H), 1.65-1.47

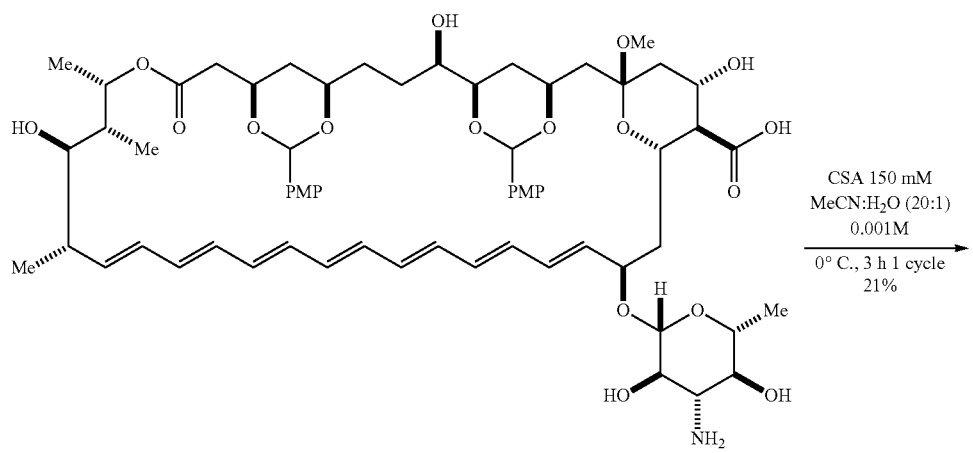

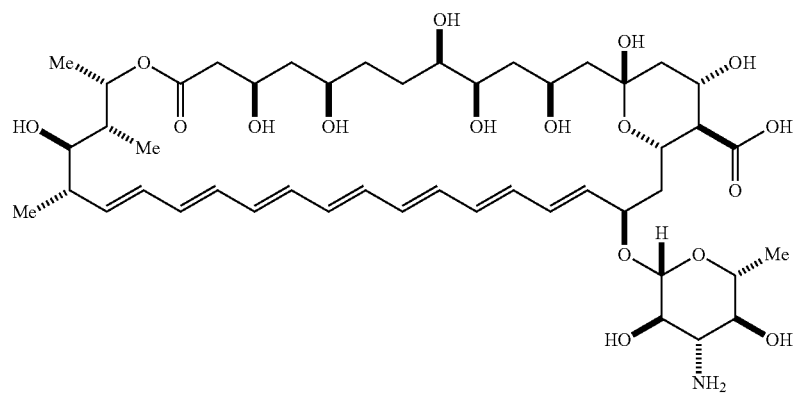

C2'epiAmB (m, 5H), 1.47-1.29 (m, 7H), 1.24 (q, J=5.6, 4.6 Hz, 6H), 1.20-1.08 (m, 6H), 1.04 (t, J=7.4 Hz, 3H), 0.91 (d, J=7.1 Hz, 3H), 0.86 (td, J=7.1, 4.2 Hz, 1H).

HRMS (ESI)

Calculated for $C_{47}H_{73}NO_{17}$ (M+H)$^+$: 924.4957.
Found: 924.4960.

Example 10. C2'epiAmB Binds Ergosterol but not Cholesterol

The binding capability of C2'epiAmB was investigated to determine whether epimerization at C2' impacts the capacity of AmB to bind ergosterol. C2'epiAmB binds to ergosterol, but not cholesterol, within the limits of the binding assay.

ITC data for C2'epiAmB is as follows:
No sterol: Total exotherm=−6.70±0.11 μcal.
10% ergosterol: Total exotherm=−15.24±1.66 μcal.
10% cholesterol: Total exotherm=−6.43±2.80 μcal.

Exemplary methods of conducting the binding assay are described below.

Isothermal Titration Calorimetry (ITC)

In an optimized isothermal titration calorimetry (ITC)-based assay, an aqueous solution of AmB was titrated with a suspension of large unilamellar vesicles (LUVs) comprised of only 1-palmitoyl-2-oleoyl-sn-glycero-3-phosphocholine (POPC), and the net exotherm was recorded. The titration was repeated using POPC LUVs containing 10% ergosterol. A significant increase in net exotherm was observed when switching to ergosterol-containing LUVs, indicating a direct AmB-sterol binding interaction. The titration was repeated using C2'epiAmB. A significant increase in net exotherm indicated a retained capacity for the epimeric derivative to bind ergosterol. The ITC assay was also conducted with cholesterol in place of ergosterol. C2'epiAmB was not found to bind to cholesterol.

General Information

Experiments were performed using a NanoITC isothermal titration calorimeter (TA Instruments, Wilmington, Del.). Solutions of the compounds to be tested were prepared by diluting a 60.0 mM stock solution of the compound in DMSO to 600 μM with K buffer (5.0 mM HEPES/KHEPES, pH=7.4). The final DMSO concentration in the solution was 1% v/v. Large unilamellar vesicles comprised of only 1-palmitoyl-2-oleoyl-sn-glycero-3-phosphocholine (POPC LUVs) were prepared and phosphorus and ergosterol content was quantified as described below. The LUV solutions were diluted with buffer and DMSO to give a final phospholipid concentration of 12.0 mM in a 1% DMSO/K buffer solution. Immediately prior to use, all solutions were incubated at 37° C. for 30 minutes and degassed under vacuum at 37° C. for 10 minutes. The reference cell of the instrument (volume=0.190 mL) was filled with a solution of 1% v/v DMSO/K buffer.

LUV Preparation

Palmitoyl oleoyl phosphatidylcholine (POPC) was obtained as a 20 mg/mL solution in $CHCl_3$ from Avanti Polar Lipids (Alabaster, Ala.) and was stored at −20° C. under an atmosphere of dry argon and used within 1 month. A 4 mg/mL solution of ergosterol in $CHCl_3$ was prepared monthly and stored at 4° C. under an atmosphere of dry argon. Prior to preparing a lipid film, the solutions were warmed to ambient temperature to prevent condensation from contaminating the solutions. A 13×100 mm test tube was charged with 800 μL POPC and 230 μL of the ergosterol solution. For cholesterol-containing liposomes, a 13×100 mm test tube was charged with 800 μL POPC and 224 μL of the ergosterol solution. For sterol-free liposomes, a 13×100 mm test tube was charged with 800 μL POPC. The solvent was removed with a gentle stream of nitrogen and the resulting lipid film was stored under high vacuum for a minimum of eight hours prior to use. The film was then hydrated with 1 mL of K buffer and vortexed vigorously for approximately 3 minutes to form a suspension of multilamellar vesicles (MLVs). The resulting lipid suspension was pulled into a Hamilton (Reno, Nev.) 1 mL gastight syringe and the syringe was placed in an Avanti Polar Lipids Mini-Extruder. The lipid solution was then passed through a 0.20 μm Millipore (Billerica, Mass.) polycarbonate filter 21 times, the newly formed large unilamellar vesicle (LUV) suspension being collected in the syringe that did not contain the original suspension of MLVs to prevent the carryover of MLVs into the LUV solution.

Determination of Phosphorus Content

Determination of total phosphorus was adapted from the report of Chen and coworkers. Chen, P S et al. (1956) *Anal. Chem.* 28:1756. The LUV solution was diluted tenfold with K buffer and three 10 μL samples of the diluted LUV suspension were added to three separate 7 mL vials. Subsequently, the solvent was removed with a stream of $N_2$. To each dried LUV film, and a fourth vial containing no lipids that was used as a blank, was added 450 μL of 8.9 M $H_2SO_4$. The four samples were incubated open to ambient atmosphere in a 225° C. aluminum heating block for 25 min and then removed to 23° C. and cooled for 5 minutes. After cooling, 150 μL of 30% w/v aqueous hydrogen peroxide was added to each sample, and the vials were returned to the 225° C. heating block for 30 minutes. The samples were then removed to 23° C. and cooled for 5 minutes before the addition of 3.9 mL water. Then 500 μL of 2.5% w/v ammonium molybdate was added to each vial and the resulting mixtures were then vortexed briefly and vigorously five times. Subsequently, 500 μL of 10% w/v ascorbic acid was added to each vial and the resulting mixtures were then vortexed briefly and vigorously five times. The vials were enclosed with a PTFE lined cap and then placed in a 100° C. aluminum heating block for 7 minutes. The samples were removed to 23° C. and cooled for approximately 15 minutes prior to analysis by UV/Vis spectroscopy. Total phosphorus was determined by observing the absorbance at 820 nm and comparing this value to a standard curve obtained through this method and a standard phosphorus solution of known concentration.

Determination of Ergosterol Content

Ergosterol content was determined spectrophotometrically. A 50 μL portion of the LUV suspension was added to 450 μL 2:18:9 hexane:isopropanol:water (v/v/v). Three independent samples were prepared and then vortexed vigorously for approximately one minute. The solutions were then analyzed by UV/Vis spectroscopy and the concentration of ergosterol in solution was determined by the extinction coefficient of 10400 L mol$^{-1}$ cm$^{-1}$ at the $UV_{max}$ of 282 nm and was compared to the concentration of phosphorus to determine the percent sterol content. The extinction coefficient was determined independently in the above ternary solvent system. LUVs prepared by this method contained between 7 and 14% ergosterol.

Titration Experiment

Titrations were performed by injecting the LUV suspension at ambient temperature into the sample cell (volume=0.191 mL) which contained the 600 μM solution of the compound in question at 25° C. The volume of the first injection was 0.23 μL. Consistent with standard procedure (Heerklotz, H et al. (2000) *Biochim. Biophys. Acta* 1508:69), due to the large error commonly associated with the first injection of ITC experiments, the heat of this injection was not included in the analysis of the data. Next, six 7.49 µL injections of the LUV suspension were performed. The spacing between each injection was 720 seconds to ensure that the instrument would return to a stable baseline before the next injection was made. The rate of stirring for each experiment was 300 rpm.

Data Analysis

NanoAnalyze software (TA Instruments) was used for baseline determination and integration of the injection heats, and Microsoft Excel was used for subtraction of dilution heats and the calculation of overall heat evolved. To correct for dilution and mixing heats, the heat of the final injection from each run was subtracted from all the injection heats for that particular experiment. See, for example, te Welscher, Y M et al. (2008) *J. Biol. Chem.* 283:6393. By this method, the overall heat evolved during the experiment was calculated using the following formula:

$$\text{"cal}_{overall} = \sum_{i=1}^{n} (\Delta h_{injection}^{i} - \Delta h_{injection}^{n})$$

where i=injection number, n=total number of injections, $\Delta h_{injection}^{i}$=heat of the $i^{th}$ injection, and $\Delta h_{injection}^{n}$=the heat of the final injection of the experiment.

Example 11. C2'epiAmB Exerts Antifungal Activity In Vitro

The activity of AmB and C2'epiAmB against two ergosterol-containing strains of yeast, *S. cerevisiae* and *C. albicans*, was tested. *C. albicans* represents the most common cause of life-threatening systemic fungal infections in humans. C2'epiAmB demonstrated potent antifungal activity against both *S. cerevisiae* (MIC=2 µM) and *C. albicans* (MIC=2 µM).

Exemplary methods for antifungal activity assays are as follows:

Growth Conditions for *S. cerevisiae*

*S. cerevisiae* was maintained with yeast peptone dextrose (YPD) growth media consisting of 10 g/L yeast extract, 20 g/L peptone, 20 g/L dextrose, and 20 g/L agar for solid media. The media was sterilized by autoclaving at 250° F. for 30 min. Dextrose was subsequently added as a sterile 40% w/v solution in water (dextrose solutions were filter sterilized). Solid media was prepared by pouring sterile media containing agar (20 g/L) onto Corning (Corning, N.Y.) 100×20 mm polystyrene plates. Liquid cultures were incubated at 30° C. on a rotary shaker and solid cultures were maintained at 30° C. in an incubator.

Growth Conditions for *C. albicans*

*C. albicans* was cultured in a similar manner to *S. cerevisiae* except both liquid and solid cultures were incubated at 37° C.

Broth Microdilution Minimum Inhibitory Concentration (MIC) Assay

The protocol for the broth microdilution assay was adapted from the Clinical and Laboratory Standards Institute document M27-A2. Clinical and Laboratory Standards Institute. Reference Method for Broth Dilution Antifungal Susceptibility Testing, M27-A2, Approved Standard $2^{nd}$ Ed. Vol. 22, Number 15, 2002. 50 mL of YPD media was inoculated and incubated overnight at either 30° C. (*S. cerevisiae*) or 37° C. (*C. albicans*) in a shaker incubator. The cell suspension was then diluted with YPD to an $OD_{600}$ of 0.10 (~5×10$^5$ cfu/mL) as measured by a Shimadzu (Kyoto, Japan) PharmaSpec UV-1700 UV/Vis spectrophotometer. The solution was diluted 10-fold with YPD, and 195 µL aliquots of the dilute cell suspension were added to sterile Falcon (Franklin Lakes, N.J.) Microtest 96-well plates in triplicate. Compounds may be prepared as 400 µM stock solutions in DMSO and serially diluted to the following concentrations with DMSO: 1600, 1200, 800, 400, 320, 240, 200, 160, 120, 80, 40, 20, 10 and 5 µM. 5 µL aliquots of each solution were added to the 96-well plate in triplicate, with each column representing a different concentration of the test compound. The concentration of DMSO in each well was 2.5% and a control well to confirm viability using only 2.5% DMSO was also performed in triplicate. This 40-fold dilution gave the following final concentrations: 50, 40, 30, 20, 10, 8, 6, 4, 1, 0.5, 0.25 and 0.125 µM. The plates were covered and incubated at 30° C. (*S. cerevisiae*) or 37° C. (*C. albicans*) for 24 hours prior to analysis. The MIC was determined to be the concentration of compound that resulted in no visible growth of the yeast. The experiments were performed in duplicate and the reported MIC represents an average of two experiments.

Example 12. C2'epiAmB is not Toxic to Human Cells In Vitro

The activity of AmB and C2'epiAmB was probed against human cells. Two of the most important toxic side effects associated with AmB are anemia and nephrotoxicity caused by damage to red blood cells and renal proximal tubule cells, respectively. Consistent with literature precedent, AmB causes 90% hemolysis of human red blood cells at a concentration of 8.5 µM. This is defined as the minimum hemolytic concentration (MHC). In stark contrast, it was found that the corresponding MHC for C2'epiAmB, which does not bind cholesterol, is >500 µM. Similarly, AmB causes 90% loss of cell viability of primary human renal proximal tubule epithelial cells at a concentration of 2.4 µM (the minimum toxic concentration (MTC)). Again, in stark contrast to AmB, C2'epiAmB showed no evidence of toxicity up to the limits of solubility.

Exemplary methods for toxicity assays are as follows:

Hemolysis Assays

Erythrocyte Preparation

The protocol for the hemolysis assay was adapted from the report of Paquet and coworkers. Paquet, V et al. (2008) *Chem. Eur. J.* 14:2465-2481. Whole human blood (sodium heparin) was purchased from Bioreclamation LLC (Westbury, N.Y.) and stored at 4° C. and used within two days of receipt. To a 2.0 mL Eppendorf tube, 1 mL of whole human blood was added and centrifuged at 10,000 g for 2 minutes. The supernatant was removed and the erythrocyte pellet was washed with 1 mL of sterile saline and centrifuged at 10,000 g for 2 minutes. The saline wash was repeated for a total of three washes. The erythrocyte pellet was suspended in 1 mL of RBC buffer (10 mM $NaH_2PO_4$, 150 mM NaCl, 1 mM $MgCl_2$, pH 7.4) to form the erythrocyte stock suspension.

Minimum Hemolysis Concentration (MHC) Assay

Compounds were prepared as 1.03 mM (AmB) or 12.8 mM (C2'epiAmB) stock solutions in DMSO and serially diluted to the following concentrations with DMSO: 7689, 5126, 2563, 2050, 1538, 1025, 769, 513, 384, 256, 205, 154, 103, 77, 51, 26 µM. To a 0.2 mL PCR tube, 24 µL of RBC buffer and 1 µL of compound stock solution were added, which gave final concentrations of 500, 300, 200, 100, 80, 60, 40, 30, 20, 15, 10, 8, 6, 4, 3, 2, 1 µM. Positive and negative controls were prepared by adding 1 µL of DMSO to MilliQ water or RBC buffer, respectively to 0.2 mL PCR tube. To each PCR tube, 0.63 µL of the erythrocyte stock suspension was added and mixed by inversion. The samples were incubated at 37° C. for 2 hours. The samples were mixed by inversion and centrifuged at 10,000 g for 2 minutes. 15 µL of the supernatant from each sample was added to a 384-well place. Absorbances were read at 540 nm using a Biotek H1 Synergy Hybrid Reader (Winooski, Vt.). Experiments were performed in triplicate and the reported MHC represents an average of three experiments.

Data Analysis

Percent hemolysis was determined according to the following equation:

$$\% \text{ hemolysis} = \frac{Abs._{sample} - Abs._{neg.}}{Abs._{pos.} - Abs._{neg.}} \times 100\%$$

Concentration vs. percent hemolysis was plotted and fitted to 4-parameter logistic (4PL) dose response fit using OriginPro 8.6. Sebaugh, J L (2011) *Pharmaceut. Statist.* 10:128-134. The MHC was defined as the concentration to cause 90% hemolysis.

WST-8 Cell Proliferation Assays

Primary Renal Proximal Tubule Epithelial Cells Preparation

Primary human renal proximal tubule epithelial cells (RPTECs) were purchased from ATCC (Manassas, Va.) and immediately cultured upon receipt. Complete growth media was prepared using renal epithelial cell basal medium (ATCC, PCS-400-030), renal epithelial cell growth kit (ATCC, PCS-400-040), and penicillin-streptomycin (10 units/mL and 10 µg/mL). Complete media was stored at 4° C. in the dark and used within 28 days. Primary RPTECs were grown in $CO_2$ incubator at 37° C. with an atmosphere of 95% air/5% $CO_2$.

WST-8 Reagent Preparation

WST-8 cell proliferation assay kit (10010199) was purchased from Cayman Chemical Company (Ann Arbor, Mich.) and stored at −20° C. and used within 6 months of receipt. WST-8 reagent and electron mediator solution were thawed and mixed to prepare the WST-8 reagent solution. The solution was stored at −20° C. and used within one week.

WST-8 Assay

A suspension of primary RPTECs in complete growth media was brought to a concentration of $1 \times 10^5$ cells/mL. A 96-well plate was seeded with 99 µL of the cell suspension and incubated at 37° C. with an atmosphere of 95% air/5% $CO_2$ for 3 hours. Positive and negative controls were prepared by seeding with 100 µL of the cell suspension or 100 µL of the complete media. Compounds were prepared as 5 mM (AmB) and 50 mM (C2'epiAmB) stock solutions in DMSO and serially diluted to the following concentrations with DMSO: 50000, 40000, 30000, 20000, 10000, 8000, 6000, 4000, 3000, 2000, 1500, 1000, 800, 600, 400, 300, 200, 100, 50, 25, 10, 5, 2.5, 1, 0.5, 0.25, and 0.1 µM. 1 µL aliquots of each solution were added to the 96-well plate in triplicate, with each column representing a different concentration of the test compound. The 96-well plate was incubated at 37° C. with an atmosphere of 95% air/5% $CO_2$ for 24 hours. After incubation, the media was aspirated and 100 µL of serum-free media was added and 10 µL of the WST-8 reagent solution was added to each well. The 96-well plate was mixed in a shaking incubator at 200 rpm for 1 minute and incubated at 37° C. with an atmosphere of 95% air/5% $CO_2$ for 2 hours. Following incubation, the 96-well plate was mixed in a shaking incubator at 200 rpm for 1 minute and absorbances were read at 450 nm using a Biotek H1 Synergy Hybrid Reader (Winooski, Vt.). Experiments were performed in triplicate and the reported cytotoxicity represents an average of three experiments.

Data Analysis

Percent hemolysis was determined according to the following equation:

$$\% \text{ hemolysis} = \frac{Abs._{sample} - Abs._{neg.}}{Abs._{pos.} - Abs._{neg.}} \times 100\%$$

Concentration vs. percent hemolysis was plotted and fitted to 4-parameter logistic (4PL) dose response fit using OriginPro 8.6. The MTC was defined as the concentration to cause 90% loss of cell viability.

Microscopy

Cells were imaged using an AMG (Bothell, Wash.) EVOS fl Microscope. Images were taken using transmitted light at 10× objective.

Example 13. In Vivo Assessment of Biological Activity

The antifungal efficacy of C2'epiAmB was tested in a mouse model of disseminated candidiasis. In this experiment neutropenic mice were infected with *C. albicans* via their tail veins, and then 2 hours post infection the mice were treated with a single intraperitoneal injection of 16 mg/kg AmB or C2'epiAmB. Then at 24 hours post infection the mice were sacrificed, and the fungal burden present in their kidneys was quantified. C2'epiAmB was more effective than AmB at reducing the fungal burden present in the kidneys. Relative to AmB, C2'epiAmB reduced the fungal burden by 0.5 log units.

In a separate experiment, acute toxicity was determined by single intravenous administration of AmB or C2'epiAmB to healthy mice, followed by monitoring for lethality. All mice in the 4 mg/kg AmB dosage group died within seconds. C2'epiAmB was significantly less toxic, with no deaths observed even up to a dose of 16 mg/kg.

INCORPORATION BY REFERENCE

All patents and published patent applications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

We claim:
1. A compound, represented by

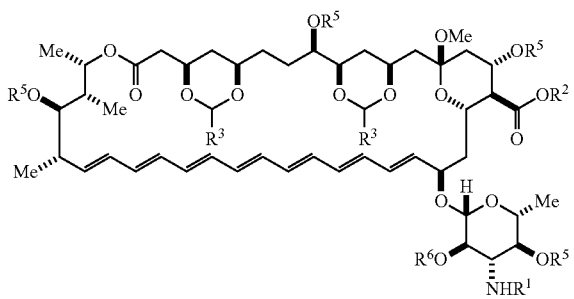

5_{gen} wherein, independently for each occurrence, $R^1$ is $C(O)OR^a$;

$R^2$ is selected from the group consisting of 2-alken-1-yl, benzyl, and $(R^b)_3Si$—;

$R^3$ is substituted or unsubstituted aryl, or $C_1$-$C_6$ alkyl;

$R^5$ is $(R^b)_3Si$—;

$R^6$ is —$C(O)R^c$;

$R^a$ is selected from the group consisting of 2-alken-1-yl, tert-butyl, and benzyl;

$R^b$ is substituted or unsubstituted aryl, or $C_1$-$C_6$ alkyl; and $R^c$ is substituted or unsubstituted aryl.

2. The compound of claim 1, wherein $R^a$ is 2-alken-1-yl; $R^2$ is 2-alken-1-yl; $R^3$ is substituted or unsubstituted aryl; $R^c$ is substituted or unsubstituted phenyl; and $R^b$ is $C_1$-$C_6$ alkyl.

3. The compound of claim 1, represented by

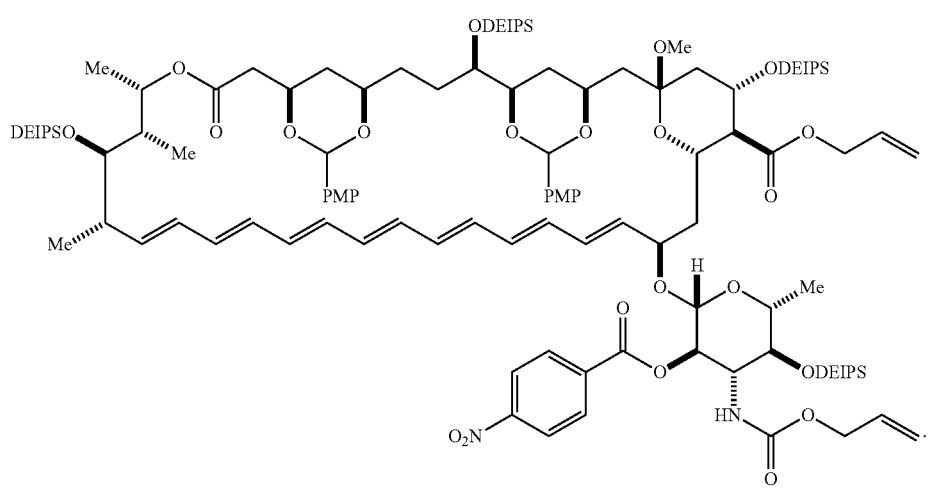

5

4. A compound, represented by

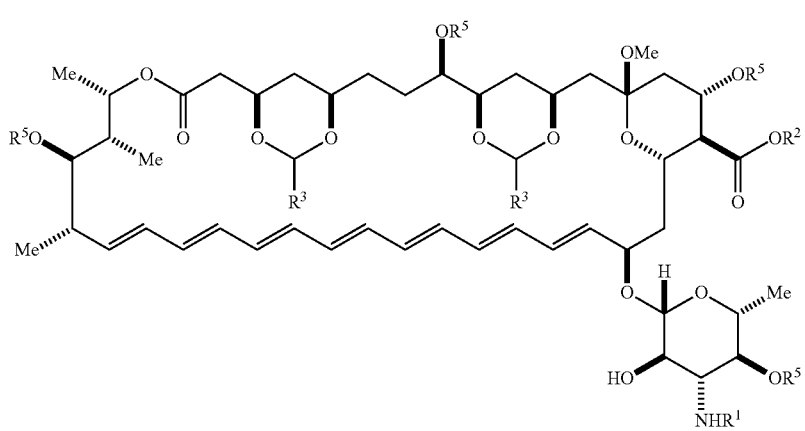

6_{gen} wherein, independently for each occurrence,
$R^1$ is $C(O)OR^a$;
$R^2$ is selected from the group consisting of 2-alken-1-yl, benzyl, and $(R^b)_3Si-$;
$R^3$ is substituted or unsubstituted aryl, or $C_1$-$C_6$ alkyl;
$R^5$ is $(R^b)_3Si-$;

$R^a$ is selected from the group consisting of 2-alken-1-yl, tert-butyl, and benzyl; and
$R^b$ is substituted or unsubstituted aryl, or $C_1$-$C_6$ alkyl.

5. The compound of claim 4, wherein $R^a$ is 2-alken-1-yl; $R^2$ is 2-alken-1-yl; $R^3$ is substituted or unsubstituted aryl; and $R^b$ is $C_1$-$C_6$ alkyl.

6. The compound of claim 4, represented by

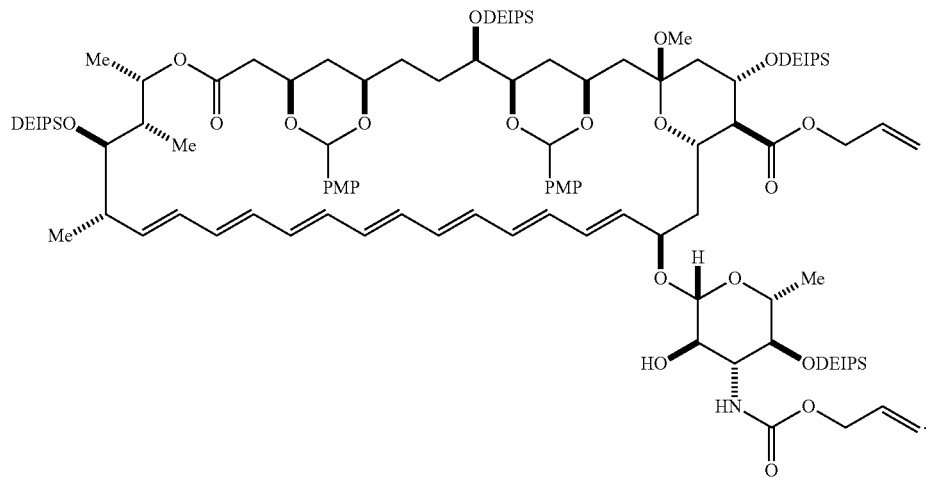

6

7. A compound, represented by

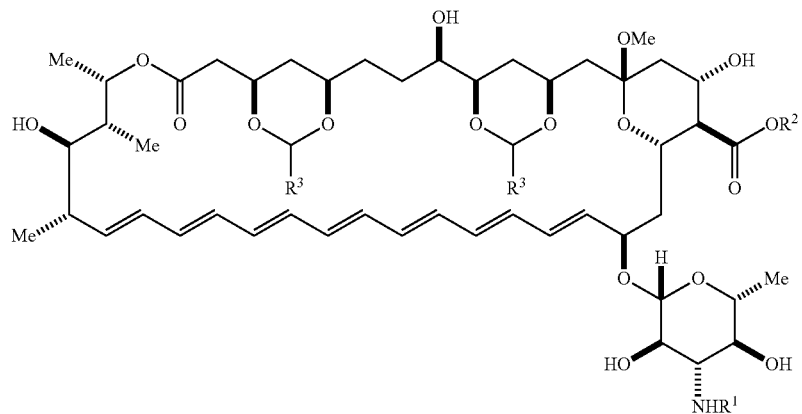

7$_{gen}$ wherein, independently for each occurrence,
R¹ is C(O)OR$^a$;
R² is selected from the group consisting of 2-alken-1-yl, benzyl, and (R$^b$)₃Si—;
R³ is substituted or unsubstituted aryl, or $C_1$-$C_6$ alkyl;
R$^a$ is selected from the group consisting of 2-alken-1-yl, tert-butyl, and benzyl; and R$^b$ is substituted or unsubstituted aryl, or $C_1$-$C_6$ alkyl.

8. The compound of claim 7, wherein R$^a$ is 2-alken-1-yl; R² is 2-alken-1-yl; and R³ is substituted or unsubstituted aryl.

9. The compound of claim 7, represented by

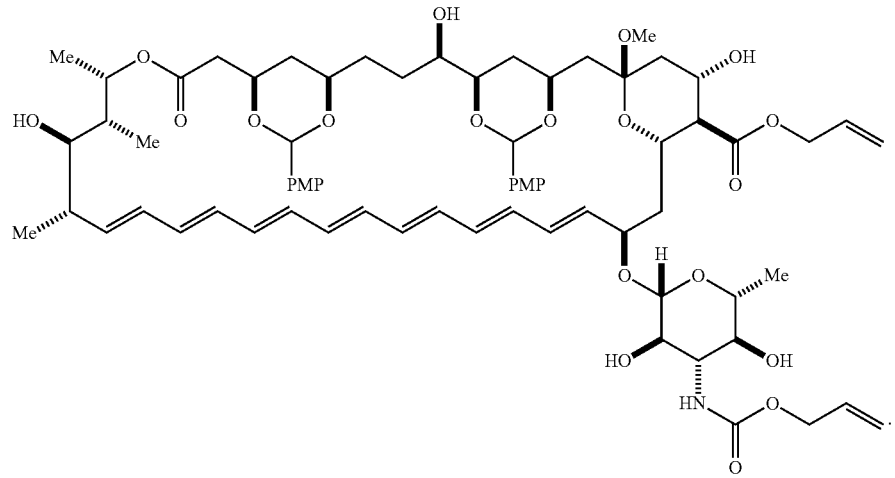

7

10. A compound, represented by

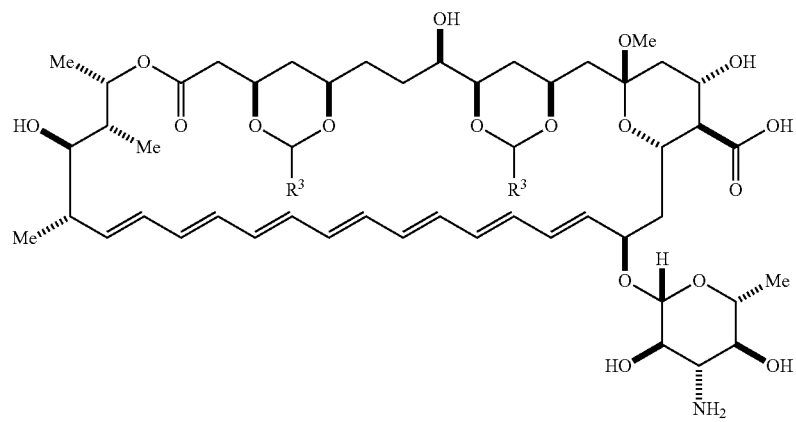

8$_{gen}$ wherein, independently for each occurrence,
R³ is substituted or unsubstituted aryl, or $C_1$-$C_6$ alkyl.
11. The compound of claim 10, wherein R³ is substituted or unsubstituted aryl.
12. The compound of claim 10, represented by
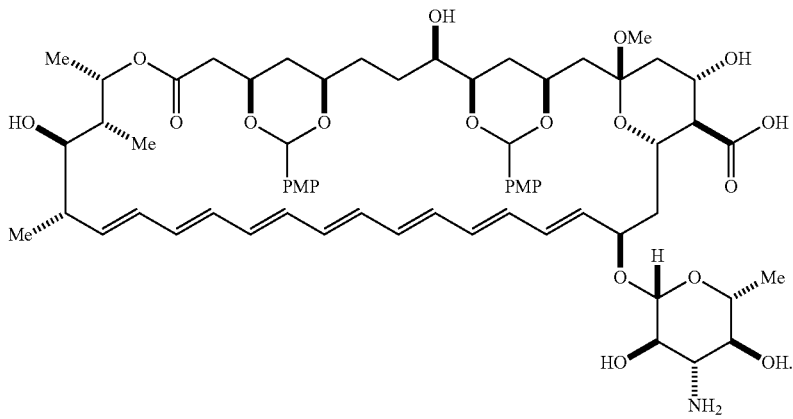
8
13. A method of making 2' epiAmB
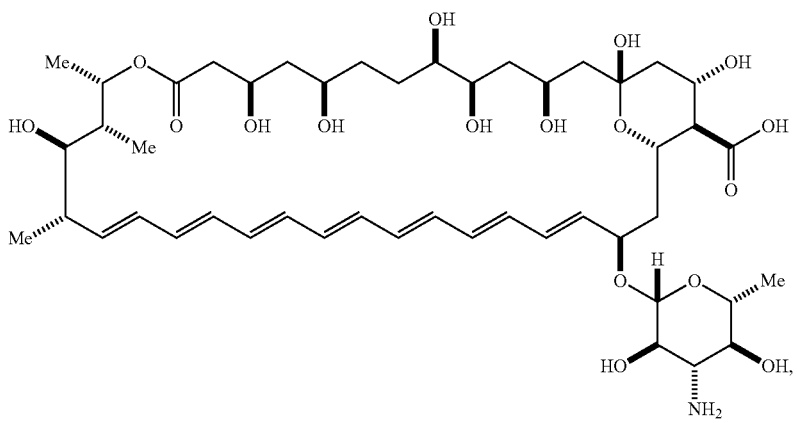
C2'epiAmB
45
comprising the step of:
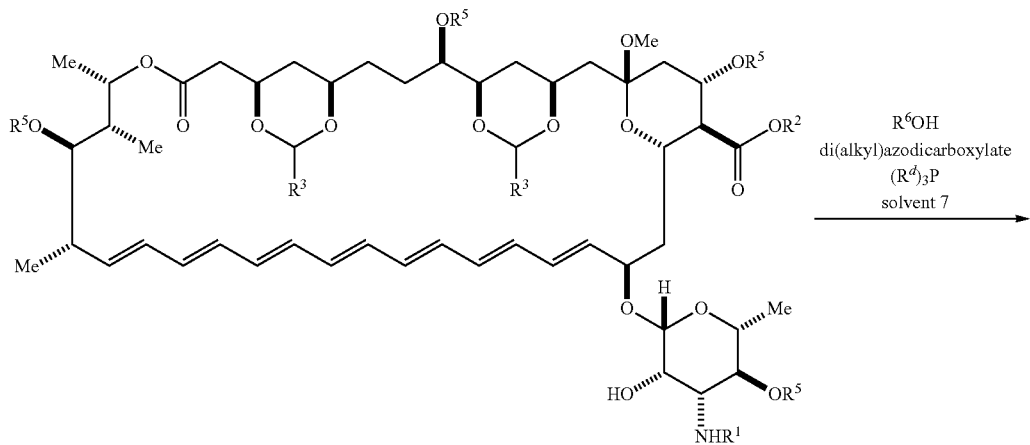
$4_{gen}$ -continued

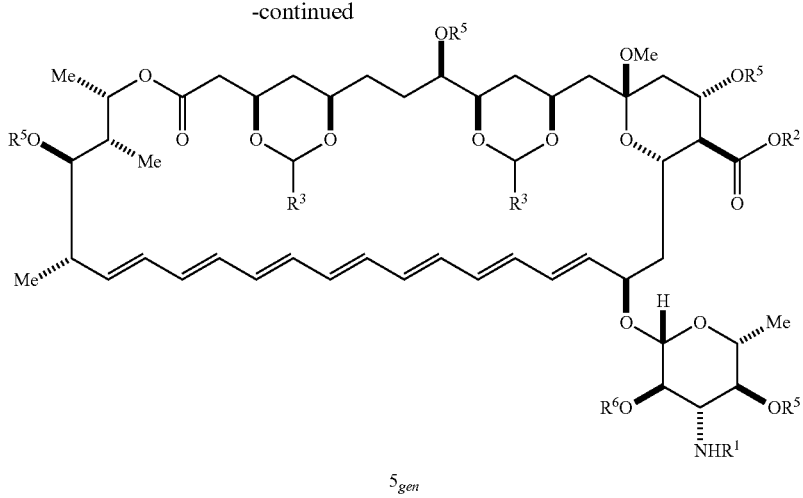

5_gen wherein, independently for each occurrence,
- $R^1$ is $C(O)OR^a$;
- $R^2$ is selected from the group consisting of 2-alken-1-yl, benzyl, and $(R^b)_3Si-$;
- $R^3$ is substituted or unsubstituted aryl, or $C_1$-$C_6$ alkyl;
- $R^5$ is $(R^b)_3Si-$;
- $R^6$ is $-C(O)R^c$;
- $R^a$ is selected from the group consisting of 2-alken-1-yl, tert-butyl, and benzyl;
- $R^b$ is substituted or unsubstituted aryl, or $C_1$-$C_6$ alkyl;
- $R^c$ is substituted or unsubstituted aryl;
- $R^d$ is $C_1$-$C_6$ alkyl or aryl; and
- solvent 7 is a nonpolar aprotic solvent.

* * * * *